US007892767B2

(12) United States Patent
Rubin et al.

(10) Patent No.: US 7,892,767 B2
(45) Date of Patent: Feb. 22, 2011

(54) PHOSPHOSPECIFIC CHEMOKINE RECEPTOR ANTIBODIES

(75) Inventors: Joshua Rubin, Webster Groves, MO (US); Andrew Kung, Walpole, MA (US)

(73) Assignees: Washington University in St. Louis, St. Louis, MO (US); Dana-Farber Cancer Institute, Inc., Boston, MA (US)

( * ) Notice: Subject to any disclaimer, the term of this patent is extended or adjusted under 35 U.S.C. 154(b) by 437 days.

(21) Appl. No.: 11/994,048

(22) PCT Filed: Jun. 30, 2006

(86) PCT No.: PCT/US2006/025573

§ 371 (c)(1),
(2), (4) Date: Jul. 15, 2008

(87) PCT Pub. No.: WO2007/005605

PCT Pub. Date: Jan. 11, 2007

(65) Prior Publication Data
US 2009/0170130 A1 Jul. 2, 2009

Related U.S. Application Data

(60) Provisional application No. 60/696,254, filed on Jul. 1, 2005.

(51) Int. Cl.
G01N 33/53 (2006.01)
G01N 31/00 (2006.01)
(52) U.S. Cl. ................ 435/7.21; 435/7.1; 436/1; 436/501; 436/518; 424/9.1; 424/520; 422/1; 422/50; 422/61; 530/300; 530/350
(58) Field of Classification Search ................ None
See application file for complete search history.

(56) References Cited

U.S. PATENT DOCUMENTS

| 5,096,815 | A | 3/1992 | Ladner et al. |
| 5,198,346 | A | 3/1993 | Ladner et al. |
| 5,223,409 | A | 6/1993 | Ladner et al. |
| 5,599,681 | A | 2/1997 | Epstein et al. |
| 6,863,887 | B1 | 3/2005 | Murphy et al. |
| 6,924,361 | B1 | 8/2005 | Laudano et al. |
| 2005/0002939 | A1 | 1/2005 | Zlotnik et al. |

FOREIGN PATENT DOCUMENTS

| WO | 9105058 A1 | 4/1991 |
| WO | 9320242 A1 | 10/1993 |
| WO | 9418318 A1 | 8/1994 |
| WO | 2007005605 A2 | 1/2007 |

OTHER PUBLICATIONS

Ahmed et al., "Cisplatin, cytarabine, caffeine, and continuously infused 5-fluorouracil (PACE) in the treatment of advanced pancreatic carcinoma: a phase II study", American Journal of Clinical Oncology, 2000, pp. 420-424, vol. 23, No. 4.

Altschul et al., "Basic Local alignment search tool", Journal of Molecular Biology, 1990, pp. 403-410, vol. 215.

Altschul et al., "Gapped BLAST and PSI-BLAST: a new generation of protein database search programs", Nucleic Acids Research, 1997, pp. 3389-3402; vol. 25, No. 17.

Andersen et al., "A conserved alternative splice in the von Recklinghausen neurofibromatosis (NF1) gene produces two neurofibromin isoforms, both of which have GTPase-activating protein activity", Molecular and Cellular Biology, 1993, pp. 487-495; vol. 13, No. 1.

Bachelder et al., "Vascular endothelial growth factor promotes breast carcinoma invasion in an autocrine manner by regulating the chemokine receptor CXCR4", Cancer Research, 2002, pp. 7203-7206, vol. 62, No. 24.

Bagri et al., "The chemokine SDF1 regulates migration of dentate granule cells" Development, 2002, pp. 4249-4260, vol. 129, No. 18.

Bajenaru et al., "Neurofibromatosis 1 (NF1) heterozygosity results in a cell-autonomous growth advantage for astrocytes", GLIA, 2001, pp. 314-323, vol. 33, No. 4.

Bajenaru et al., "Natural history of neurofibromatosis 1-associated optic nerve glioma in mice", Annals of Neurology, 2005, pp. 119-127, vol. 57, No. 1.

Bajenaru et al., "Optic nerve glioma in mice requires astrocyte Nf1 gene inactivation and Nf1 brain heterozygosity", Cancer Research, 2003, pp. 8573-8577; vol. 63, No. 24.

Bajenaru et al., "Astrocyte-specific inactivation of the neurofibromatosis 1 gene (NF1) is insufficient for astrocytoma formation", Molecular and Cellular Biology, 2002, pp. 5100-5113, vol. 22, No. 14.

Balkwill, "The significance of cancer cell expression of the chemokine receptor CXCR4", Seminars in Cancer Biology, 2004, pp. 171-179, vol. 14, No. 3.

Ballester et al., "The NF1 locus encodes a protein functionally related to mammalian GAP and yeast IRA proteins" Cell, 1990, pp. 851-859, vol. 63, No. 4.

Balmanno et al., "deltaRaf-1:ER* bypasses the cyclic AMP block of extracellular signal-regulated kinase 1 and 2 activation but not CDK2 activation or cell cycle reentry", Molecular and Cellular Biology, 2003, pp. 9303-9317, vol. 23, No. 24.

Bangalore et al., Antiserum raised against a synthetic phosphotyrosine-containing peptide selectively recognizes p185neu/erbB-2 and the epidermal growth.

(Continued)

*Primary Examiner*—Lisa V Cook
(74) *Attorney, Agent, or Firm*—Polsinelli Shughart PC

(57) ABSTRACT

The present invention provides chemokine receptor antibodies that selectively bind to an activated form of the receptor but not to a non activated form of the receptor. In particular, the current invention provides phosphospecific chemokine receptor antibodies. The antibodies can be used in several diagnostic, screening and purification methods.

31 Claims, 39 Drawing Sheets

OTHER PUBLICATIONS

Barbero et al., "Stromal cell-derived factor 1alpha stimulates human glioblastoma cell growth through the activation of both extracellular signal-related kinases 1/2 and Akt", Cancer Research, 2003, pp. 1969-1974, vol. 63, No. 8.

Basu et al., "Transforming growth factor-beta 1 modulates responses of CD34+ cord blood cells to stromal cell-derived factor-1/CXCL12", Blood, 2005, pp. 485-493, vol. 106, No. 2.

Bleul et al., "B lymphocyte chemotaxis regulated in association with microanatomic localization, differentiation state, and B cell receptor engagement", Journal of Experimental Medicine, 1998, pp. 753-762, vol. 187, No. 5.

Bock et al., "Selection of single-stranded DNA molecules that bind and inhibit human thrombin", Nature, 1992, pp. 564-566, vol. 355.

Bollag et al., "Loss of NF1 results in activation of the Ras signaling pathway and leads to aberrant growth in haematopoietic cells", Nature Genetics, 1996, pp. 144-148, vol. 12, No. 2.

Brenner et al., "Encoded combinatorial chemistry" Proceedings of the National Academy of Sciences USA, 1992, pp. 5381-5383, vol. 89, No. 12.

Bridger et al., "Synthesis and structure-activity relationships of phenylenebis(methylene)-linked bisazamacrocycles that inhibit HIV-1 and HIV-2 replication by antagonism of the chemokine receptor CXCR4", Journal of Medicinal Chemistry, 1999, pp. 3971-3981, vol. 42, No. 19.

Broxmeyer et al., "Rapid mobilization of murine and human hematopoietic stem and progenitor cells with AMD3100, a CXCR4 antagonist", Journal of Experimental Medicine, 2005, pp. 1307-1318, vol. 201, No. 8.

Burchill et al., "Contrasting levels of p21ras activation and expression of neurofibromin in peripheral primitive neuroectodermal tumour and neuroblastoma cells, and their response to retinoic acid", Journal of Neurological Sciences, 1998, pp. 129-137, vol. 157, No. 2.

Burger et al., "Glioblastoma multiforme and anaplastic astrocytoma. Pathologic criteria and prognostic implications", Cancer, 1985, pp. 1106-1111, vol. 56, No. 5.

Burton et al., "A Large array of human monoclonal antibodies to type 1 human immudodeficiency virus from combinatorial libraries of asymptomatic seropositive individuals", Proceedings of the National Academy of Sciences USA, 1991, pp. 10134-10137, vol. 88.

Chalasani et al., "The chemokine stromal cell-derived factor-1 promotes the survival of embryonic retinal ganglion cells", Journal of Neuroscience, 2003, pp. 4601-4612, vol. 23, No. 11.

Cheng et al., "beta-arrestin differentially regulates the chemokine receptor CXCR4-mediated signaling and receptor internalization, and this implicates multiple interaction sites between beta-arrestin and CXCR4", Journal of Biological Chemistry, 2000, pp. 2479-2485, vol. 275, No. 4.

Christian et al., "Simplified methods for construction, assessment and rapid screening of peptide libraries in bacteriophage", Journal of Molecular Biology, 1992, pp. 711-718, vol. 227.

Cole et al., "Human monoclonal antibodies", Molecular and Cellular Biochemistry, 1984, pp. 109-120, vol. 62.

Cote et al., "Generation of human monoclonal antibodies reactive with cellular antigens", Proceedings of the National Academy of Sciences USA, 1983, pp. 2026-2030, vol. 80.

Cowan, "Roflumilast for asthma and chronic obstructive pulmonary disease", Issues in Emerging Health Technologies, 2005, pp. 1-4, Issue 74.

Daaka et al., "Essential role for G protein-coupled receptor endocytosis in the activation of mitogen-activated protein kinase", Journal of Biological Chemistry, 1998, pp. 685-688, vol. 273, No. 2.

Dasgupta et al., "The neurofibromatosis 1 gene product neurofibromin regulates pituitary adenylate cyclase-activating polypeptide-mediated signaling in astrocytes", Journal of Neuroscience, 2003, pp. 8949-8954, vol. 23, No. 26.

Dasgupta et al., "Glioma formation in neurofibromatosis 1 reflects preferential activation of K-RAS in astrocytes", Cancer Research, 2005, pp. 236-245, vol. 65, No. 1.

Dasgupta et al., "Proteomic analysis reveals hyperactivation of the mammalian target of rapamycin pathway in neurofibromatosis 1-associated human and mouse brain tumors", Cancer Research, 2005, pp. 2755-2760, vol. 65, No. 7.

De Clercq, "The bicyclam AMD3100 story", Nature Reviews Drug Discovery, 2003, pp. 581-587, vol. 2, No. 7.

Declue et al., "Abnormal regulation of mammalian p21ras contributes to malignant tumor growth in von Recklinghausen (type 1) neurofibromatosis", Cell, 1992, pp. 265-273, vol. 69, No. 2.

Devine et al., "Rapid mobilization of CD34+ cells following administration of the CXCR4 antagonist AMD3100 to patients with multiple myeloma and non-Hodgkin's lymphoma", Journal of Clinical Oncology, 2004, pp. 1095-1102, vol. 22, No. 6.

Devlin et al., "Random peptide libraries: a source of specific protein binding molecules", Science, 1990, pp. 404-406, vol. 249.

Doronin et al., "Akt mediates sequestration of the beta(2)-adrenergic receptor in response to insulin", Journal of Biological Chemistry, 2002, pp. 15124-15131, vol. 277, No. 17.

Dyke et al., "Update on the therapeutic potential of PDE4 inhibitors", Expert Opinion on Investigational Drugs, 2002, pp. 1-13, vol. 11, No. 1.

Ehtesham et al., "CXCR4 expression mediates glioma cell invasiveness", Oncogene , 2006, pp. 2801-2806, vol. 25, No. 19.

Ellington et al., "Selection in vitro of single-stranded DNA molecules that fold into specific ligand-binding structures", Nature, 1992, pp. 850-852, vol. 355.

Erb et al., "Recursvie deconvoluation of combinatorial chemical libraries", Proceedings of the National Academy of Sciences USA, 1994, pp. 11422-11426, vol. 91.

Feldkamp et al., "Neurofibromatosis type 1 peripheral nerve tumors: aberrant activation of the Ras pathway", Surgical Neurology, 1999, pp. 211-218, vol. 51, No. 2.

Ferguson et al., "G-protein-coupled receptor regulation: role of G-protein-coupled receptor kinases and arrestins", Canadian Journal of Physiology and Pharmacology, 1996; pp. 1095-1110, vol. 74, No. 10.

Ferguson et al., "Molecular mechanisms of G protein-coupled receptor desensitization and resensitization", Life Sciences, 1998, pp. 1561-1565, vol. 62, No. 17-18.

Floridi et al., "Signalling pathways involved in the chemotactic activity of CXCL12 in cultured rat cerebellar neurons and CHP100 neuroepithelioma cells", 2003, Journal of Neuroimmunology, pp. 38-46, vol. 135.

Fodor et al., "Light-directed, spatially addressable parallel chemical synthesis", Science, 1991, pp. 767-773, vol. 251.

Fowlkes et al., "Multipurpose vectors for peptide expression on the M13 viral surface", BioTechniques, 1992, pp. 422-428, vol. 13, No. 3.

Fuller et al., "Amplified cellular oncogenes in neoplasms of the human central nervous system", Mutation Research, 1992, pp. 299-306, vol. 276.

Furman et al., "Cyclis AMP and adenyl cyclase in brain tumors", Journal of Neurosurgy. 1977, pp. 477-483. vol. 46.

Gainetdinov et al., "Desensitization of G protein-coupled receptors and neuronal functions", Annual Review of Neuroscience, 2004, pp. 107-144, vol. 27.

Gallop et al., "Applications of combinatorial technologies to drug discovery. 1. Background and peptide combinatorial libraries", Journal of Medicinal Chemistry, 1994, pp. 1233-1251, vol. 37, No. 9.

Gerlach et al., "Molecular interactions of cyclam and bicyclam non-peptide antagonists with the CXCR4 chemokine receptor", Journal of Biological Chemistry, 2001, pp. 14153-14160, vol. 276, No. 17.

Gomez Del Pulgar et al., "Cannabinoids protect astrocytes from ceramide-induced apoptosis through the phosphatidylinositol 3-kinase/protein kinase B pathway", Journal of Biological Chemistry, 2002, pp. 36527-36533, vol. 277, No. 39.

Gross et al., "Real-time imaging of ligand-induced IKK activation in intact cells and in living mice", Nature Methods, 2005, pp. 607-614, vol. 2, No. 8.

Guha et al., "Expression of PDGF and PDGF receptors in human astrocytoma operation specimens supports the existence of an autocrine loop", International Journal of Cancer, 1995, pp. 168-173, vol. 60.

Guha et al., "Expression of platelet derived growth factor and platelet derived growth factor receptor mRNA in a glioblastoma from a patient with Li-Fraumeni syndrome" Journal of Neurology, Neurosurgy and Psychiatry, 1995, pp. 711-714, vol. 58, No. 6.

Guha, "Ras activation in astrocytomas and neurofibromas", Canadian Journal of Neurological Sciences, 1998, pp. 267-281, vol. 25, No. 4.

Guinamard et al., "B cell antigen receptor engagement inhibits stromal cell-derived factor (SDF)-1alpha chemotaxis and promotes protein kinase C (PKC)-induced internalization of CXCR4", Journal of Experimental Medicine, 1999, pp. 1461-1466, vol. 189, No. 9.

Guleng et al., "Blockade of the stromal cell-derived factor-1/CXCR4 axis attenuates in vivo tumor growth by inhibiting angiogenesis in a vascular endothelial growth factor-independent manner", Cancer Research, 2005, pp. 5864-5871, vol. 65, No. 13.

Guo et al., "Requirement of Drosophila NF1 for activation of adenylyl cyclase by PACAP38-like neuropeptides", Science, 1997, pp. 795-798, vol. 276, No. 5313.

Gutmann et al., "Loss of neurofibromatosis 1 (NF1) gene expression in NF1-associated pilocytic astrocytomas", Neuropathology and Applied Neurobiology, 2000, pp. 361-367, vol. 26, No. 4.

Gutmann et al., "Molecular analysis of astrocytomas presenting after age 10 in individuals with NF1", Neurology, 2003, pp. 1397-1400, vol. 61, No. 10.

Gutmann et al., "Haploinsufficiency for the neurofibromatosis 1 (NF1) tumor suppressor results in increased astrocyte proliferation", Oncogene, 1999, pp. 4450-4459, vol. 18, No. 31.

Gutmann et al., "Identification of the neurofibromatosis type 1 gene product", Proceedings of the National Academy of Sciences USA, 1991, pp. 9658-9662, vol. 88, No. 21.

Harada et al., "Phosphorylation and inactivation of BAD by mitochondria-anchored protein kinase A", Molecular Cell, 1999, pp. 413-422, vol. 3.

Haribabu et al., "Regulation of human chemokine receptors CXCR4. Role of phosphorylation in desensitization and internalization", Journal of Biological Chemistry, 1997, pp. 28726-28731, vol. 272, No. 45.

Hatse et al., "Chemokine receptor inhibition by AMD3100 is strictly confined to CXCR4", FEBS Letters, 2002. pp. 255-262, vol. 527, Nos. 1-3.

Hatse et al., "AMD3465, a monomacrocyclic CXCR4 antagonist and potent HIV entry inhibitor", Biochemical Pharmacology, 2005, pp. 752-761, vol. 70.

Hendrix et al., "Pharmacokinetics and safety of AMD-3100, a novel antagonist of the CXCR-4 chemokine receptor, in human volunteers", Antimicrobial Agents and Chemotherapy, 2000, pp. 1667-1673, vol. 44, No. 6.

Hendrix et al., "Safety, Pharmacokinetics, and Antiviral Activity of AMD3100, a Selective CXCR4 Receptor Inhibitor, in HIV-1 Infection", Journal of Aquired Immune Deficiency Syndromes, 2004, pp. 1253-1262, vol. 37, No. 2.

Hermanson et al., "Platelet-derived growth factor and its receptors in human glioma tissue: expression of messenger RNA and protein suggests the presence of autocrine and paracrine loops", Cancer Research, 1992, pp. 3213-3219, vol. 52, No. 11.

Hirano et al., "Insulin-like growth factor-1 content and pattern of expression correlates with histopathologic grade in diffusely infiltrating astrocytomas", Neuro-Oncology, 1999, pp. 109-119, vol. 1, No. 2.

Pitcher et al., "Feedback inhibition of G protein-coupled receptor kinase 2 (GRK2) activity by extracellular signal-regulated kinases", Journal of Biological Chemistry, 1999, pp. 34531-34534, vol. 274, No. 49.

Pollok-Kopp et al., "Analysis of Ligand-stimulated CC Chemokine Receptor 5 (CCR5) Phosphorylation in Intact Cells Using Phosphosite-specific Antibodies" Journal of Biological Chemistry, 2003, pp. 2190-2198, vol. 278, No. 4.

Racagni et al., "Cyclic nucleotides in experimental and human brain tumors", Journal of Neuro-Oncology, 1983, pp. 61-67, vol. 1, No. 1.

Rebar et al., "Zinc finger phage: affinity selection of fingers with new DNA-dinding specifications", Science, 1994, pp. 671-673, vol. 263.

Reginato et al., "Integrins and EGFR coordinately regulate the pro-apoptotic protein Bim to prevent anoikis", Nature Cell Biology, 2003, pp. 733-740, vol. 5, No. 8.

Reis et al., "Genetic evidence of the neoplastic nature of gemistocytes in astrocytomas", Acta Neuropathologica, 2001, pp. 422-425, vol. 102, No. 5.

Rempel et al., "Identification and localization of the cytokine SDF1 and its receptor, CXC chemokine receptor 4, to regions of necrosis and angiogenesis in human glioblastoma", Clinical Cancer Research, 2000, pp. 102-111, vol. 6, No. 1.

Riccardi, "Cutaneous manifestation of neurofibromatosis: cellular interaction, pigmentation, and mast cells", Birth Defects: Original Article Series, 1981, pp. 129-145, vol. 17, No. 2.

Roland et al., "Role of the intracellular domains of CXCR4 in SDF-1-mediated signaling", Blood, 2003, pp. 399-406, vol. 101, No. 2.

Rosser et al., "Intracranial neoplasms in children with neurofibromatosis 1", Journal of Child Neurology, 2002, pp. 630-637, vol. 17, No. 8.

Rosu-Myles et al., "SDF-1 enhances the expansion and maintenance of highly purified human hematopoietic progenitors", The Hematology Journal, 2003, pp. 137-145, vol. 4, No. 2.

Rubin et al., "Neurofibromatosis type I—a model for nervous system tumour formation?", Nature Reviews Cancer, 2005, pp. 557-564, vol. 5, No. 7.

Rubin et al., "A small-molecule antagonist of CXCR4 inhibits intracranial growth of primary brain tumors", Proceedings of the National Academy of Sciences USA, 2003, pp. 13513-13518, vol. 100, No. 23.

Rubin et al., "Cerebellar proteoglycans regulate sonic hedgehog responses during development", Development, 2002, pp. 2223-2232, vol. 129.

Salcedo et al., "Vascular endothelial growth factor and basic fibroblast growth factor induce expression of CXCR4 on human endothelial cells: In vivo neovascularization induced by stromal-derived factor-1alpha", Americal Journal of Pathology, 1999, pp. 1125-1135, vol. 154, No. 4.

Salmaggi et al., "CXCL12 in malignant glial tumors: a possible role in angiogenesis and cross-talk between endothelial and tumoral cells", Journal of Neuro-Oncology, 2004, pp. 305-317, vol. 67.

Salmon et al., "Discovery of biologically active peptides in random libraries: Solution-phase testing after staged orthogonal release from resin beads" Proceedings of the National Academy of Sciences USA, 1993, pp. 11708-11712, vol. 90.

Sanai et al., "Neural stem cells and the origin of gliomas", New England Journal of Medicine, 2005, pp. 811-822, vol. 353, No. 8.

Scott et al., "Searching for peptide ligands with an epitope library", Science, 1990, pp. 386-390, vol. 249.

Segal et al., "Differential utilization of Trk autophosphorylation sites" Journal of Biological Chemistry, 1996, pp. 20175-20181, vol. 271, No. 33.

Houghten et al., "Generation and use of synthetic peptide combinatorial libraries for basic research and drug discovery", Nature, 1991, pp. 84-86, vol. 354.

Houghten et al., "The use of synthetic peptide combinatorial libraries for the identification of bioactive peptides", Biotechniques, 1992, pp. 412-421, vol. 13.

Huse et al., "Generation of a large combinatorial library of the immunoglobulin repertoire in phage lambda", Science, 1989, pp. 1275-1281, vol. 246, No. 4935.

International Search Report for PCT/US2006/25573 dated May 10, 2007, 4 pages.

Ishii et al., "Physiological actions of regulators of G-protein signaling (RGS) proteins", Life Sciences, 2003, pp. 163-171, vol. 74, Nos. 2-3.

Ishii et al., "Expression of stromal cell-derived factor-1/pre-B cell growth-stimulating factor receptor, CXC chemokine receptor 4, on CD34+ human bone marrow cells is a phenotypic alteration for committed lymphoid progenitors", Journal of Immunology, 1999, pp. 3612-3620, vol. 163.

Janss et al., "Caffeine and staurosporine enhance the cytotoxicity of cisplatin and camptothecin in human brain tumor cell lines", Experimental Cell Research, 1998, pp. 29-38, vol. 243.

Jayawickreme et al., "Creation and functional screening of a multi-use peptide library", Proceedings of the National Academy of Sciences USA, 1994, pp. 1614-1618, vol. 91.

Karlin et al., "Methods for assessing the statistical significance of molecular sequence features by using general scoring schemes", Proceedings of the National Academy of Sciences USA, 1990, pp. 2264-2268, vol. 87.

Kato et al., "Cyclic AMP-induced G1 phase arrest mediated by an inhibitor (p27Kip1) of cyclindependent kinase 4 activation", Cell, 1994, pp. 487-496, vol. 79.

Kay et al., "An M13 phage library displaying random 38-amino-acid peptides as a source of novel sequences with affinity to selected targets" Gene, 1993, pp. 59-65, vol. 128.

Kilic et al., "Intracranial inhibition of platelet-derived growth factor-mediated glioblastoma cell growth by an orally active kinase inhibitor of the 2-phenylaminopyrimidine class", Cancer Research, 2000, pp. 5143-5150, vol. 60.

Kim et al., "8-CL-cAMP induces cell cycle-specific apoptosis in human cancer cells.", International Journal of Cancer, 2001, pp. 33-41, vol. 93.

Kleihues et al., "Primary and secondary glioblastomas: from concept to clinical diagnosis", Neuro-Oncology1, 1999, pp. 44-51, vol. 1.

Klein et al., "SDF-1 alpha induces chemotaxis and enhances Sonic hedgehog-induced proliferation of cerebellar granule cells", Development, 2001, pp. 1971-1981, vol. 128, No. 11.

Klein et al., "Immune and nervous system CXCL12 and CXCR4: parallel roles in patterning and plasticity", Trends in Immunology, 2004, p. 306-314, vol. 25, No. 6.

Kluwe et al., "Loss of NF1 alleles distinguish sporadic from NF1-associated pilocytic astrocytomas", Journal of Neuropathology and Experimantal Neurology, 2001, pp. 917-920, vol. 60, No. 9.

Kohler et al., "Continuous cultures of fused cells secreting antibody of predefined specificity", Nature, 1975, pp. 495-497, vol. 256.

Kondo et al., "Molecular targeting for malignant gliomas (Review)", International Journal of Oncology, 2004, pp. 1101-1109, vol. 24.

Kozbor et al., "Specific immunoglobulin production and enhanced tumorigenicity following ascities growth of human hybridomas", Journal of Immunology Methods, 1985, pp. 31-42, vol. 81.

Kryczek et al., "CXCL12 and vascular endothelial growth factor synergistically induce neoangiogenesis in human ovarian cancers", Cancer Research, 2005, pp. 465-472, vol. 65, No. 2.

Lam et al., "A new type of synthetic peptide library for identifying ligand-binding activity", Nature, 1991, pp. 82-84, vol. 354.

Lassman et al., "Response of glioblastomas to EGFR kinase inhibitors", New England Journal of Medicine, 2006, pp. 525-526, vol. 354, No. 5.

Lataillade et al., "Stromel cell-derived factor 1 regulates primitive hematopoiesis by suppressing apoptosis and by promoting G(0)/G(1) transition in CD34(+) cells: evidence for an autocrine/paracrine mechanism", Blood, 2002, pp. 1117-1129, vol. 99, No. 4.

Lataillade et al., "Chemokine SDF-1 enhances circulating CD34(+) cell proliferation in synergy with cytokines: possible role in progenitor survival", Blood 2000, pp. 756-768, vol. 95, No. 3.

Lee et al., "A68: A Major Subunit of Paired Helical Filaments and Derivatized Forms of Normal Tau", Science, 1991, pp. 675-678, vol. 251.

Lee et al., "Involvement of the Chemokine Receptor CXCR4 and Its Ligand Stromal Cell-Derived Factor 1alpha in Breast Cancer Cell Migration Trhough Human Brain Microvascular Endothelial Cells", Molecular Cancer Research, 2004, pp. 327-338, vol. 2, No. 6.

Lenstra et al., "Isolation of sequences from a random-sequence expression library that mimic viral epitopes", Journal of Immunology Methods, 1992, pp. 149-157, vol. 152.

Lewis et al., "Von Recklinghausen neurofibromatosis. II. Incidence of optic gliomata", Ophthalmology, 1984, pp. 929-935, vol. 91, No. 8.

Li et al., "Cytochrome c release and apoptosis induced by mitochondrial targeting of nuclear orphan receptor TR3", Science, 2000, pp. 1159-1164, vol. 289.

Libermann et al., "Amplification, enhanced expression and possible rearrangement of EGF receptor gene in primary human brain tumours of glial origin", Nature, 1985, pp. 144-147, vol. 313, No. 5998.

Listernick et al., "Optic pathway gliomas in children with neurofibromatosis 1: consensus statement from the NF1 Optic Pathway Glioma Task Force", Annals of Neurology, 1997, pp. 143-149, vol. 41, No. 2.

Lois et al., "Germline transmission and tissue-specific expression of transgenes delivered by lentiviral vectors", Science, 2002, pp. 868-872, vol. 295.

Lu et al., "Abnormal development of the hippocampal dentate gyrus in mice lacking the CXCR4 chemokine receptor", Proceedings of the National Academy of Sciences USA, 2002, pp. 7090-7095, vol. 99, No. 10.

Ma et al., "The chemokine receptor CXCR4 is required for the retention of B lineage and granulocytic precursors within the bone marrow microenvironment", Immunity, 1999, pp. 463-471, vol. 10.

MacDonald et al., "Expression profiling of medulloblastoma: PDGFRA and the RAS/MAPK pathway as therapeutic targets for metastatic disease", Nature Genetics, 2001, pp. 143-152, vol 29.

Magnaldo et al., "Cyclic AMP inhibits mitogen induced DNA synthesis in hamster fibroblasts, regardless of the signaling pathway involved", FEBS Letters, 1989, pp. 65-69, vol. 245, Nos. 1-2.

Marchuk et al., "cDNA cloning of the type 1 neurofibromatosis gene: complete sequence of the NF1 gene product", Genomics, 1991, pp. 931-940, vol. 11.

Marinissen et al., "G-protein-coupled receptors and signaling networks: emerging paradigms", Trends in Pharmacological Sciences, 2001, pp. 368-376, vol. 22, No. 7.

Martin et al., "The GAP-related domain of the neurofibromatosis type 1 gene product interacts with ras p21", Cell, 1990, pp. 843-849, vol. 63, No. 4.

Matteakis et al., "An in vitro polysome display system for identifying ligands from very large peptide libraries", Proceedings of the National Academy of Sciences, USA, 1994, pp. 9022-9026, vol. 91.

Mauro et al., "Coexpression of platelet-derived growth factor (PDGF) B chain and PDGF B-type receptor in human gliomas", Child's Nervous System, 1991, pp. 432-436, vol. 7, No. 8.

Mawrin et al., "Prognostic relevance of MAPK expression in glioblastoma multiforme", International Journal of Oncology, 2003, pp. 641-684, vol. 23.

Maxwell et al., "Coexpression of platelet-derived growth factor (PDGF) and PDGF-receptor genes by primary human astrocytomas may contribute to their development and maintenance", Journal of Clinical Investigation, 1990, pp. 131-140, vol. 86, No. 1.

Medynski, "Synthetic peptide combinatorial libraries", Bio/Technology, 1994, pp. 709-710, vol. 12.

Metaye et al., "Expression and activity of G protein coupled receptor kinases in differentiated thyroid carcinoma", Journal of Clinical Endocrinology and Metabolism, 2002, pp. 3279-3286, vol. 87, No. 7.

Miller et al., "Expanding roles for beta-arrestins as scaffolds and adapters in GPCR signaling and trafficking", Current Opinion in Cell Biology, 2001, p. 139-145, vol. 13.

Morrison et al., "Chimeric human antibody molecules : Mouse antigen-binding domains with human constant region domains", Proceedings of the National Academy of Sciences USA, 1984, pp. 6851-6855, vol. 81.

Neuberger et al., "Recombinant antibodies possessing novel effector functions", Nature, 1984, pp. 604-608, vol. 312.

Ohlmeyer et al., "Complex synthetic chemical libraries indexed with molecular tags", Proceedings of the National Academy of Sciences USA, 1993, pp. 10922-10926, vol. 90.

Oldenburg et al., "Peptide ligands for a sugar-binding protein isolated from a random peptide library", Proceedings of the National Academy of Sciences USA, 1992, pp. 5393-5397, vol. 89.

Oliver et al., "Loss of patched and disruption of granule cell development in a pre-neoplastic stage of medulloblastoma", Development, 2005, pp. 2425-2439, vol. 132.

Orlandi et al., "Cloning immunoglobulin variable domains for expression by the polymerase chain reaction", Proceedings of the National Academy of Science USA, 1989, pp. 3833-3837, vol. 86.

Orsini et al., "Trafficking of the HIV coreceptor CXCR4: role of arrestins and identification of residues in the C-terminal tail that mediate receptor internalization", Journal of Biological Chemistry, 1999, pp. 31076-31086, vol. 274, No. 43.

Packer et al., "Medulloblastoma:clinical and biologic aspects", Neuro-Oncology vol. 1, 1999, pp. 232-250.

Parmley et al., "Antibody-selectable filamentous fd phage vectors: affinity purification of target genes", Gene, 1988, pp. 305-318, vol. 73.

Parmley et al., "Filamentous fusion phage cloning vectors for the study of epitopes and design of vaccines" Advances in Experimental Medine and Biology, 1989, pp. 215-218, vol. 251.

Penela et al., "Mechanisms of regulation of the expression and function of G protein-coupled receptor kinases", Cellular Signaling, 2003, pp. 973-981, vol. 15, No. 11.

Peng et al., "Stromal cell-derived factor 1-mediated CXCR4 signaling in rat and human cortical neural progenitor cells", Journal of Neuroscience Research, 2004, pp. 35-50, vol. 76, No. 1.

Phillips et al., "The mechanism of Ras GTPase activation by neurofibromin", Biochemistry, 2003, pp. 3956-3965, vol. 42, No. 13.

Sehgal et al., "CXCR-4, a chemokine receptor, is overexpressed in and required for proliferation of glioblastoma tumor cells", Journal of Surgical Oncology, 1998, pp. 99-104, vol. 69.

Sewing et al., "Human cyclin D1 encodes a labile nuclear protein whose synthesis is directly induced by growth factors and suppressed by cyclic AMP", Journal of Cell Science, 1993, pp. 545-554, vol. 104, Pt 2.

Signoret et al., "Phorbol esters and SDF-1 induce rapid endocytosis and down modulation of the chemokine receptor CXCR4", Journal of Cell Biology, 1997, pp. 651-664, vol. 139, No. 3.

Smith et al., "CXCR4 regulates growth of both primary and metastatic breast cancer", Cancer Research, 2004, pp. 8604-8612, vol. 64, No. 23.

Sotsios et al., "The CXC chemokine stromal cell-derived factor activates a Gi-coupled phosphoinositide 3-kinase in T lymphocytes" Journal of Immunology, 1999, pp. 5954-5963, vol. 163.

Staller et al., "Chemokine receptor CXCR4 downregulated by von Hippel-Lindau tumour suppressor pVHL", Nature, 2003, pp. 307-311, vol. 425, No. 6955.

Staudt et al., "Cloning of a lymphoid-specific cDNA encoding a protein binding the regulatory octamer DNA motif", Science, 1988, pp. 577-580, vol. 241.

Stewart et al., "Cranial radiation and concomitant cisplatin and mitomycin-C plus resistance modulators for malignant gliomas" Journal of Neuro-Oncology, 1997, pp. 161-168, vol. 32.

Su et al., "Inhibition of tyrosine kinase activation blocks the downregulation of CXC chemokine receptor 4 by HIV-1 gp120 in CD4+ T cells", Journal of Immunology, 1999, pp. 7128-7132, vol. 162, No. 12.

Sun et al., "Beta-arrestin2 is critically involved in CXCR4-mediated chemotaxis, and this is mediated by its enhancement of p38 MAPK activation" Journal of Biological Chemistry, 2002, pp. 49212-49219, vol. 277, No. 51.

Takeda et al., "Construction of chimaeric processed immunoglobulin genes containing mouse variable and human constant region sequences", Nature, 1985, pp. 452-445, vol. 314.

Takuma et al., "Astrocyte apoptosis: implications for neuroprotection", Progress in Neurobiology, 2004, pp. 111-127, vol. 72, No. 2.

The et al., "Rescue of a Drosophila NF1 mutant phenotype by protein kinase A", Science, 1997, pp. 791-794, vol. 276, No. 5313.

Torp et al., "Epidermal growth factor receptor expression in human gliomas", Cancer Immunology Immunotherapy, 1991, pp. 61-34, vol. 33.

Trent et al., "Lipid bilayer simulations of CXCR4 with inverse agonists and weak partial agonists", Journal of Biological Chemistry, 2003, pp. 47136-47144, vol. 278, No. 47.

Tsuchiya et al., "Caffeine-potentiated radiochemotherapy and function-saving surgery for high-grade soft tissue sarcoma", Anticancer Research, 2000, pp. 2173-2143, vol. 20.

Tuerk et al., "RNA pseudoknots that inhibit human immunodeficiency virus type 1 reverse transcriptase", Proceedings of the National Academy of Sciences USA, 1992, pp. 6988-6992, vol. 89.

Varela et al., "EGF-R and PDGF-R, but not bcl-2, overexpression predict overall survival in patients with low-grade astrocytomas", Journal of Surgical Oncology, 2004, pp. 34-40, vol. 86.

Vazquez-Prado et al., "G protein-coupled receptor cross-talk: pivotal roles of protein phosphorylation and protein-protein interactions", Cellular Signaling, 2003, pp. 549-557, vol. 15, No. 6.

Venkatesan et al., "Distinct mechanisms of agonist-induced endocytosis for human chemokine receptors CCR5 and CXCR4", Molecular Biology of the Cell, 2003, pp. 3305-3324, vol. 14, No. 8.

Vicente-Manzanares et al., "Involvement of phosphatidylinositol 3-kinase in stromal cell derived factor-1 alpha-induced lymphocyte polarization and chemotaxis", Journal of Immunology, 1999, pp. 4001-4012, vol. 163.

Wachtel et al., "Rolipram, a novel antidepressant drug, reverses the hypothermia and hypokinesia of monoamine-depleted mice by an action beyond postsynaptic monoamine receptors", Neuropharmacology, 1986, pp. 1119-1126, vol. 25, No. 10.

Wang et al., "Role of tyrosine phosphorylation in ligand-independent sequestration of CXCR4 in human primary monocytes-macrophages", Journal of Biological Chemistry, 2001, pp. 49236-49243, vol. 276, No. 52.

Warrington et al., "Spatiotemporal differences in CXCL12 expression and cyclic AMP underlie the unique pattern of optic glioma growth in neurofibromatosis type 1", Cancer Research, 2007, pp. 8588-8595, vol. 67. No. 18.

Watanabe et al., "Role of gemistocytes in astrocytoma progression", Laboratory Investigation, 1997, pp. 277-284, vol. 76, No. 2.

Weissinger et al., "Activation of protein kinase A (PKA) by 8-CI-cAMP as a novel approach for antileukaemic therapy", British Journal of Cancer, 2004, pp. 186-192, vol. 91.

Winter et al., "Man-made antibodies", Nature, 1991, pp. 293-299, vol. 349.

Woerner et al., "Widespread CXCR4 activation in astrocytomas revealed by phospho-CXCR4-specific antibodies", Cancer Research, 2005, pp. 11392-11399, vol. 65, No. 24.

Xu et al., "The neurofibromatosis type 1 gene encodes a protein related to GAP", Cell, 1990, pp. 599-608, vol. 62, No. 3.

Yang et al., "Neurofibromin-deficient Schwann cells secrete a potent migratory stimulus for Nf1+/- mast cells", Journal of Clinical Investigation, 2003, pp. 1851-1861, vol. 112, No. 12.

Yang et al., "Blocking CXCR4-mediated cyclic AMP suppression inhibits brain tumor growth in vivo", Cancer Research, 2007, pp. 651-658, vol. 67, No. 2.

Yu et al., "Structural basis for the binding of proline-rich peptides to SH3 domains", Cell, 1994, pp. 933-945, vol. 76.

Zhang et al., "The chemokine stromal cell derived factor-1 (CXCL12) promotes glioma invasiveness through MT2-matrix metalloproteinase", Carcinogenesis, 2005, pp. 2069-2077, vol. 26, No. 12.

Zhang et al., "A point mutation that confers constitutive activity to CXCR4 reveals that T140 is an inverse agonist and that AMD3100 and ALX40-4C are weak partial agonists", Journal of Biological Chemistry, 2002, pp. 24515-24521, vol. 277, No. 27.

Zhou et al., "CXCR4 is a major chemokine receptor on glioma cells and mediates their survival", Journal of Biological Chemistry, 2002, pp. 49481-49487, vol. 277, No. 51.

Zhu et al., "Inactivation of NF1 in CNS causes increased glial progenitor proliferation and optic glioma formation", Development and Disease, 2005, pp. 5577-5588, vol. 132, No. 24.

Zlotnick, "Chemokines in neoplastic progression", Seminars in Cancer Biology, 2004, pp. 181-185, vol. 14.

Figure 14C
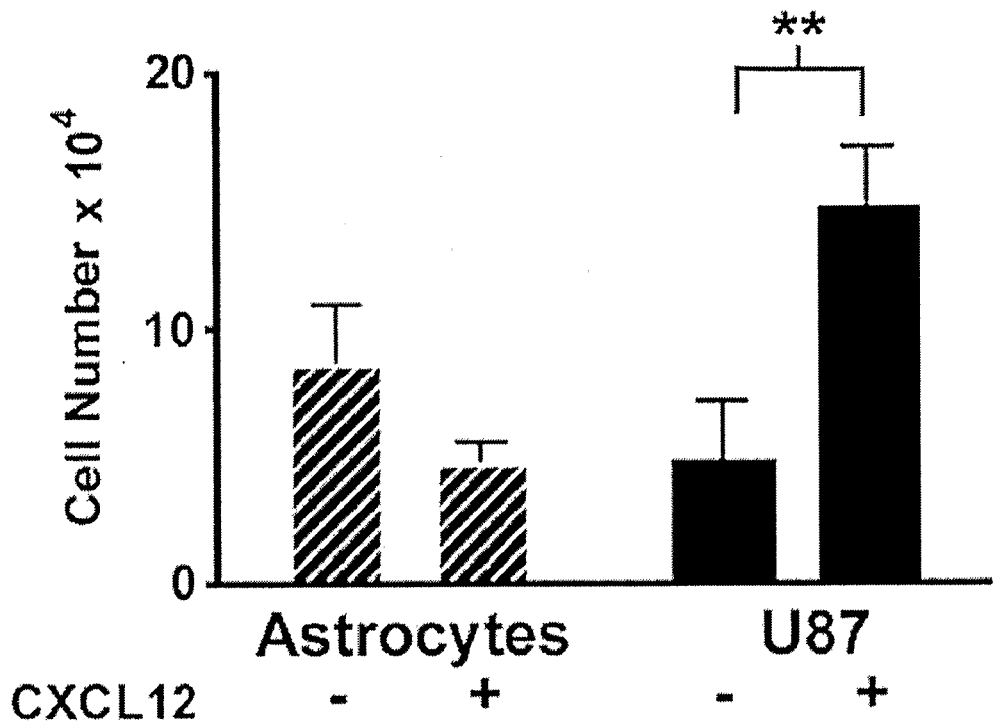
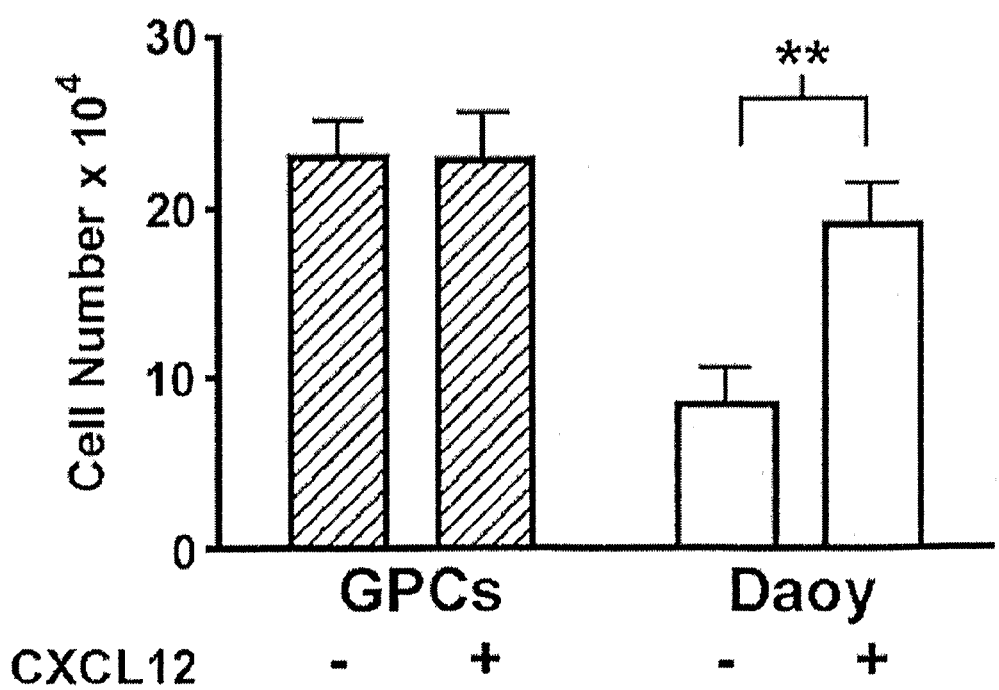
Figure 14D

Figure 21

| Grade | CXCL12* | CXCR4† | pCXCR4 | pCXCR4/CXCR4 |
|---|---|---|---|---|
| 1 (n = 7) | | | | |
| Range | 1-3 | 2-4 | 1-3 | 0.25-1.5 |
| Mean ± SE | 1.57 ± 0.3 | 3.29 ± 0.29 | 2.29 ± 0.29 | 0.76 ± 0.15 |
| 2 (n = 5) | | | | |
| Range | 1-4 | 0-4 | 1-4 | 0.5-2 |
| Mean ± SE | 2 ± 0.55 | 2.2 ± 0.8 | 2.2 ± 0.49 | 1.13 ± 0.28 |
| 3 (n = 8) | | | | |
| Range | 1-3 | 1-4 | 1-4 | 0.5-2 |
| Mean ± SE | 1.88 ± 0.35 | 2.63 ± 0.38 | 2.63 ± 0.38 | 1.08 ± 0.17 |
| 4 (n = 8) | | | | |
| Range | 1-2 | 2-3 | 1-3 | 0.5-1.5 |
| Mean ± SE | 1.5 ± 0.19 | 2.25 ± 0.16 | 2.14 ± 0.24 | 1.0 ± 0.13 |

SEQUENCE LISTING

<160> NUMBER OF SEQ ID NOS: 1

<210> SEQ ID NO 1
<211> LENGTH: 15
<212> TYPE: PRT
<213> ORGANISM: Homo sapiens

```
<400> SEQUENCE: 1

Gly Lys Arg Gly Gly His Ser Ser Val Ser Thr Glu Ser Glu Ser
1               5                   10                  15
```

US 7,892,767 B2

PHOSPHOSPECIFIC CHEMOKINE RECEPTOR ANTIBODIES

FIELD OF THE INVENTION

The present invention generally relates to chemokine receptor antibodies that selectively bind to an activated form of the receptor but not to a non activated form of the receptor. In particular, the current invention provides phosphospecific chemokine receptor antibodies.

BACKGROUND OF THE INVENTION

Identification of novel therapeutic targets is critical to the advancement of cancer treatment. Currently, systemic cancer treatment regimes involve administering one or more highly toxic chemotherapeutics or hormonal therapies to the patient after the cancer has progressed to a point where the therapeutic benefits of chemotherapy/hormonal therapies outweigh its serious side effects. As a consequence of these side effects, standard chemotherapeutics are typically used only for short periods of time, often alternating chemotherapy with periods off treatment, so as not to overwhelm the patient with drug side effects. Accordingly, given the risk-benefit trade-off, side effects typically preclude starting chemotherapy when patients exhibit precancerous lesions, or continuing chemotherapy or hormonal therapy on a chronic basis after cancer has been eliminated in an attempt to prevent its re-occurrence.

Cancer and precancer research is replete with publications that describe various biochemical molecules that are over-expressed in neoplastic tissue, leading several groups to research whether specific over-expressed molecules are responsible for the disease, and whether, if such over-expression were inhibited, neoplasia could be alleviated. One group of such biochemical molecules that have been extensively studied as potential therapeutic targets for neoplasia treatments are the chemokines and their receptors. Chemokines constitute a family of small molecular weight cytokines that induce migration and activation of leukocytes and are necessary for the normal development of multiple tissues. These molecules are ligands for seven-transmembrane G protein linked receptors that induce a wide array of signaling cascades, productive of different cell type-specific responses. Thirteen different human chemokine receptors are known, including CCR1, CCR2, CCR3, CCR4, CCR5, CCR6, CCR7, CCR8, CXCR1, CXCR2, CXCR3, CXCR4, and CCX-CKR2.

Binding of a chemokine to its receptor typically induces normal intracellular signaling responses such as a transient rise in cytosolic calcium concentration, followed by cellular biological responses such as chemotaxis. But over expression or aberrant activation of chemokines and their receptors, as detailed above, has been linked to cancer cell growth and spread. The chemokine receptor CXCR4, for example, is expressed in as many as 23 different tumor types, and is a particularly exciting new target for cancer therapy (1). Most models of CXCR4 function in cancer focus on its potential role as a mediator of motility, invasiveness and metastatic behavior (2). CXCR4 activation however, is also necessary for growth in intracranial models of primary brain tumors (3) as well as in models of primary breast cancer (4). The growth effects of CXCR4 activation are reminiscent of its role in normal hematopoiesis (5-7) or in cerebellar (8), hippocampal (9, 10) and retinal development (11). In all cases, CXCR4 activity is presumed to be ligand dependent. These studies suggested that cooperative signaling between CXCR4 and pathways that are activated by oncogenetic changes may be essential for tumor growth.

Despite advances in the field, the identification of new target molecules useful in the diagnosis and treatment of cancer and other diseases is a continuing need. In addition, methods for evaluating the role that target molecules play in cancer are also needed.

SUMMARY OF THE INVENTION

Among the several aspects of the invention, therefore, is the provision of chemokine receptor antibodies that may be utilized as a tool to monitor the activity of chemokine receptors. The antibodies selectively bind to an activated form of the chemokine receptor. Activation of CXCR4 is known to be associated with the growth and spread of several cancers. Because the antibodies of the current invention selectively recognize the activated form of CXCR4, for example, they may be utilized in methods for diagnosing disorders associated with increased CXCR4 activation, such as cancer, in methods for monitoring the effectiveness of a therapy for a disorder related to CXCR4 activation, and in methods for screening compounds that prevent CXCR4 activation.

Other aspects and features of the invention are described in more detail herein.

presents photographic images showing that P339-CXCR4 labeling (red insets) of gemistocytes was abolished by incubation of tissue sections with 8000 units/ml lambda phosphatase. Total CXCR4 (green insets) labeling was unaffected by this treatment. The merged phospho-CXCR4 (red) and total CXCR4 (green) appears yellow. Phospho-CXCR4 staining reveals a punctuate pattern in an apparent membranous and cytoplasmic distribution. Nuclei are counterstained with DAPI (blue). Scale bar is equal to 5 µm.

FIG. 3 depicts a series of images demonstrating that P339-CXCR4, but not P338-CXCR4 antibodies recognize a CXCL12 induced form of CXCR4. (A) depicts an image of a western blot analysis of LN428 GBM cells treated with CXCL12 for 0 or 10 minutes as indicated. P339- but not P338-CXCR4 antibody recognizes a CXCL12 induced change in the receptor. Blots were stripped and reprobed with CXCR4 antibody as a loading control. (B) depicts a photographic image showing that LN428 GBM cells were exposed to 1 µg/ml CXCL12 for 0 or 10 minutes. Samples were fixed at t=0, t=10 and t=30 minutes. The latter sample was incubated for an additional 20 minutes after CXCL12 washout. Fixed cells were labeled with P339-CXCR4 antibody. Staining increased after 10 minutes of CXCL12 exposure. Twenty minutes after CXCL12 wash-out, at t=30 minutes, surface labeling was diminished and P339-CXCR4 accumulated intracellularly. (C) depicts images from representative sections of two areas of human hypothalamus (HPT a and HPT b) demonstrating the P339-CXCR4 labeling only occurs when CXCR4 is located near a source of CXCL12. The sections were stained with CXCL12, CXCR4, and P339-CXCR4 antibodies. Bar, 20 µm. (D) depicts an image of a western blot analysis showing P339-CXCR4 phosphorylation increased after treatment with PMA or EGF. CXCL12 (L12) was included for comparison. Untreated cells serve as a control (con).

Figure 4:
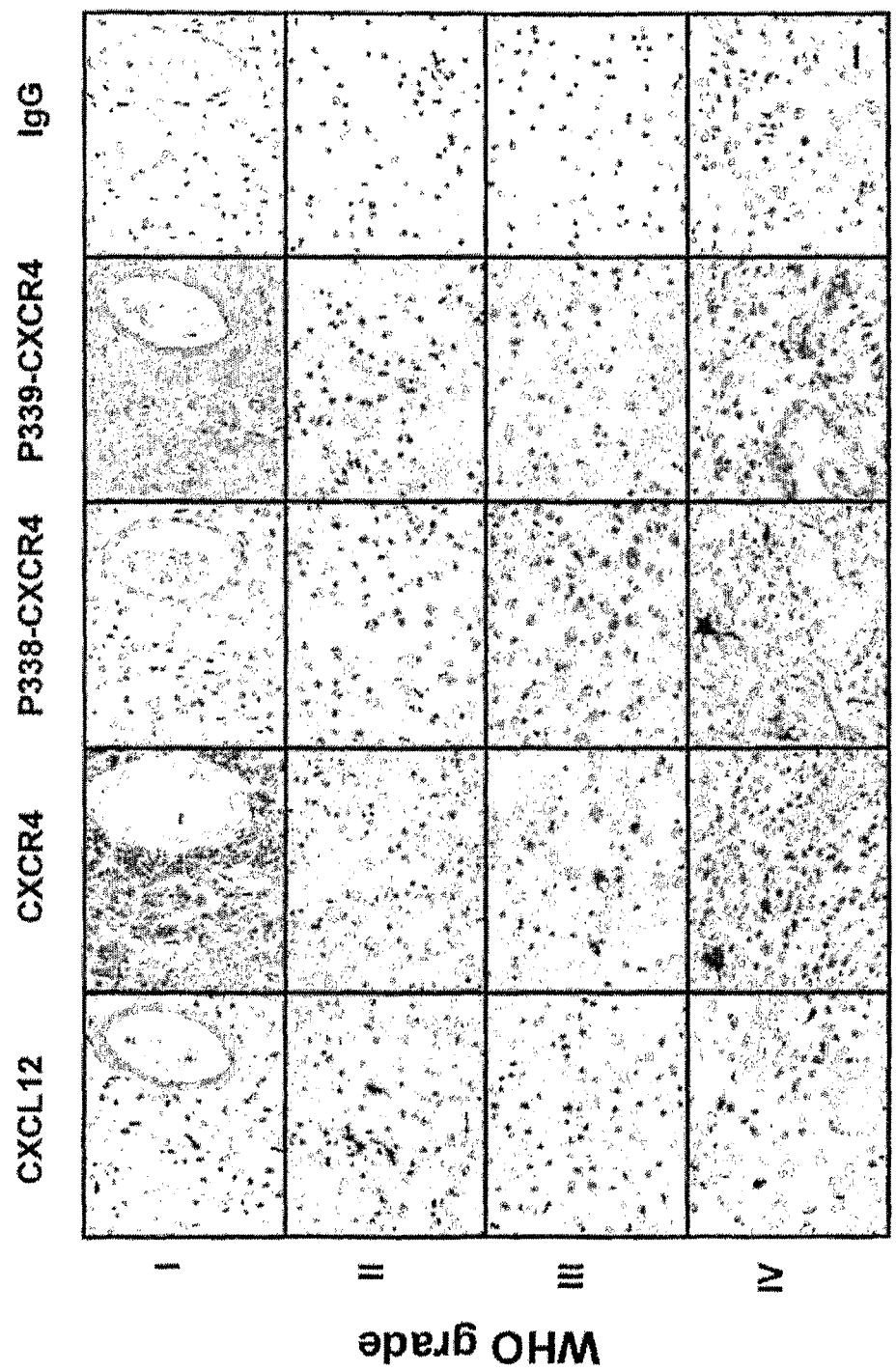

FIG. 4 depicts a series of photographic images showing CXCL12, CXCR4 and phospho-CXCR4 staining in grade I through grade IV astrocytomas. Positive staining appears brown. Scale bar=20 µm.

Figure 5:
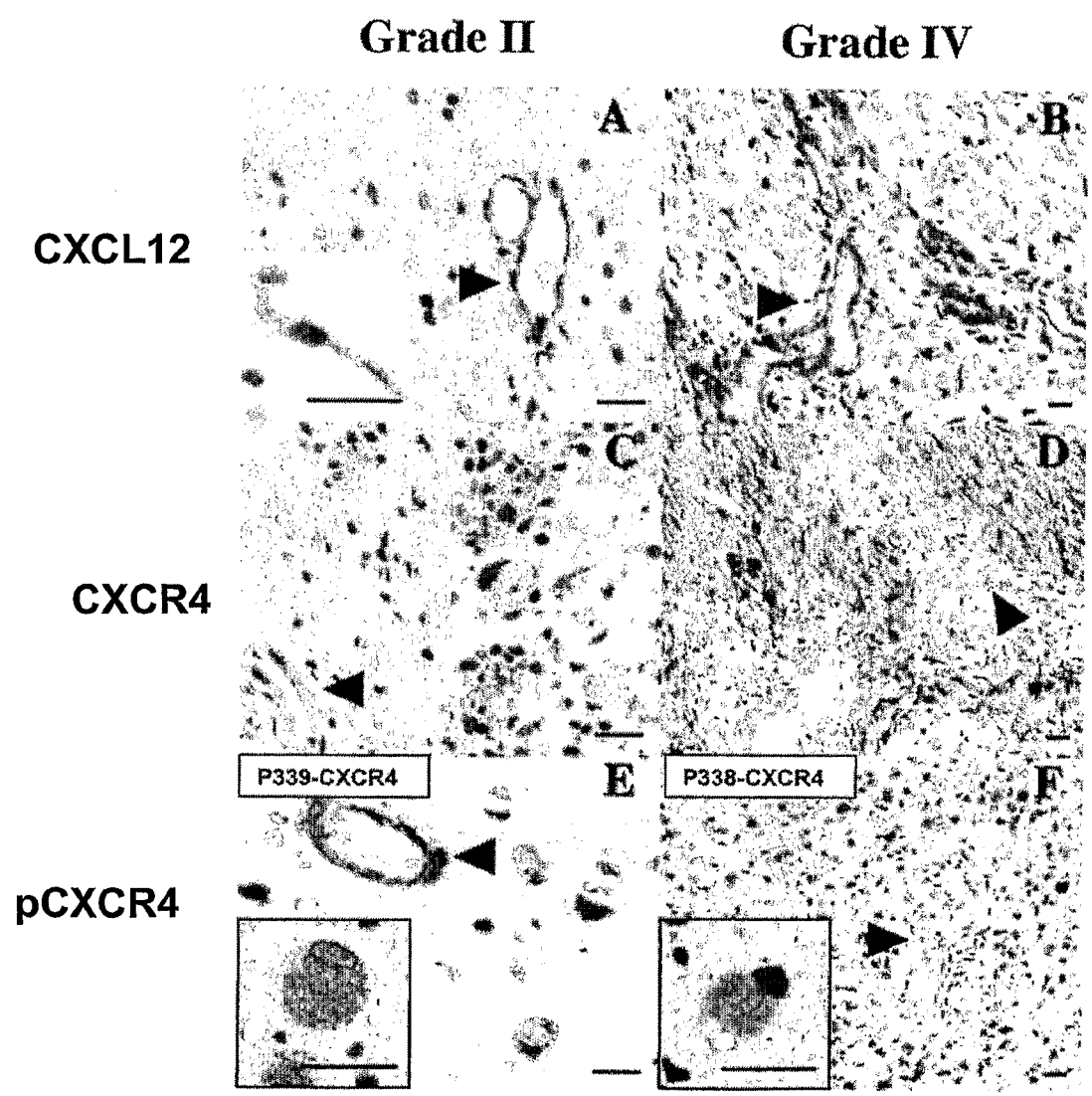

FIG. 5 depicts a series of photographic images showing that human astrocytomas of all grades exhibit pCXCR4 labeling. Representative sections from Grade II and Grade IV astrocytomas stained for CXCL12 (A and B), CXCR4 (C and D), P339-CXCR4 (E) and P338-CXCR4 (F). CXCL12 was present in endothelial cells in all grades of astrocytoma (A, arrowhead). A glomeruloid tuft of endothelial cells in the Grade IV sample exhibited intense CXCL12 staining (B, arrowhead). In addition, infiltrating microglia (A, inset) express CXCL12. CXCR4 is present in tumor cells and endothelial cells (arrowheads) in astrocytomas, regardless of grade (C and D). Two images are presented in panel (C) to better highlight the endothelial and tumor cell staining. P339-CXCR4 antibody labeled endothelial cells (arrowhead) and tumor cells (E). Gemistocytes (E, inset) stained strongly. P338-CXCR4 antibody stained tumor cells (F) but not endothelial cells (F, arrowhead). Gemistocytes were strongly immunoreactive (F, inset). Scale bars equal 20 µm.

Figure 6:
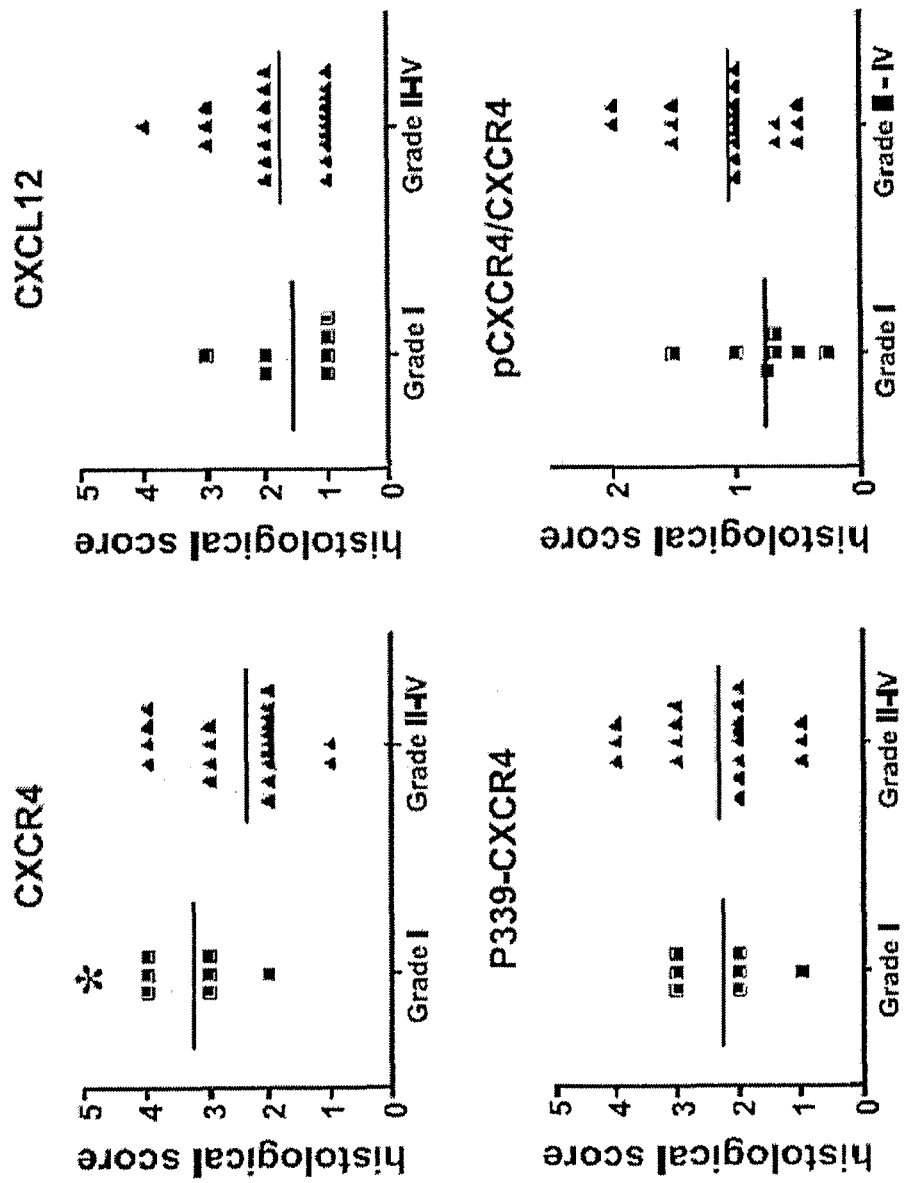

FIG. 6 depicts graphs comparing grade 1 versus grades 2 to 4 astrocytoma staining scores. Scatter plots of grade 1 or grades 2 to 4 tumor CXCL12, CXCR4, and P339-CXCR4 staining scores and the ratio of P339-CXCR4 to CXCR4 (pCXCR4/CXCR4). Horizontal lines, mean. Ratio of pCXCR4 to CXCR4 was calculated for each tumor. Scatter plot of individual tumor values. *, $P<0.05$, two-tailed t test.

Figure 7:
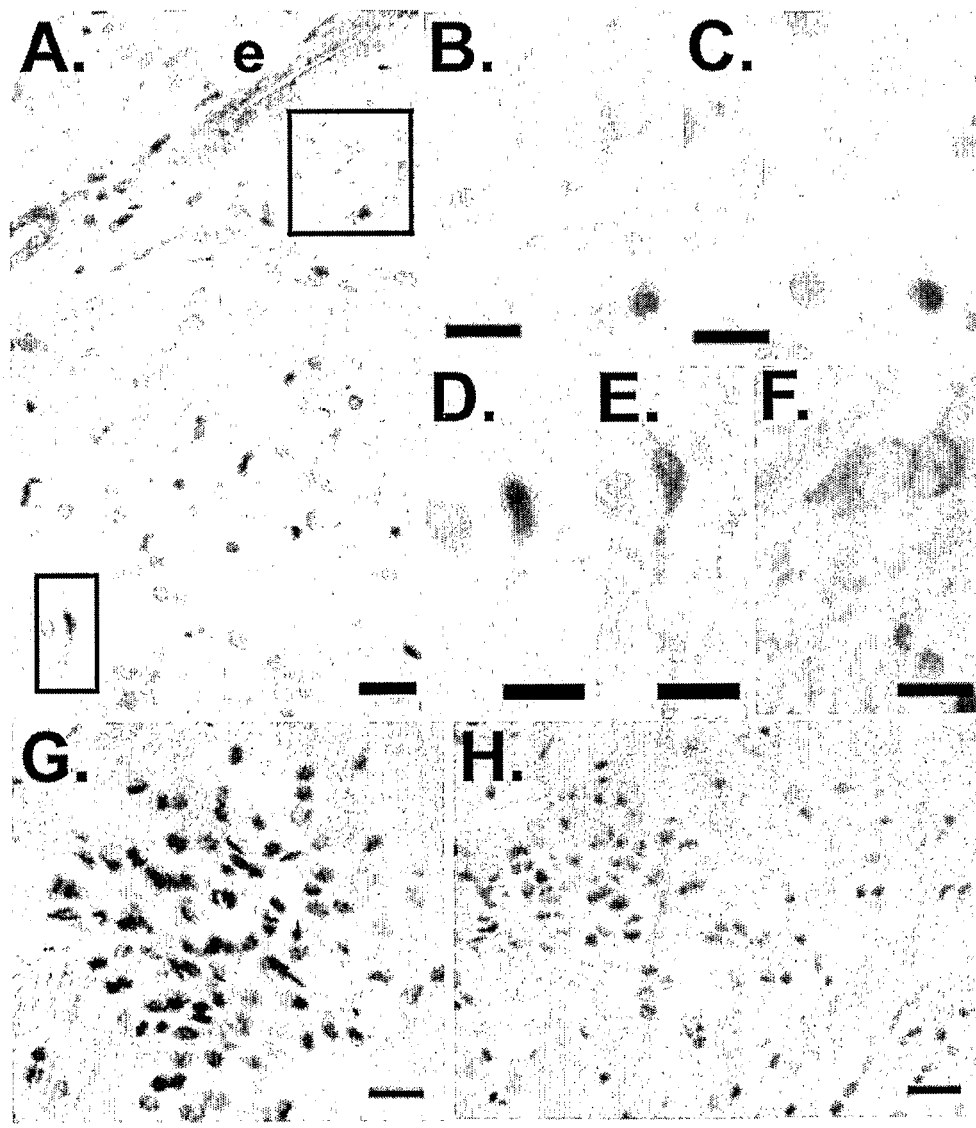

FIG. 7 depicts a series of images illustrating that NF1-associated optic pathway gliomas exhibit paracrine activation of CXCR4. (A) Representative NF1 optic pathway glioma with typical histology was stained for CXCL12. Positive staining appears brown. Vascular endothelium (e), cellular processes (top inset) and cells with typical morphology of microglia (bottom inset) all express CXCL12. Control IgG sections were negative (data not shown). (B) Top inset from (A) at higher magnification. (C) The same tumor was stained for neurofilament 160. (D) Bottom inset from (A) at higher magnification. (E) The same tumor was stained for CD68. (F) Tumor cells express CXCR4 in a phosphorylated, activated form (pCXCR4). (G) CXCL12 expression in an optic pathway tumor from a representative Nf1+/−$^{GFAP}$CKO mouse. (H) CXCL12 expression in an optic pathway tumor from a representative Nf1+/−; K-RAS$^{GFAP}$ mouse. Scale bar for (A)=20 µm, (B–F)=10 µm and for (G,H)=20 µm.

Figure 8:
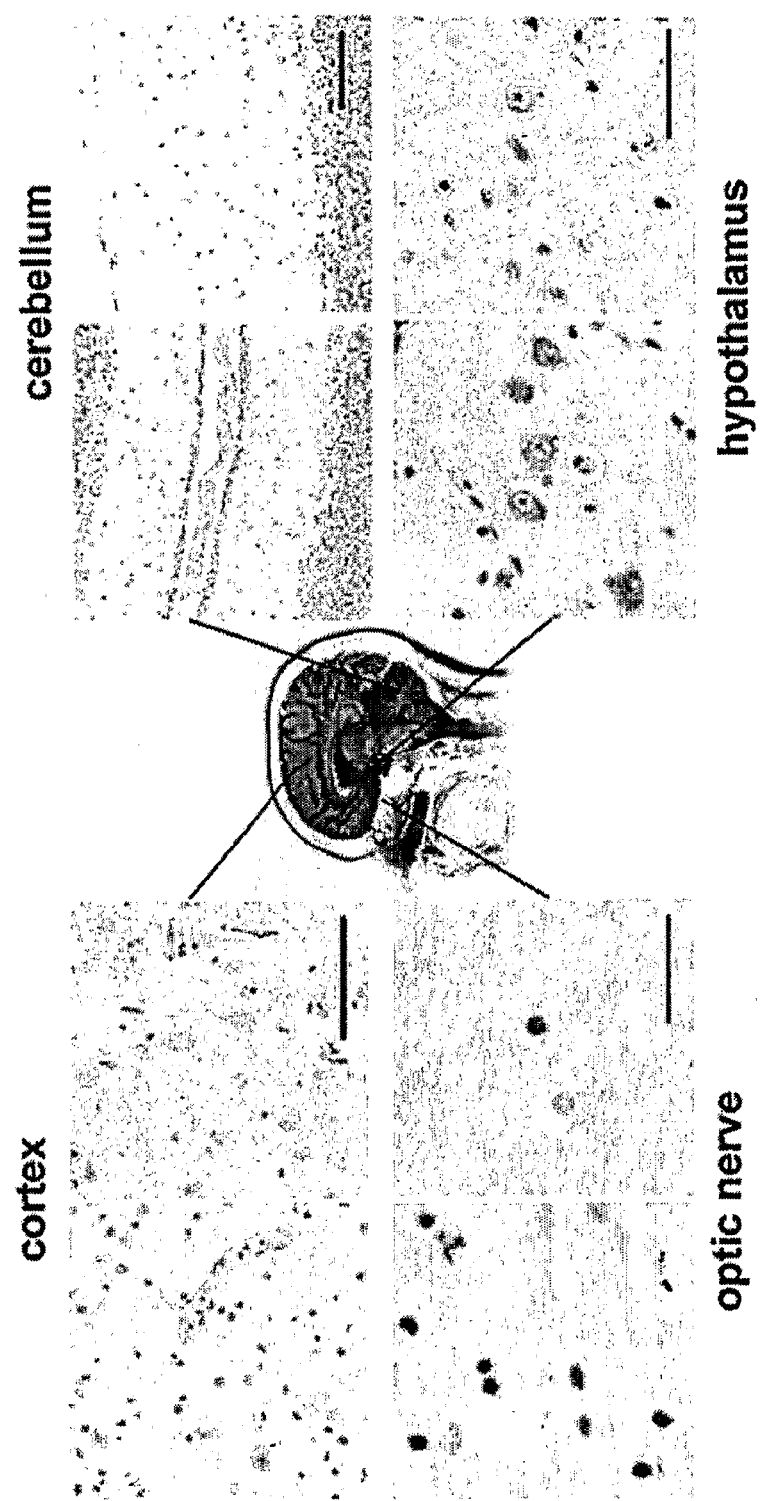

FIG. 8 depicts a series of images demonstrating that CXCL12 expression in human and mouse brains is developmentally regulated. Sections from autopsy brains of children less than 1 year of age (left hand panels) and 11 or 12 years of age (right hand panels) from cortex, cerebellum, optic nerve and hypothalamus were stained for CXCL12. In all cases, staining appears brown. Scale bars=100 µm.

Figure 9:
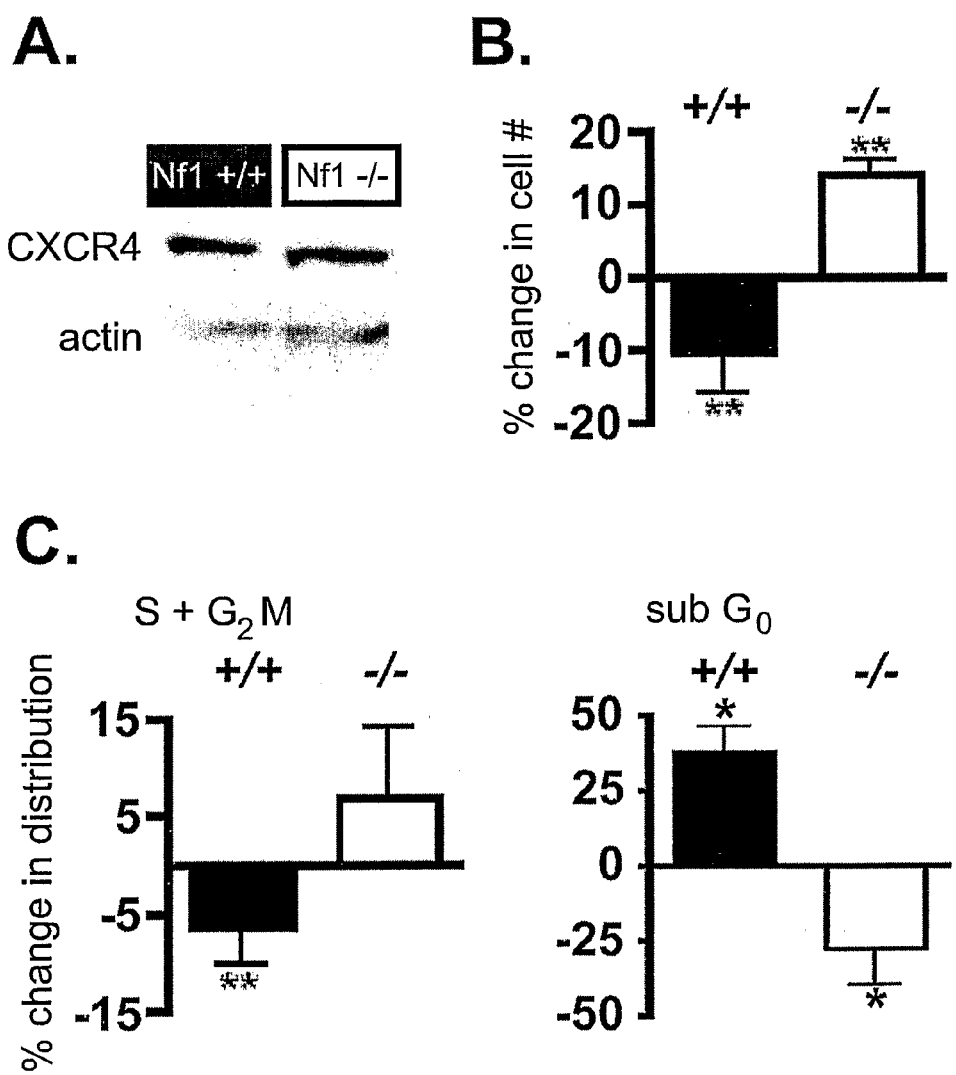

FIG. 9 depicts a series of graphs and images showing that CXCL12 promotes the growth of Nf1−/− but not Nf1+/+ astrocytes by decreasing apoptosis. Primary cultures of Nf1+/+ and Nf1−/− astrocytes were prepared as described in the materials and methods section for experiments 5-10. (A) Nf1+/+ and Nf1−/− astrocytes express comparable levels of CXCR4 as determined by western blot analysis. β-actin serves as loading control. (B) CXCL12 growth effects on Nf1+/+(filled bars, +/+) and Nf1−/− (open bars, −/−) astrocytes. (C) The contribution of changes in proliferation (S+G$_2$-M) and apoptosis (Sub-G$_0$) to changes in cell number was assessed by flow cytometry. Presented in panels B and C are the means and standard errors of the means of three separate experiments, each done in duplicate. Significance for all experiments was determined by two-tailed T-test and *=P<0.05 and **=P<0.005.

Figure 10:
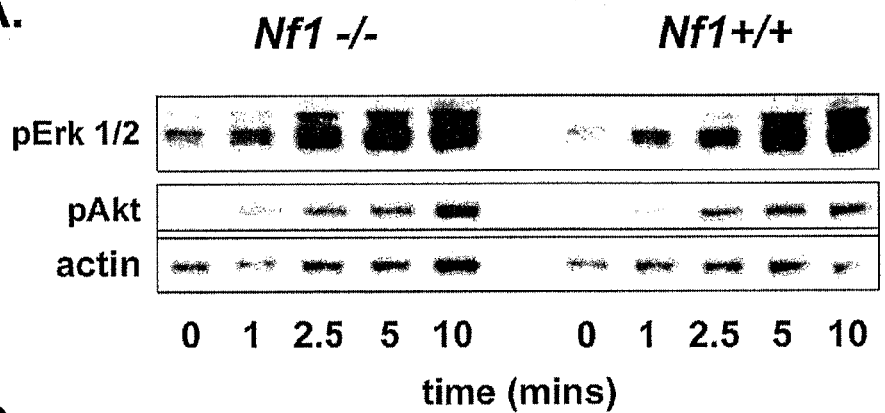
Figure 10:
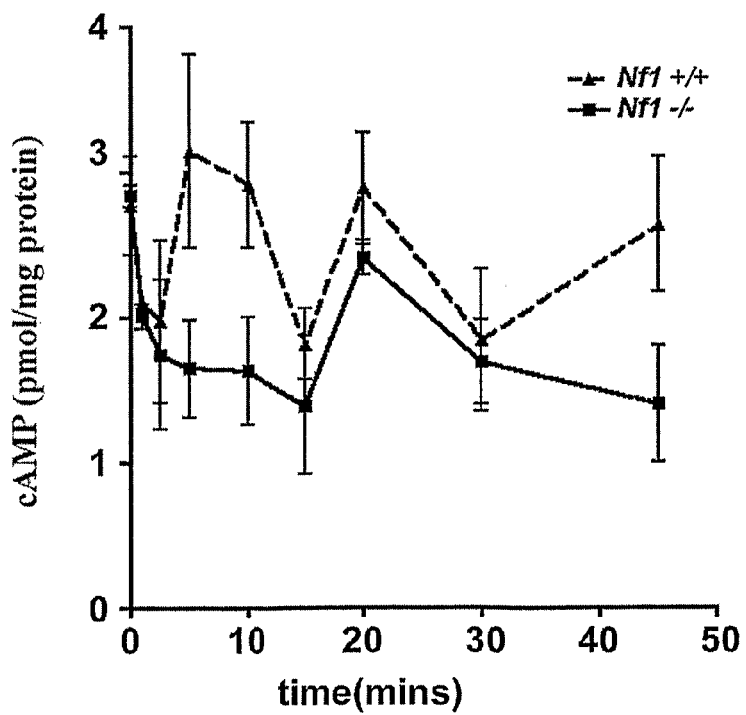

FIG. 10 depicts a graph and western blot image illustrating that loss of neurofibromin is associated with a change in cAMP responses to CXCL12. (A) Time dependent changes in Erk ½ and Akt phosphorylation as a function of CXCL12 treatment (0.1 µg/ml) were determined by western blot. β-actin serves as loading control. (B) Time dependent changes in intracellular cAMP levels in Nf1+/+ (dashed line) and Nf1−/− (solid line) astrocytes treated with CXCL12 (0.1 µg/ml) were measured by ELISA. Presented are the means and standard errors of the means of three separate experiments, each done in duplicate. The difference between the curves has a p-value of <0.005 as established by two-way ANOVA.

Figure 11:
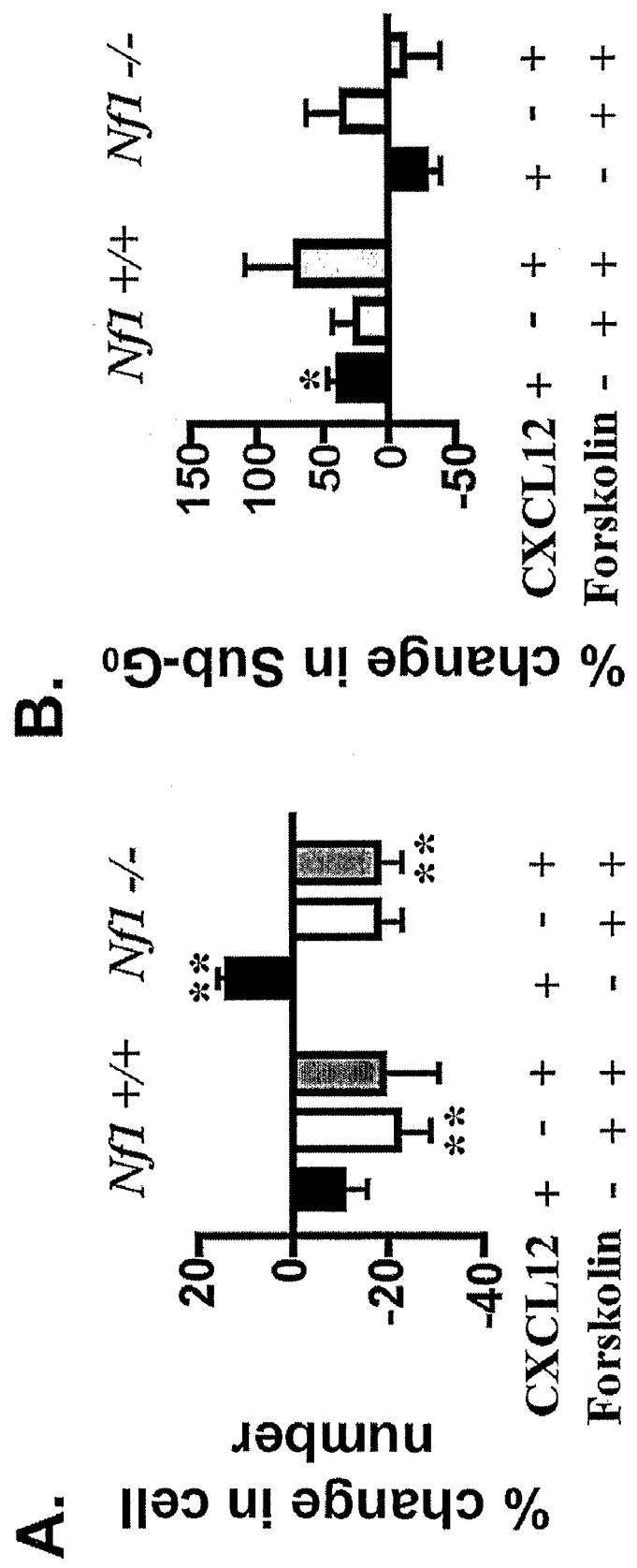

FIG. 11 depicts graphs demonstrating that the growth effects of CXCL12 are dependent upon decreases in cAMP. Nf1+/+ and Nf1−/− astrocytes were cultured in the presence or absence of CXCL12 (0.1 µg/ml) and forskolin (10 µM). (A) Cell number was determined by trypan blue exclusion. (B) Apoptotic fraction (Sub-G$_o$ fraction) was measured by flow cytometry. Presented are the means and standard errors of the means of five separate experiments, each done in duplicate. Significance was determined by two-tailed T-test and *=p<0.05 and **=p<0.005.

Figure 12:
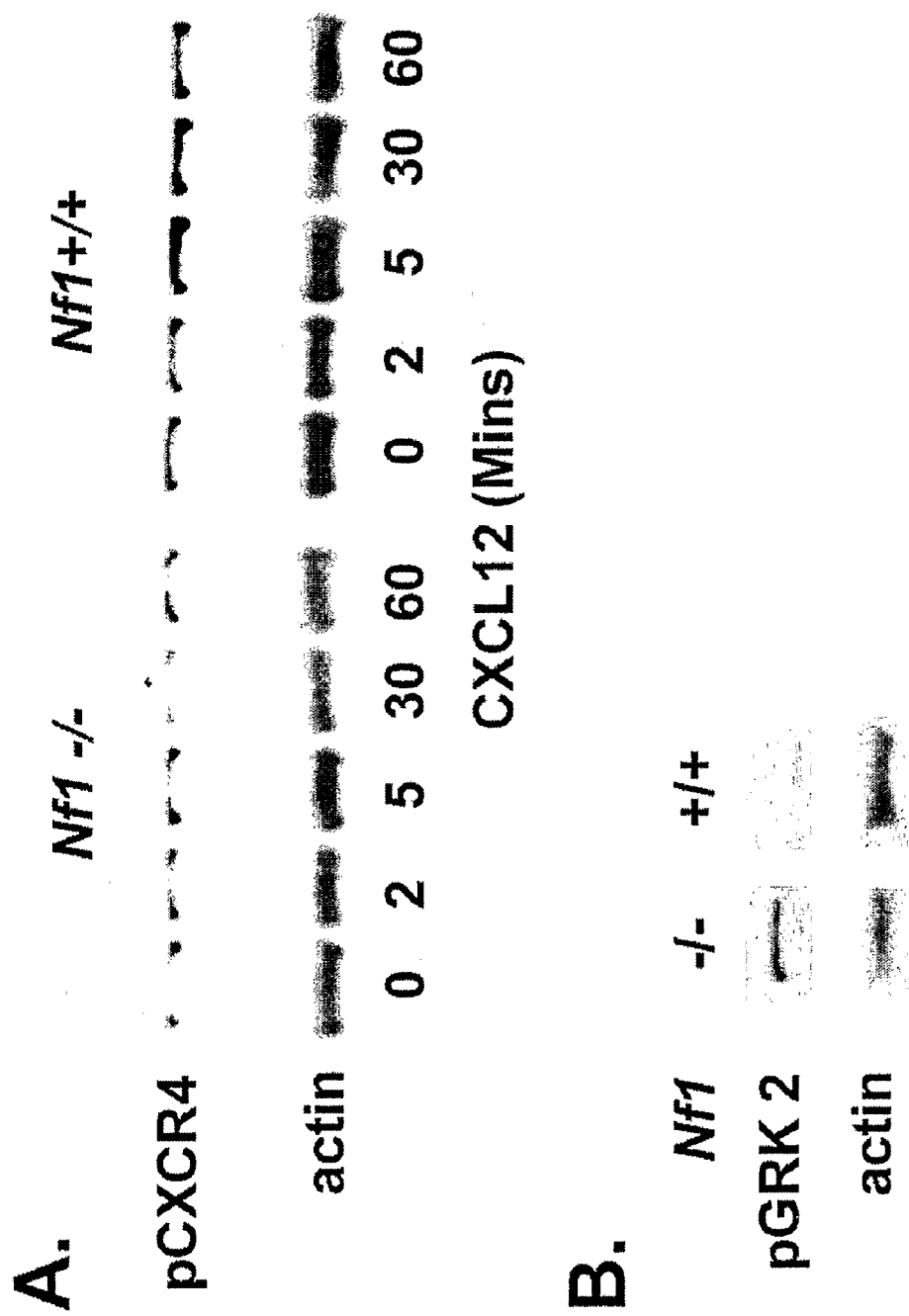

FIG. 12 depicts images of Western blots showing that neurofibromin loss inhibits CXCR4 phosphorylation via MEK-dependent phosphorylation of GRK2. (A) CXCR4 phosphorylation (pCXCR4) was measured by western blot analysis in primary cultures of Nf1−/− and Nf1+/+ astrocytes treated with CXCL12 (0.1 µg/ml) for times indicated. β-actin serves as loading control. (B) Level of GRK2 phosphorylation was measured by western blot analysis in primary cultures of Nf1−/− and Nf1+/+ astrocytes. β-actin serves as loading control.

Figure 13:
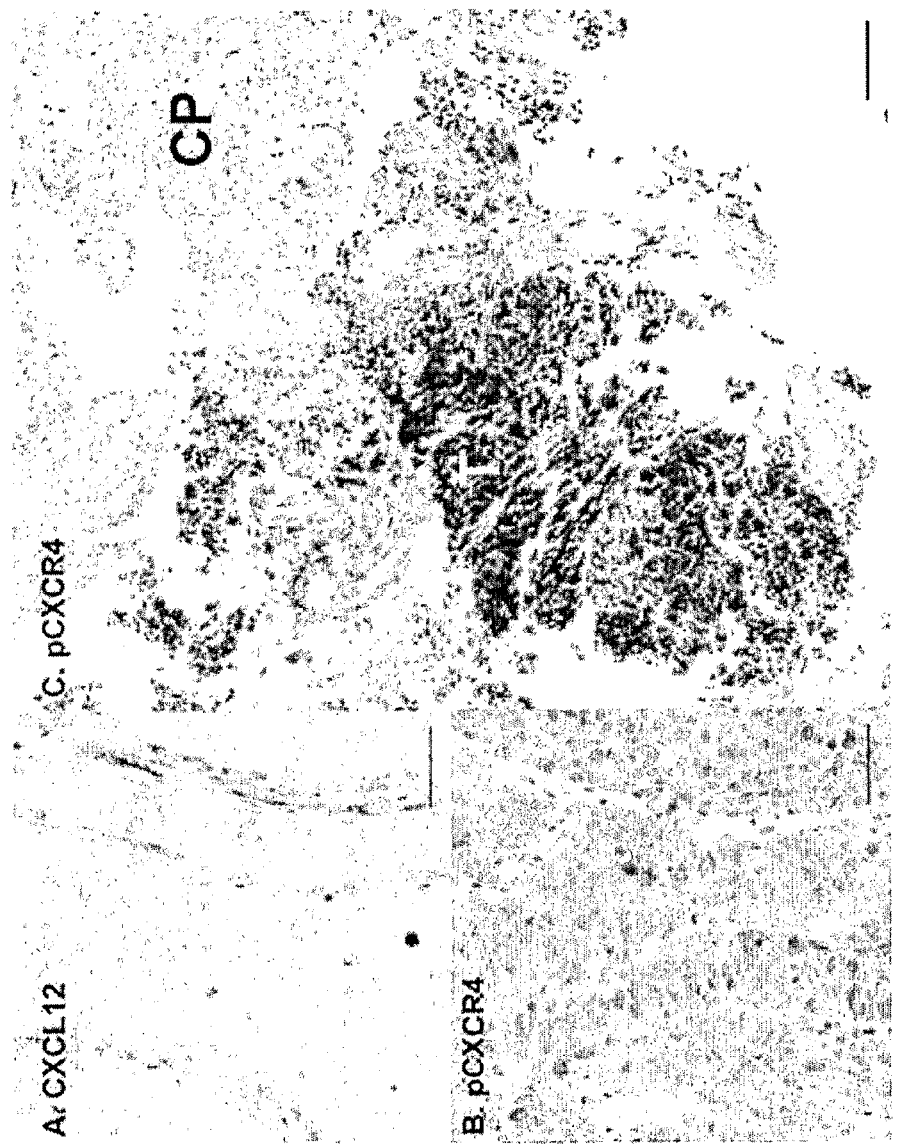

FIG. 13 depicts images showing that co-localization of CXCL12 and CXCR4 results in receptor activation in medulloblastoma. (A) CXCL12 is localized (brown staining) primarily to vascular endothelium in medulloblastoma. (B) CXCR4 is present in tumor cells in a phosphorylated form (pCXCR4, brown staining). (C) Phosphorylated CXCR4 distinguishes tumor tissue (T) from normal choroid plexus (CP). Scale bars=50 microns in (A) and (B) and 100 microns in (C).

FIG. 14 depicts a series of graphs demonstrating that CXCR4-mediated cAMP suppression is sustained and associated with growth in brain tumor cells, but not in normal counterparts. (A) Primary cultures of cortical astrocytes and cultures of U87 glioblastoma cells or (B) primary cultures of GPCs and cultures of Daoy medulloblastoma cells, were treated with CXCL12 (1 µg/ml), and cAMP was measured by ELISA at various time points as indicated. Presented are the means and SEM of three separate experiments. P<0.0005 (A) and p<0.005 (B) for the differences between the curves as determined by two-way ANOVA. (C) Primary cultures of astrocytes and U87 cultures, or (D) primary cultures of GPCs and Daoy cells, were treated with CXCL12 (1 µg/ml) and cell number was measured 24 hours later by trypan blue exclusion. Shown are the means and SEM of representative experiments done in triplicate. Each experiment was performed a total of three times with similar results. **=p<0.005 as determined by two-tailed t-test.

FIG. 15 depicts a series of graphs showing that blocking CXCR4-mediated cAMP suppression blocks CXCL12 growth effects in vitro. U87 and Daoy cell cultures were treated with CXCL12 (1 µg/ml) in the presence or absence of (A) Rolipram (200 µM) or (B) Forskolin (10 µM). Viable cell number was determined by trypan blue exclusion and cAMP was determined in parallel by ELISA. Each experiment was done at least three times in triplicate. (C) cAMP levels were determined by ELISA. The means, and SEM, of representative cell counts, as well as representative cAMP values that were determined in parallel, are shown. *=p<0.05 and **=p<0.005 as determined by two-tailed t-test.

FIG. 16 depicts graphs showing that AMD 3465 blocks CXCR4-mediated growth in vitro and in vivo. (A) U87 glioblastoma cells and Daoy medulloblastoma cells were grown in serum-free media supplemented with CXCL12 (1 µg/ml), AMD 3465 (2.5 µg/ml) or CXCL12 plus AMD 3465 as indicated. After 48 hours in culture viable cell number was determined by trypan blue exclusion. Each experiment was done at least three times in triplicate. The means and s.e.m. of representative experiments are shown. **=p<0.005 as determined by twotailed t-test (B) Intracranial xenografts of luciferase expressing U87 and Daoy were established as described. Treatment with AMD 3465 or PBS (control) was initiated at week 2 (arrow). Tumor associated bioluminescence was quantified weekly. Relative bioluminescence refers to bioluminescence normalized to the values at week 2. *=p<0.05 as determined by two-way ANOVA.

Figure 17A:
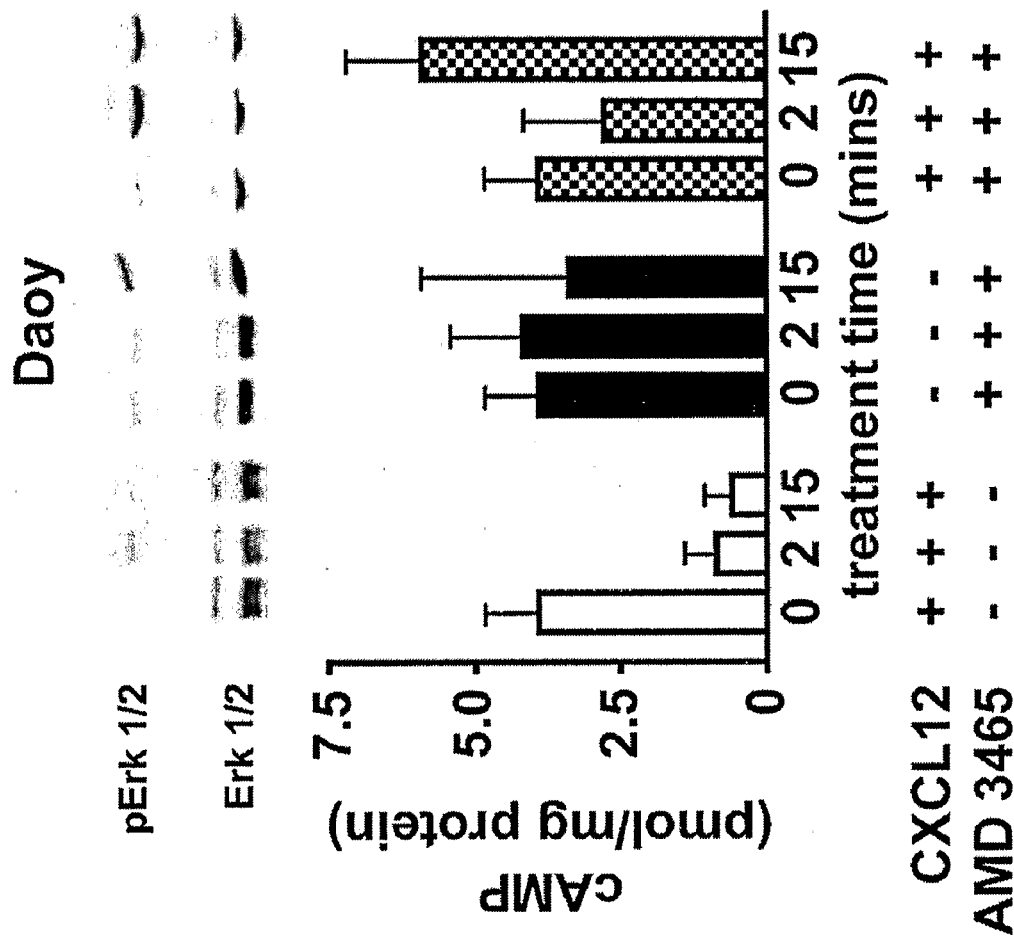
Figure 17B:
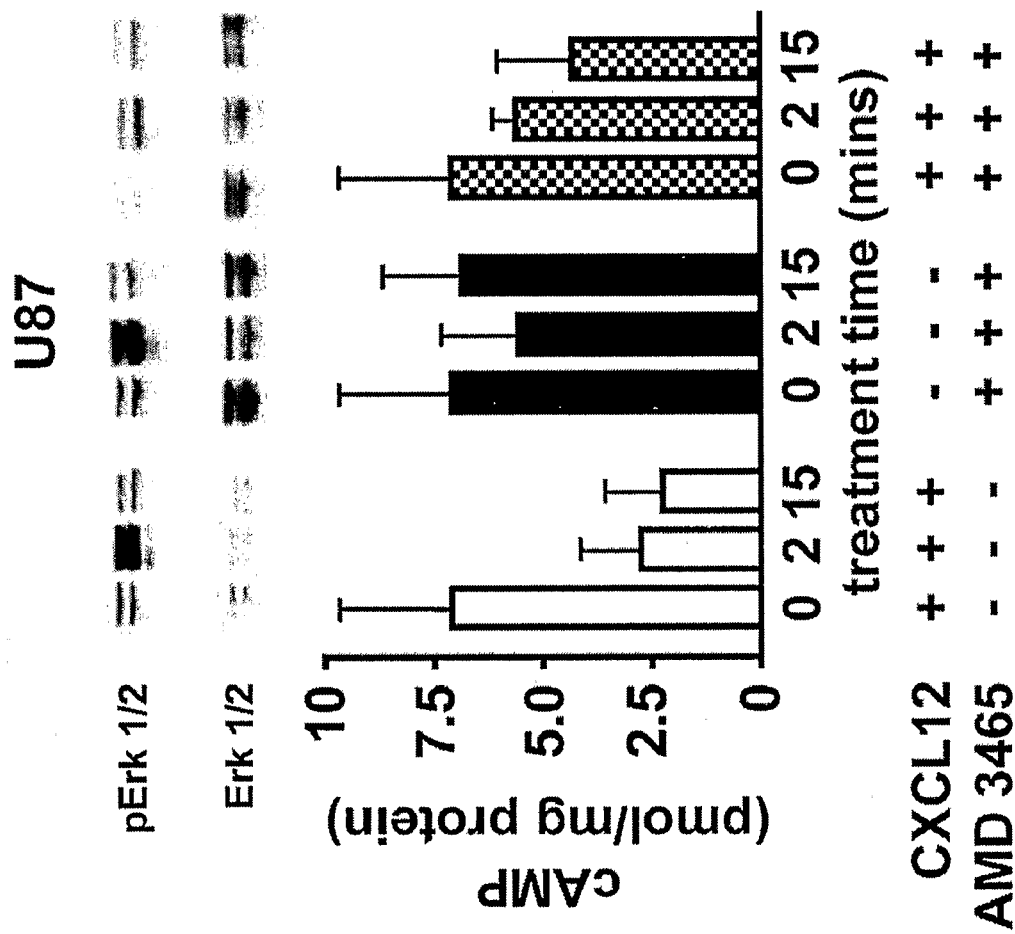

FIG. 17 depicts a series of graphs and Western blots illustrating that AMD 3465 blocks CXCR4-mediated cAMP suppression. (A) U87 and (B) Daoy cultures were treated with 1 µg/ml CXCL12, 2.5 µg/ml AMD 3465 or both agents together, for indicated time points. Activation of Erk ½ was determined by western blot analysis utilizing phospho-Erk ½ (pErk ½) specific antibodies. Total Erk ½ labeling served as loading control. Cyclic AMP was determined by ELISA in parallel cultures. Presented are means and s.e.m. of three separate experiments.

FIG. 18 depicts two graphs illustrating that overexpression of PDE4A abrogates CXCL12 growth effects. (A) U87 and (B) Daoy cells were transfected with a plasmid encoding PDE4A under control of a tet-off regulatory element (control) or co-transfected with the plasmids encoding PDE4A and the tet-off transactivator (PDE4A-expressing). Cultures were treated with CXCL12 (1 µg/ml), AMD 3465 (2.5 µg/ml) and Rolipram (200 µM) as indicated, and viable cell number was determined by trypan blue exclusion. Cyclic AMP was measured in parallel cultures by ELISA. Each experiment was performed at least 3 times. The means, and SEM, of representative cell counts, as well as representative cAMP values that were determined in parallel, are shown. *=p<0.05 and **=p<0.005 for cell counts compared to control cultures in the absence of CXCL12, as determined by two-tailed t-test.

Figure 19A:
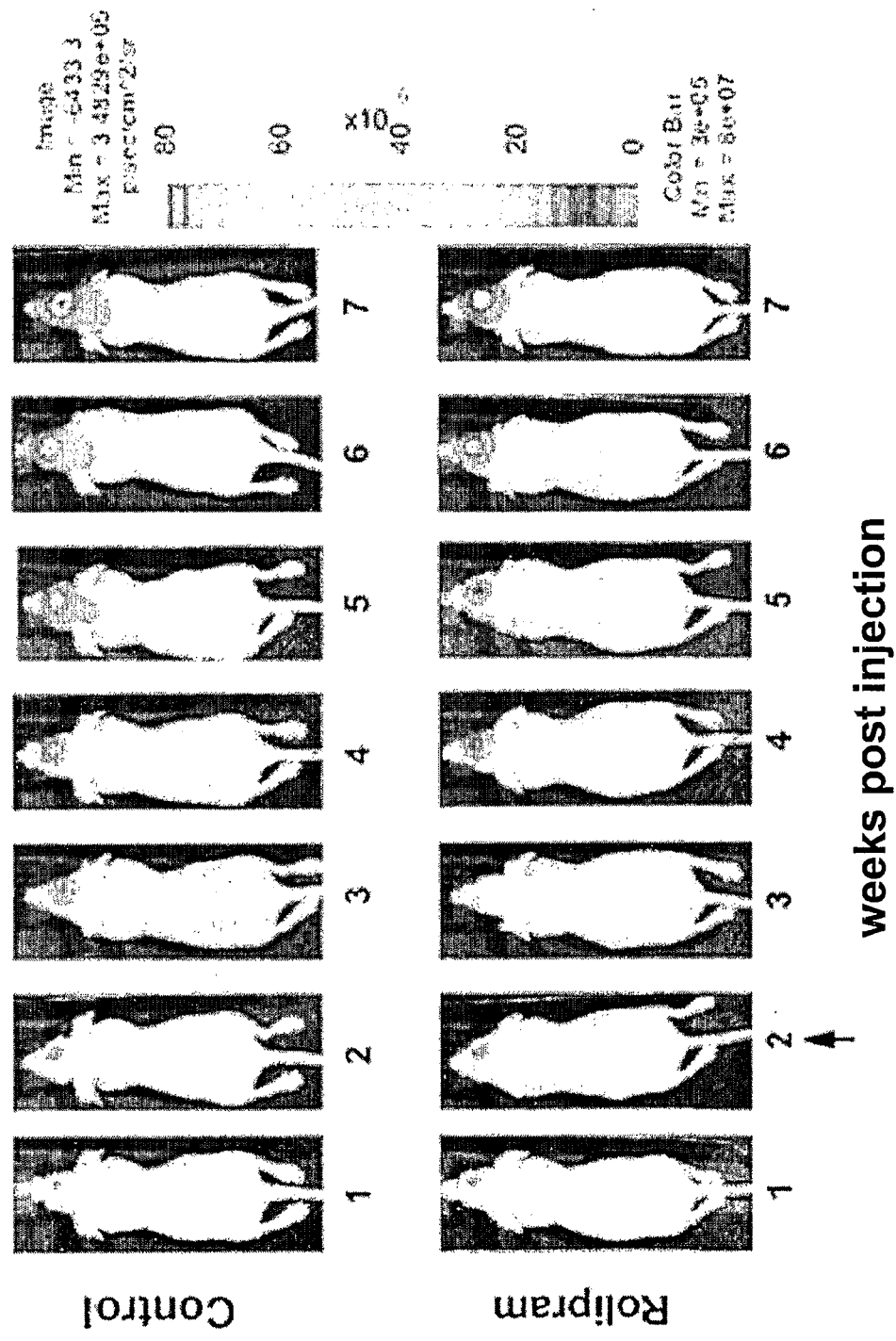

FIG. 19 depicts a series of photographic images and graphs illustrating cyclic AMP elevating drugs blocking brain tumor growth in vivo. (A) Representative weekly bioluminescence images from mice bearing Daoy xenografts from control and oral Rolipram (5 µg/g/day) treatment groups. Arrow indicates the start of treatment. (B) Means and SEM of weekly bioluminescence ratios of U87 and Daoy xenograft control and Rolipram treatment group photon flux values over pre-treatment values (ten animals/group). (C) Means and SEM of weekly bioluminescence ratios of Daoy control and caffeine (100 µg/g/day) treatment group photon flux values over pre-treatment values (10 animals/treatment group). =p<0.005 and *=p<0.0005 for the difference between the curves as determined by two-way ANOVA.

Figure 20A:
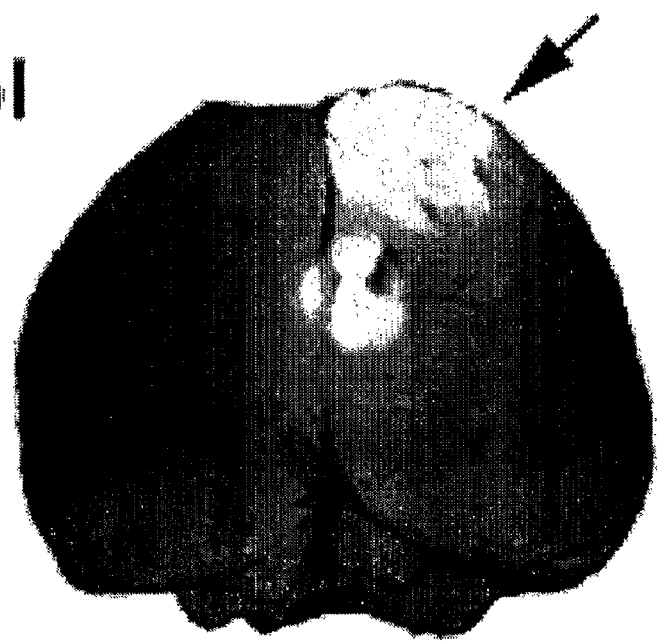
Figure 20A:
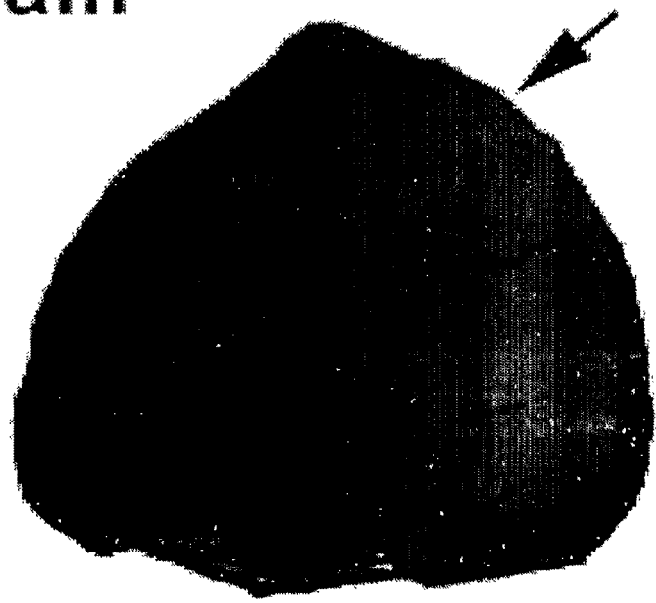

FIG. 20 depicts a diagram and a graph showing that Rolipram elevates intratumoral cAMP in vivo. (A) Representative mice from U87 control and oral Rolipram (5 µg/g/day) treatment groups demonstrating tumor localization via fluorescence. (B) Cyclic AMP was extracted from tumor tissue and measured by ELISA. Presented are the means and SEM of determinations from 3 separate animals/treatment group. *=p<0.05 **=p<0.005 compared to control as determined by two-tailed t-test.

FIG. 21 depicts a table of the mean scores for astrocytoma staining. *Scores were determined as the mean score from three independent observers using the following scale: 1=1-25%, 2=26-50%, 3=51-75%, 4=76-100% of blood vessels positive. †scores were determined as the mean score from three independent observers using the following scale: 1=1-25%, 2=26-50%, 3=51-75%, 4=76-100% of tumor cells positive.

DETAILED DESCRIPTION OF THE PREFERRED EMBODIMENTS

The present invention provides novel chemokine receptor antibodies that selectively bind to an activated form of a chemokine receptor, such as CXCR4. Activation of CXCR4 is known to be associated with the growth and spread of several cancers. Advantageously, because the antibodies of the current invention selectively recognize the activated form of CXCR4, for example, they may be utilized in methods for diagnosing disorders associated with increased CXCR4 activation, in methods for monitoring the effectiveness of a therapy for a disorder associated with CXCR4 activation, and in methods for screening compounds that prevent CXCR4 activation.

Chemokine Receptor Antibodies

One aspect of the invention provides chemokine receptor antibodies that may bind to an activated form of the receptor but not to a non activated form of the receptor. In one embodiment, the antibodies may bind to a phosphorylated chemokine receptor. In another embodiment, the antibodies may selectively bind to a phosphorylated form of the chemokine receptor but not to a non phosphorylated form of the chemokine receptor. In still another embodiment, the antibodies may bind to a ligand activated form of the chemokine receptor. In an alternate embodiment, the antibodies may recognize a ligand-induced change in the receptor in yet another embodiment, the antibodies may bind to a form of the chemokine receptor that is activated via mutation. The mutation may be synthetically induced or naturally occurring. In each of the foregoing embodiments, the chemokine receptor may include CCR1, CCR2, CCR3, CCR4, CCR5, CCR6, CCR7, CCR8, CXCR1, CXCR2, CXCR3, CXCR4, and CCX-CKR2.

Typically, the antibodies of the invention will selectively recognize the human chemokine receptor CXCR4. In one embodiment, the antibodies may recognize phosphorylated CXCR4. In one alternative of this embodiment, CXCR4 may be phosphorylated on any of amino acid residues 332 to 346. In another alternative of this embodiment, CXCR4 may be phosphorylated on amino acid residue 338. In still another alternative of this embodiment, CXCR4 may be phosphorylated on amino acid residue 339. In a further embodiment, the antibodies may selectively bind to a phosphorylated form of CXCR4 but not to a non phosphorylated form of CXCR4. In one alternative of this embodiment, the antibodies may selectively bind to CXCR4 phosphorylated on serine residue 339 but not to CXCR4 receptor phosphorylated on serine 338. In yet another alternative of this embodiment, the antibodies may selectively bind to CXCR4 phosphorylated on serine residue 338 but not to CXCR4 receptor phosphorylated on serine 339. In another alternative of this embodiment, CXCR4 may be phosphorylated on amino acid residues other than residues 332 to 346. In another embodiment, the antibodies may selectively bind to a ligand activated CXCR4. In still another embodiment, the antibodies may recognize a ligand-induced change in the CXCR4 receptor. By way of non-limiting example, the ligand may be CXCL12.

In certain embodiments of the invention, the antibodies may be labeled with a detectable marker. The marker may be either non covalently or covalently joined to an antibody of the present invention by methods generally known in the art. Detectable markers suitable for use in the invention generally comprise a reporter molecule or enzyme that is capable of generating a measurable signal. By way of non-limiting example, such detectable markers include a chemiluminescent moiety, an enzymatic moiety, a fluorescent moiety and a radioactive moiety.

According to the invention, an activated CXCR4 receptor, its fragments or other derivatives, or analogs thereof, may be used as an immunogen to generate antibodies having the desired specificity using methods that are well known in the art. Such antibodies include but are not limited to polyclonal, monoclonal, chimeric, single chain antibodies, a humanized antibody, Fab fragments, and fragments produced by a Fab expression library. In a specific embodiment, antibodies to an activated human CXCR4 receptor are produced. In another embodiment, antibodies to a domain of an activated CXCR4 receptor are produced. In a specific embodiment, a phosphorylated fragment of human CXCR4 receptor is used as an immunogen for antibody production. In an exemplary embodiment, a CXCR4 fragment having at least one of amino acid residues 332-346 that is phosphorylated, as illustrated in the examples, is used as an immunogen for antibody production.

It is preferred that the oligopeptides, peptides, or fragments used to induce antibodies to an activated CRCR4 receptor have an amino acid sequence consisting of at least about 5 amino acids, and generally will consist of at least about 10 amino acids. It is also preferable that these oligopeptides, peptides, or fragments generally are identical to a portion of the amino acid sequence of the natural protein. Short stretches of activated CXCR4 polypeptide may be fused with those of another protein, such as KLH, and antibodies to the chimeric molecule may be produced.

For the production of polyclonal antibodies, various hosts including goats, rabbits, rats, mice, humans, and others may be immunized by injection with an activated CXCR4 polypeptide, as detailed above, that has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *corynebacterium parvum* are especially preferable.

Monoclonal antibodies to activated CXCR4 receptors or fragments thereof may be prepared using a technique that provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495-497; Kozbor, D. et al. (1985) J. Immunol. Methods 81:3142; Cote, R. J. et al. (1983) Proc. Natl. Acad. Sci. USA 80:2026-2030; and Cole, S. P. et al. (1984) Mol. Cell. Biol. 62:109-120.)

In addition, techniques developed for the production of "chimeric antibodies," such as the splicing of mouse antibody genes to human antibody genes to obtain a molecule with appropriate antigen specificity and biological activity may be used. (See, e.g., Morrison, S. L. et al. (1984) Proc. Natl. Acad. Sci. USA 81:6851-6855; Neuberger, M. S. et al. (1984) Nature 312:604-608; and Takeda, S. et al. (1985) Nature 314:452-45). Alternatively, techniques described for the production of single chain antibodies may be adapted, using methods known in the art, to produce activated CXCR4-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134-10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833-3837; Winter, G. et al. (1991) Nature 349:293-299.)

Antibody fragments that contain specific binding sites for activated CXCR4 receptor or fragments thereof may also be generated. For example, such fragments include, but are not limited to, $F(ab')_2$ fragments produced by pepsin digestion of the antibody molecule and Fab fragments generated by reducing the disulfide bridges of the $F(ab')_2$ fragments. Alternatively, Fab expression libraries may be constructed to allow rapid and easy identification of monoclonal Fab fragments with the desired specificity. (See, e.g., Huse, W. D. et al. (1989) Science 246:1275-1281.)

In the production of antibodies, screening for the desired antibody may be accomplished by techniques known in the art, e.g. ELISA (enzyme-linked immunosorbent assay). Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between activated CXCR4 receptor and its specific antibody.

Various methods such as Scatchard analysis in conjunction with radioimmunoassay techniques may be used to assess the affinity of antibodies for activated CXCR4 receptor. Affinity is expressed as an association constant, $K_a$, which is defined as the molar concentration of CXCR4-antibody complex divided by the molar concentrations of free antigen and free antibody under equilibrium conditions. The $K_a$ determined for a preparation of polyclonal antibodies, which are heterogeneous in their affinities for multiple activated CXCR4 epitopes, represents the average affinity, or avidity, of the antibodies for activated CXCR4. The $K_a$ determined for a preparation of monoclonal antibodies, which are monospecific for a particular activated CXCR4 epitope, represents a true measure of affinity. High-affinity antibody preparations with $K_a$ ranging from about $10^9$ to $10^{12}$ L/mole are preferred for use in immunoassays in which the activated CXCR4-antibody complex must withstand rigorous manipulations. Low-affinity antibody preparations with $K_a$ ranging from about $10^6$ to $10^7$ L/mole are preferred for use in immunopurification and similar procedures that ultimately require dissociation of CXCR4, preferably in active form, from the antibody.

The titer and avidity of polyclonal antibody preparations may be further evaluated to determine the quality and suitability of such preparations for certain downstream applications. Procedures for evaluating antibody specificity, titer, and avidity, and guidelines for antibody quality and usage in various applications, are generally available.

Diagnostic Use of Chemokine Receptor Antibodies

Another aspect of the invention encompasses several diagnostic uses of the chemokine receptor antibodies. The antibodies may also be employed for therapeutic purposes.

In one embodiment, the chemokine receptor antibodies may be utilized in a diagnostic test for a disorder associated with increased activation of CXCR4 in a subject. In the test, the level of activated CXCR4 is measured in a biological sample taken from the subject. The level of activated CXCR4 is also measured in a biological sample from one or more control tissues (the control tissue may be from a different organ or tissue in the same subject or may be the same type of organ or tissue in a different subject known not to have the disorder). The level of activated CXCR4 in the subject is then compared with the level of activated CXCR4 from the control sample, wherein an increase in the measured level of activated CXCR4 in the subject compared to the control sample indicates the presence of the disorder in the subject. Typically, the level of activated CXCR4 is measured in the subjects by detecting the presence of a CXCR4 antibody of the invention that is labeled with a detectable marker according to any of the embodiments detailed herein, including by an immunoassay. The immunoassays that may be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. In a preferred embodiment, the diagnostic test may be used to detect the presence of a tumor cell that is malignant. The tumor cell may comprise a cancer cell selected from the group consisting of skin, prostate, pancreatic, cervical, ovarian, bladder, brain, lung, colorectal, renal, head and neck, stomach, uterine, lymphoma, including B cell lymphoma, breast, and hematological. In an exemplary embodiment, the cancer may be brain cancer selected from the group consisting of glioblastoma, glioma, meningioma, astrocytoma, medulloblastoma, neuroectodermal cancer and neuroblastoma. In each of the foregoing embodiments, the subject is typically a human, but may also be a companion animal such as a dog or cat, a livestock animal such as a cow, horse, sheep or pig, or a rodent, such as a mouse, rat or guinea pig.

In an additional embodiment, a method for monitoring the effectiveness of a therapy for cancer in a subject undergoing treatment is provided. The method involves periodically measuring changes in the level of activated CXCR4 in a biological sample obtained from the subject. The change in the level of activated CXCR4 is preferably correlated with the effectiveness of the therapy. Typically, a lower level of activated CXCR4 in the biological sample determined at a later time point relative to the level of activated CXCR4 determined at an earlier time point during the course of the therapy indicates effectiveness of the therapy for cancer. Activated CXCR4 may be measured using the antibodies of the invention according the described methods, such as by measuring a labeled antibody via any of the immunoassays detailed herein.

In another embodiment, the chemokine receptor antibodies may be used to determine whether a biological sample contains an activated form of a chemokine receptor. In the method, a biological sample is contacted with an antibody of the present invention that selectively binds to an activated form of the chemokine receptor but not to the non activated form of the chemokine receptor. After the antibody has incubated with the biological sample under suitable reaction conditions for a reasonable length of time, it is determined whether the antibody binds to the biological sample, wherein binding of the antibody to the biological sample indicates that the biological sample contains an activated form of the chemokine receptor. Typically, the antibody is labeled with a detectable marker that can be quantified by procedures generally known in the art, such as by immunoassay. The biological sample may include a tissue biopsy, bodily fluid, an extract from a cell, an organelle, or a membrane isolated from a cell. In a preferred embodiment, the method may be used to detect the presence of a tumor cell that is malignant. The biological sample may comprise a cancer cell or portion of the cell selected from the group consisting of skin, prostate, pancreatic, cervical, ovarian, bladder, brain, lung, colorectal, renal, head and neck, stomach, uterine, lymphoma, including B cell lymphoma, breast, and hematological. In an exemplary embodiment, the cancer may be brain cancer selected from the group consisting of glioblastoma, glioma, meningioma, astrocytoma, medulloblastoma, neuroectodermal cancer and neuroblastoma. In each of the foregoing embodiments, the biological sample is typically isolated by methods generally known in the art from a subject that is typically a human, but may also be a companion animal such as a dog or cat, a livestock animal such as a cow, horse, sheep or pig, or a rodent, such as a mouse, rat or guinea pig.

Additionally, the invention encompasses diagnostic assays to monitor cAMP levels in a biological sample. In one embodiment, as the level of activated CXCR4 increases in a biological sample, the level of cAMP decreases in the biological sample. In another embodiment, as the level of activated CXCR4 levels decrease in a biological sample, the level of cAMP increases in a biological sample. Generally, increases in cAMP levels are correlated with tumor suppression, while decreases in cAMP levels are correlated with tumor growth. Therefore, the level of CXCR4 activation can be correlated to tumor growth or suppression by using activated CXCR4 to monitor cAMP levels. Typically, CXCR4 activity is detected by adding an antibody of the invention that is labeled with a detectable marker in accordance with any embodiment described herein. cAMP levels can be measured by methods commonly known in the art, including ELISA.

Use of the Chemokine Receptor Antibodies to Screen for Compounds

Another aspect of the invention provides assays performed to screen for molecules with potential utility as anti-cancer drugs or lead compounds for drug development. In one embodiment, a method is provided for screening a compound for effectiveness as an antagonist of CXCR4 activation. In the method, a compound is combined with a sample comprising non activated CXCR4 to form a mixture of the compound and the sample. A ligand, such as CXCL12, is then added under conditions suitable for the ligand to activate CXCR4. CXCR4 activation is then detected, wherein CXCR4 activation indicates that the compound does not have CXCR4 antagonist activity. Typically, CXCR4 activity is detected by adding an antibody of the invention that is labeled with a detectable marker in accordance with any embodiment described herein.

The invention also provides assays to detect molecules that specifically bind to activated CXCR4. Molecules (e.g., putative binding partners of CXCR4) are contacted with the CXCR4 under conditions conducive to binding, and then molecules that specifically bind to the activated CXCR4 protein are identified.

Methods that may be used to carry out the foregoing are commonly known in the art. By way of example, diversity libraries, such as random or combinatorial peptide or nonpeptide libraries can be screened for molecules that specifically bind to activated CXCR4. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767-773; Houghten et al., 1991, Nature 354:84-86; Lam et al., 1991, Nature 354:82-84; Medynski, 1994, Bio/Technology 12:709-710; Gallop et al., 1994, J. Medicinal Chemistry 37(9):1233-1251; Ohlmeyer et al., 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayawickreme et al., 1994, Proc. Natl. Acad. Sci. USA 91:1614-1618; Salmon et al., 1993, Proc. Natl. Acad. Sci. USA 90:11708-11712; PCT Publication No. WO 93/20242; and Brenner and Lerner, 1992, Proc. Natl. Acad. Sci. USA 89:5381-5383. Examples of phage display libraries are described in Scott and Smith, 1990, Science 249:386-390; Devlin et al., 1990, Science, 249:404-406; Christian, R. B., et al., 1992, J. Mol. Biol. 227:711-718); Lenstra, 1992, J. Immunol. Meth. 152:149-157; Kay et al., 1993, Gene 128:59-65; and PCT Publication No. WO 94/18318 dated Aug. 18, 1994. In vitro translation-based libraries include but are not limited to those described in PCT Publication No. WO 91/05058 dated Apr. 18, 1991; and Mattheakis et al., 1994, Proc. Natl. Acad. Sci. USA 91:9022-9026.

Screening the libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992; BioTechniques 13:422-427; Oldenburg et al., 1992, Proc. Natl. Acad. Sci. USA 89:5393-5397; Yu et al., 1994, Cell 76:933-945; Staudt et al., 1988, Science 241:577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. Nos. 5,096,815, 5,223, 409, and 5,198,346, all to Ladner et al.; Rebar and Pabo, 1993, Science 263:671-673; and PCT Publication No. WO 94/18318.

In a specific embodiment, screening may be conducted by contacting the library members with activated CXCR4 immobilized on a solid phase and harvesting those library members that bind to the protein as detected by immunoassays employing the antibodies of the invention. Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318.

Use of the Chemokine Receptor Antibodies to Purify Chemokine Receptors

In an additional embodiment, the invention encompasses a method for purifying a phosphorylated chemokine receptor from a biological sample containing a chemokine receptor. In the method, an affinity matrix is provided comprising an antibody of the invention that selectively binds to a phosphorylated form of the chemokine receptor but not to a non phosphorylated form of the chemokine receptor. Typically, a biological sample is contacted with the affinity matrix to produce an affinity matrix-phosphorylated receptor complex. The affinity matrix-phosphorylated receptor complex is separated from the remainder of the biological sample and the phosphorylated chemokine receptor is released from the affinity matrix to form a purified phosphorylated chemokine receptor.

Kits for Detecting Activated Chemokine Receptors

Kits for use for in vitro or in vivo determination of chemokine receptor activation, such as in methods for tumor localization and therapy methods, will typically include the antibodies of the invention (or fragments thereof) conjugated to any of the detectable labels detailed herein. The components of the kits may be packaged either in aqueous medium or in lyophilized form. When the antibodies (or fragments thereof are used in the kits in the form of conjugates in which a label or a therapeutic moiety is attached, such as a radioactive metal ion or a therapeutic drug moiety, the components of such conjugates may be supplied either in fully conjugated form, in the form of intermediates or as separate moieties to be conjugated by the user of the kit. The kits will also typically include instructions, the contents of which will vary depending upon the use of the kit.

DEFINITIONS

The term "antagonist" refers to a molecule that inhibits or attenuates the biological activity of a chemokine receptor. Antagonists may include proteins such as antibodies, nucleic acids, carbohydrates, small molecules, or other compounds or compositions that modulate the activity of a chemokine receptor either by directly interacting with the chemokine receptor or by acting on components of the biological pathway in which chemokine receptor participates.

The term "antibody" refers to intact immunoglobulin molecules as well as to fragments thereof, such as Fab, F(ab')$_2$, and Fv fragments, which are capable of binding an epitopic determinant. Non-limiting examples of antibodies encompassed by the invention include a polyclonal antibody, a monoclonal antibody, a chimeric antibody, a single chain antibody, a humanized antibody, a Fab fragment, a F(ab')$_2$ fragment, and fragments produced by a Fab expression library.

The term "antigenic determinant" refers to that region of a molecule (i.e., an epitope) that makes contact with a particular antibody. When a protein or a fragment of a protein is used to immunize a host animal, numerous regions of the protein may induce the production of antibodies that bind specifically to antigenic determinants (particular regions or three-dimensional structures on the protein). An antigenic determinant may compete with the intact antigen (i.e., the immunogen used to elicit the immune response) for binding to an antibody.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, and/or malignancy (see, Freshney, Culture of Animal Cells a Manual of Basic Technique (3.sup.rd ed. 1994)).

The term "chemokine receptor" refers to an integral membrane protein that belongs to the superfamily comprised of heterotrimeric G protein-coupled receptors with seven transmembrane spanning domains. Chemokine receptors bind proteins belonging to the CC, the CXC, the CXXC or the CXXXC chemokine subfamilies. Chemokine receptors may include both receptors with known chemokine ligands, and receptors whose chemokine ligands have not yet been identified.

The terms "CXCR4 polynucleotide" and "CXCR4 polypeptide" refer to nucleic acid and polypeptide polymorphic variants, alleles, mutants, and interspecies homologs that: (1) have a nucleotide sequence that has greater than about 60% nucleotide sequence identity, 65%, 70%, 75%, 80%, 85%, 90%, preferably 91%, 92%, 93%, 94%, 95%, 96%, 99%, 98% or 99% or greater nucleotide sequence identity, preferably over a region of over a region of at least about 25, 50, 100, 200, 500, 1000, or more nucleotides, to Unigene hs.89414, and GenBank Accessions No. AF025375 L08176, L31581, NM001838; (2) bind to antibodies, e.g., polyclonal antibodies, raised against an immunogen comprising an amino acid sequence as shown in these accessions (3) specifically hybridize under stringent hybridization conditions to a nucleic acid sequence, or the complement thereof of the sequences in these accessions (stringent conditions involve hybridizing at 68° C. in 5×SSC/5×Denhardt's solution/1.0% SDS, and washing in 0.2×SSC/0.1% SDS at room temperature; for more information see Sambrook et al., 1989, Molecular Cloning, A Laboratory Manual, Cold Spring Harbor Press, N.Y.; and Ausubel et al., (eds.), 1995, Current Protocols in Molecular Biology, (John Wiley & Sons, N.Y.) at Unit 2.10); or (4) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino sequence identity, preferably over a region of over a region of at least about 25, 50, 100, 200, 350, or more amino acids, to the amino acid sequences noted above. A polynucleotide or polypeptide sequence is typically from a mammal including, but not limited to, primate, e.g., human; rodent, e.g., rat, mouse, hamster; cow, pig, horse, sheep, or another mammal. A "CXCR4 polypeptide" and a "CXCR4 polynucleotide," may be either naturally occurring or recombinant. Similarly the terminology is used with respect to the other receptors and their sequences, e.g., CCR1, CCR2, CCR4, CCR5, CCR7, CCR8, CX3CR1 and CXCR6. See, e.g., GenBank accessions noted above.

The percent of sequence identity of two polypeptides or two nucleic acid sequences is determined using the algorithm of Karlin and Altschul (Proc. Natl. Acad. Sci. USA 87:2264-2268, 1993). Such an algorithm is incorporated into the NBLAST and XBLAST programs of Altschul et al. (J. Mol. Biol. 215:403-410, 1990). BLAST nucleotide searches may be performed with the NBLAST program to obtain nucleotide sequences homologous to a nucleic acid molecule of the invention. Equally, BLAST protein searches may be performed with the XBLAST program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., XBLAST and NBLAST) are employed. See http://www.ncbi.nlm.nih.gov for more details.

A "detectable label" refers to a reporter molecule or enzyme that is capable of generating a measurable signal and is covalently or noncovalently joined to an antibody of the present invention. Typically, the label is detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "disorder" is used in its broadest sense. Depending upon the embodiment of the invention, for example, a disorder may comprise an inflammatory disease, such as rheumatoid arthritis or multiple sclerosis; an autoimmune disorder such as lupus, graft rejection, or graft versus host disease; the presence of malignant cell growth; or any other physical or mental condition that would cause an increase in CXCR4 activation.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from open reading frames that flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

The term "sample" or "biological sample" is used in its broadest sense. Depending upon the embodiment of the invention, for example, a sample may comprise a bodily fluid; an extract from a cell, chromosome, organelle, or membrane isolated from a cell; a cell; genomic DNA, RNA, or cDNA, in solution or bound to a substrate; a tissue; a tissue print or any other material isolated in whole or in part from a living subject. Preferably, the sample of biological tissue or fluid contains a chemokine receptor protein. Such samples include, but are not limited to, tissue isolated from primates, e.g., humans, or rodents, e.g., mice, and rats. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

A biological sample is "designed for the detection of" a particular cancer cell if the sample is taken from the target organ (e.g., a lung sample for detecting a lung cancer cell). In addition, the sample may be taken from an organ or tissue suspected of comprising a metastatic cell from the primary tumor. Such secondary sites may include lymph nodes or other tissues suspected of comprising metastases. Those of skill will recognize the secondary sites most commonly associated with metastasis for any particular cancer.

The term "subject" is used in its broadest sense and includes several animal species having chemokine receptors. In a preferred embodiment, the subject is a mammal. Non-limiting examples of mammals include humans, dogs, cats, horses, cows, sheep, goats, and pigs.

"Tumor cell" refers to precancerous, cancerous, and normal cells in a tumor.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate the invention.

The following materials and methods were used in examples 1-4.

Chemicals, reagents, and antibodies. All chemicals were obtained from Sigma (St Louis, Mo.) unless otherwise indicated. All tissue culture reagents and media were obtained from Invitrogen (Carlsbad, Calif.) unless otherwise indicated. CXCR4 antibodies include monoclonal antibodies (R & D, Minneapolis Minn.) and polyclonal antibodies (Leinco, St Louis, Mo.). The CXCL12 rabbit polyclonal antibody was from Peprotech (Rocky Hills, N.J.) and the actin antibody was from Sigma. Normal goat and rabbit sera and IgG isotype control antibodies were from Jackson Immunoresearch (West Grove, Pa.).

Antibody production and purification. Peptides P338, P339 and the non-phosphorylated form of this sequence (peptide 332-346, GKRGGHSSVSTESES human CXCR4, gi:4503175) were synthesized at the Tufts University Core Facility (Boston, Mass.) with an amino-terminal cysteine to facilitate conjugation to KLH. Phosphopeptides were conjugated to KLH according to published procedures (25). Conjugated peptides were supplied to Covance Research Products (Denver, Pa.) where rabbits were immunized according to their protocol and with approval from The Washington University School of Medicine Animal Studies Committee. Sera were screened by dot blot for reactivity against the immunizing peptides. Sera with a positive screen were subjected to affinity purification by sequential column chromatography. Sera was first applied to a protein A-sepharose column and eluted with 100 mM glycine pH 3.0. Column fractions were immediately brought to pH 7.4 with 1 M Tris. Protein A eluates were next applied to an affinity resin comprised of the non-phosphorylated peptide conjugated to Affi-Gel Hydrazide (Bio-Rad, Hercules, Calif.) according to the manufacturer's instructions. The flow-through from this column represented IgG depleted of antibodies that recognized the non-phosphorylated form of the peptide. This flow-through fraction was next applied to either P338-Affi-Gel Hydrazide or P339 Affi-Gel Hydrazide resin. Phospho-peptide specific antibodies were eluted with 100 mM glycine pH 3 and immediately brought to pH 7.4 with 1 M Tris.

Cell Culture, transfections and stimulation of CXCR4 phosphorylation. The U87 glioblastoma multiforme (GBM, grade IV) cell line was obtained from the American Type Culture Collection. The LN428 GBM cell line was a kind gift of Dr Erwin van Meir (Winship Cancer Center, Emory University, Atlanta, Ga.). U87 cells were grown in minimum essential a media supplemented with 10% fetal bovine serum ((FBS), Biomedia, Foster City, Calif.). LN428 cells were grown in DMEM (Fisher, Pittsburgh, Pa.) supplemented with 10% horse serum (Sigma). All cells were grown in the presence of penicillin-streptomycin. The coding sequence for human CXCR4 was obtained by high fidelity RT-PCR (Superscript III Platinum, Invitrogen), and cloned into the expression vector pMSCVneo (Clontech, Palo Alto, Calif.). Transfections were performed with 0.3 µg of plasmid DNA in 20 µl Lipofectamine (Invitrogen)/35 mm$^2$ tissue culture dish for 9 hours according to the manufacturer's instructions. Cells recovered in Optimem supplemented with 10% FBS. Transfected and non-transfected cells were placed in serum free media for 24 hours prior to treatment with agents to stimulate CXCR4 phosphorylation. Treatment was usually for 0 or 10 minutes with 1 µg/ml CXCL12 (Peprotech, Rocky Hill N.J.), 4 µM 4-Phorbol 12-myristate 13-acetate (PMA) or 10 nM EGF. In some experiments, CXCL12 was washed away and cells were incubated for an additional 20 minutes in serum free media alone.

Tumor Tissues. Four brain autopsy and 28 astrocytoma, formalin-fixed, paraffin-embedded archival specimens were retrieved from the pathology files at Washington University School of Medicine. Samples were obtained in accordance with an Institutional Review Board-approved protocol for human research. Autopsy specimens were from children who died without a known primary central nervous system cause. Astrocytomas were classified and graded according to the WHO guidelines (52), consisting of four sporadic, optic pathway pilocytic astrocytomas (grade 1), three sporadic pilocytic astrocytomas from other locations (grade 1), five diffuse astrocytomas (grade 2), eight anaplastic astrocytomas (grade 3), and eight GBMs (grade 4).

Tissue Sections and Immunohistochemistry. Sections (5 µm) were deparaffinized in xylene and rehydrated in descending alcohols. Endogenous peroxidase was blocked with 3% $H_2O_2$ in TBST (10 mM Tris pH 8.0, 0.15 M NaCl, 0.05 TWEEN) and non-specific avidin/biotin binding sites were blocked with Vector Blocking kit (Vector Laboratories Burlingame, Calif.). Sections were additionally blocked with 10% serum from the animal source of the appropriate corresponding secondary antibody diluted in incubation media (0.1 M Tris (pH 7.5), 0.15 M NaCl, 2% non-fat dry milk and 0.1% Triton-X 100) and then, incubated in primary antibody overnight at 4° C. CXCR4 was detected using the mouse monoclonal antibody at a concentration of 1 µg/ml and CXCL12 was localized with the rabbit polyclonal antibody (1:66 dilution). P338-CXCR4 and P339-CXCR4 were detected using our rabbit polyclonal antibodies (1:66 dilution). Immunoreactive complexes were detected using the corresponding secondary biotin-conjugated antibodies augmented by streptavidin-horseradish peroxide and visualized by DAB supplied by DAKO (Carpinteria, Calif.). Slides were then counterstained with hematoxylin, dehydrated through a series of alcohols and xylene, and coverslipped in 50:50 xylene/Permount.

Control sections were incubated with antisera in the presence of a 100 µM excess of peptide or with isotype-matched IgG. Scoring of immunoreactivity was performed by three independent observers according to the following scale: CXCR4, phospho-CXCR4 score, 0=no staining, 1=1-25%, 2=26-50%, 3=51-75% and 4=76-100% of tumor cells stained. The CXCL12 score was based on the percentage of blood vessels that stained positively for CXCL12. For each antigen, a mean score for each individual tumor specimen was determined from the three independent scores. Statistical analysis was done on the differences between grade 1 and grades 2 to 4 staining scores by two-tailed t test. Specificity of phospho-specific antibody staining was ascertained through two separate methods. In the first method, antibodies were pre-incubated for 1 hour at room temperature (RT) with PBS, 100 µM non-phosphorylated peptide 332-46 or 100 µM of P338 or P339 prior to application to tissue sections. In the second method, tissue sections were pre-incubated with lambda phosphatase 8000 units/ml for 30 minutes at 25° C. prior to antibody incubation.

Immunofluorescence. LN428 GBM cells were grown and treated with CXCL12 as described above. Cells were fixed with 4% paraformaldehyde for 10 minutes at RT as described (3). Immunostaining of LN428 for CXCR4 and phospho-CXCR4 expression was carried out as described above. Secondary AlexaFluor 555-conjugated donkey anti-rabbit, AlexaFluor 488-conjugated donkey anti-mouse or anti-goat antibody was used at a concentration of 1:750 (Molecular Probes, Eugene, Oreg.) for 90 minutes. Nuclei were counterstained with DAPI.

Western Blot Analysis. Whole-cell extracts were obtained by lysing cells with lysis buffer (20 mM Tris pH 7.4, 137 mM NaCl, 10% Glycerol and 1% Triton X-100) supplemented with phosphatase inhibitor cocktail set II (Calbiochem, La Jolla, Calif.) and protease inhibitors PMSF (1 mM), leupeptin (0.005 mg/ml) and aprotonin (0.005 mg/ml). The proteins (50-75 µg) were resolved with 10% Bis-Tris gels (Invitrogen) and transferred onto the nitrocellulose membrane Hybond ECL (Amersham, Piscataway, N.J.) according to standard protocols. Polyclonal anti-CXCR4 antibody was used at a 1:500 dilution and P338-CXCR4 and P339-CXCR4 directed antibodies were used at 1:100 dilutions overnight at 4° C. This was followed by incubation with horseradish peroxidase-conjugated secondary antibody (1:15,000; Bio-Rad). Peroxide activity was detected using the enhanced chemiluminescence Supersignal West Dura system (Pierce, Rockford, Ill.). Mouse anti-actin antibody at a concentration of 1:1500 was used as a loading control. Peptide competitions and lambda phosphatase treatment were performed as described above.

Example 1

Characterization of Anti-phospho-CXCR4 Antibodies

Figure 1A:
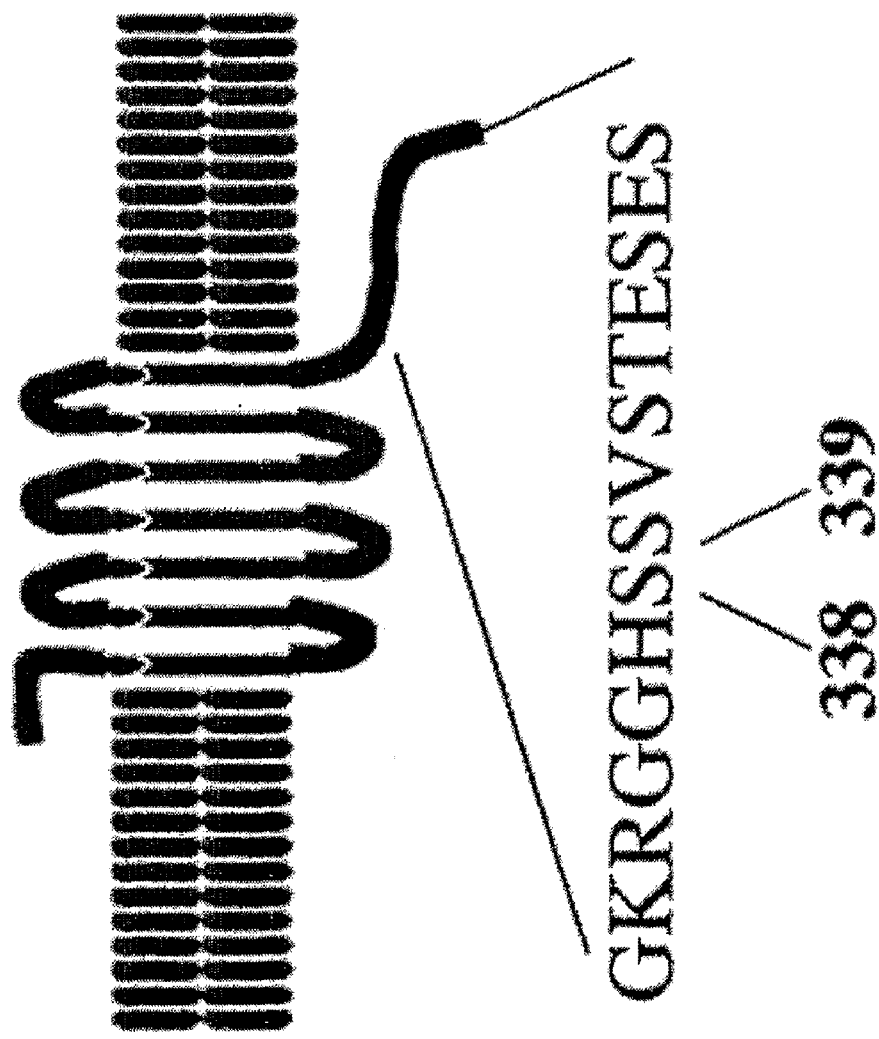
FIG. 1 depicts a series of graphs and images characterizing phospho-selectivity of the antibodies of the invention. (A) depicts a schematic illustrating the topology of CXCR4 and phospho-peptide sequences. (SEQ ID NO:1) (B) depicts an image of a western blot analysis of LN428 GBM cells treated with CXCL12. Lysates were probed with P338-CXCR4 (lane 1), P339-CXCR4 (lane 2), or a CXCR4 Ab. Molecular weight markers are indicated. (C) depicts an image of a western blot analysis of CXCR4 immunoprecipitated from LN428 GBM treated with CXCL12. Blots were first probed with P338-CXCR4 (lane 1) or P339-CXCR4 (lane 3) antibodies as indicated, then stripped and reprobed with CXCR4 antibody (lanes 2 and 4). Calculated molecular weight of the labeled band was 47 kD. (D) depicts an image of a western blot analysis showing lysates from untransfected U87 cells (U) and CXCR4 transfected U87 cells (T) were probed with P338-CXCR4 and P339-CXCR4 directed antibodies as indicated. Increased labeling of a 47 kD band is evident after transfection. Actin served as a loading control. (E) depicts an image of a western blot analysis demonstrating that antibody labeling (con) was unaffected by pre-incubating with the non-phosphorylated form of the immunizing peptide (332-46), but the P338-CXCR4 labeling of the 47 kD band was inhibited by peptide P338 while P339-CXCR4 antibody labeling was inhibited by peptide P339. Total CXCR4 labeling serves as a control for all lanes. (F) depicts an image of a western blot analysis showing that phospho-CXCR4 labeling (arrowhead), as detected by the P339 Ab, was abolished by pre-incubation of blots with lambda phosphatase (lambda). Phosphatase treatment did not affect total CXCR4.

Phospho-peptides corresponding to amino acids 332-346 (332-46) of human CXCR4 phosphorylated on either S338 (P338) or S339 (P339) (FIG. 1A) were injected into rabbits and phospho-specific antibodies were isolated from serum by sequential column chromatography.

Figure 1B:
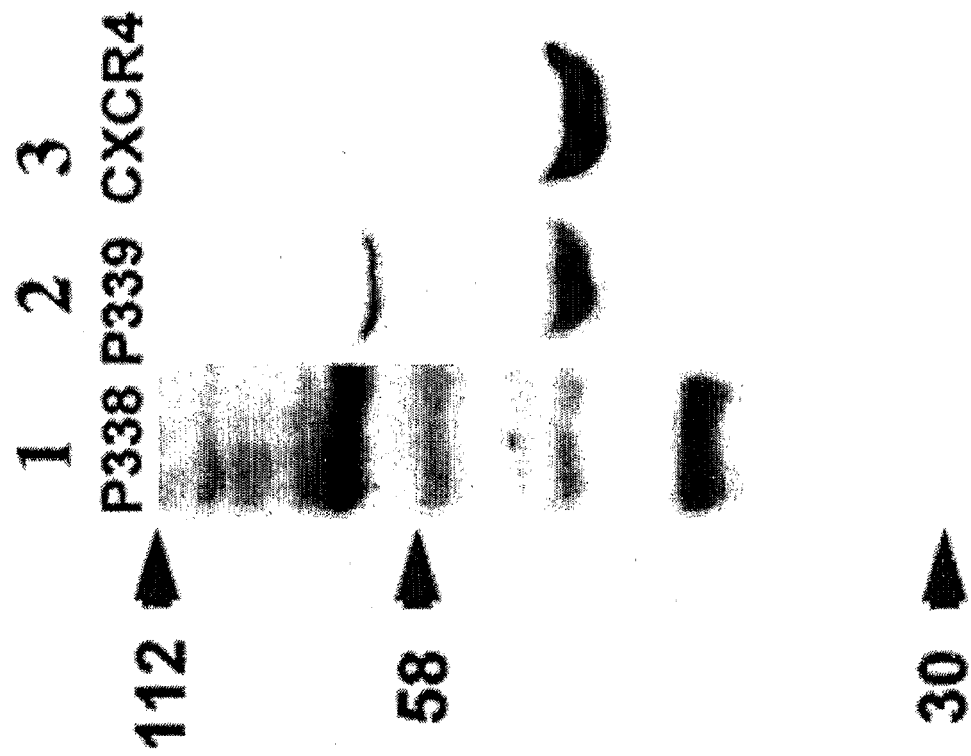
Figure 1C:
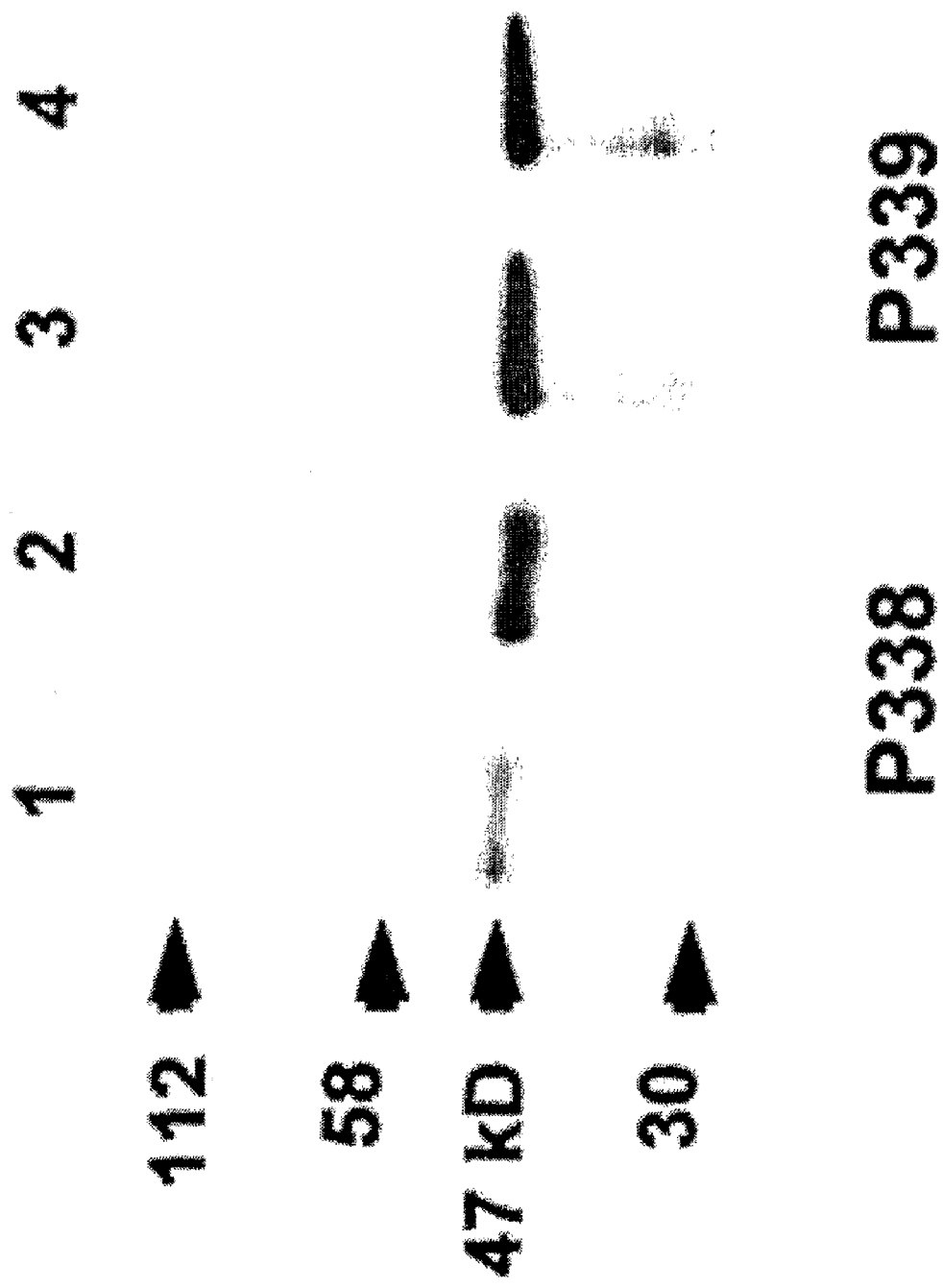
Figure 1D:
Figure 1E:
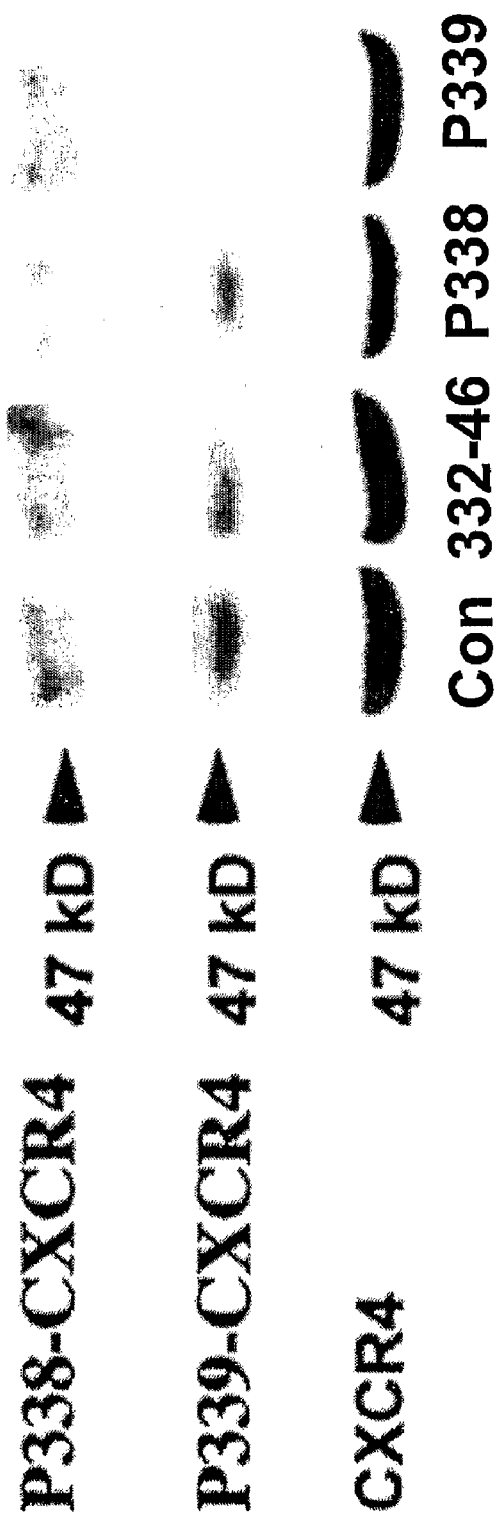
Figure 1F:
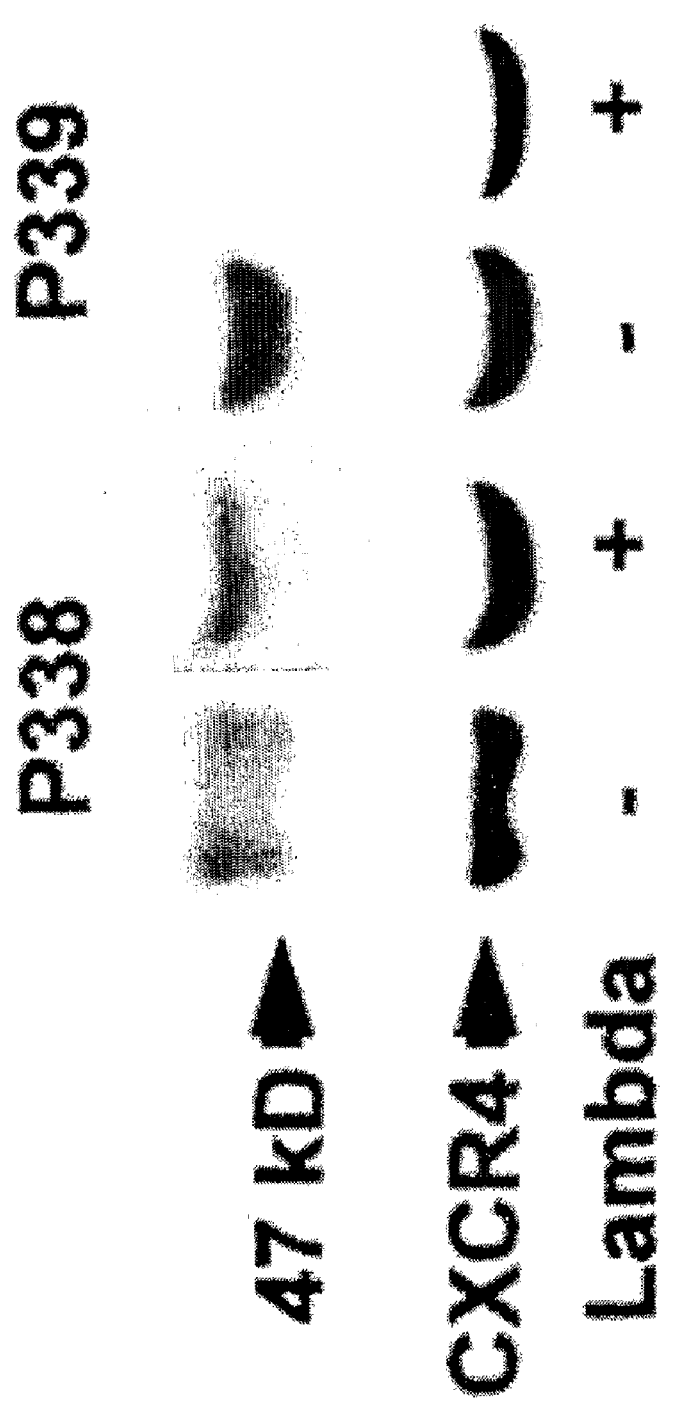

The activity of the anti-peptide antibodies was evaluated by western blot based assays utilizing lysates from the glioblastoma cell line LN428, which is known to express high levels of CXCR4 (26). Western blot analysis of LN428 cells treated with 1 µg/ml CXCL12 to promote CXCR4 phosphorylation revealed that immuno-blotting with either P338- or P339-CXCR4 directed antibodies resulted in the labeling of multiple bands (FIG. 1B). The P338-CXCR4 antibody routinely labeled proteins of 47 and 49 kD as well as bands of lower and higher molecular weight. The P339-CXCR4 antibody produced a different pattern of labeling with only a single band of 47 kD in the CXCR4 mass range. Reprobing of stripped blots with an antibody directed against the non-phosphorylated amino terminus of CXCR4 suggested that the band at 47 kD was CXCR4. In order to demonstrate antibody specificity for CXCR4, we immunoprecipitated CXCR4 from LN428 cultures treated with CXCL12. Immunopellets were first probed with antibody directed against P338-CXCR4 or P339-CXCR4, and then stripped and reprobed with anti-CXCR4 antibody (FIG. 1C). Both antibodies recognize an immunoprecipitated protein of 47 kD that was also recognized by the anti-CXCR4 antibody, suggesting that only this band represents specific CXCR4 labeling. To further support the specificity of the immunolabeling, U87 GBM cells were transfected with CXCR4. U87 GBM cells express less CXCR4 than LN428 (26) and thus an increase in signal post transfection is more apparent. Lysates from control and transfected cells treated with CXCL12 were probed with phospho-CXCR4 specific antibodies. Immunoreactivity with either antibody was increased after transfection with CXCR4 (FIG. 1D). Immunolabeling of the 47 kD band in total cell lysates by either antibody was inhibited by pre-incubation with 100 µM immunizing phosphopeptide, but not with equal concentrations of the unphosphorylated peptide or the non-immunizing phosphopeptide (FIG. 1E). The requirement for CXCR4 phosphorylation for antibody recognition was further demonstrated by treating immobilized protein blots with lambda phosphatase prior to antibody incubation. Phosphatase treatment did not decrease the level of total CXCR4 but reduced that component recognized by the phospho-specific antibodies (FIG. 1F). Together these data identify these antibodies as specific for CXCR4 phosphorylated on S338 or S339.

Figure 2A:
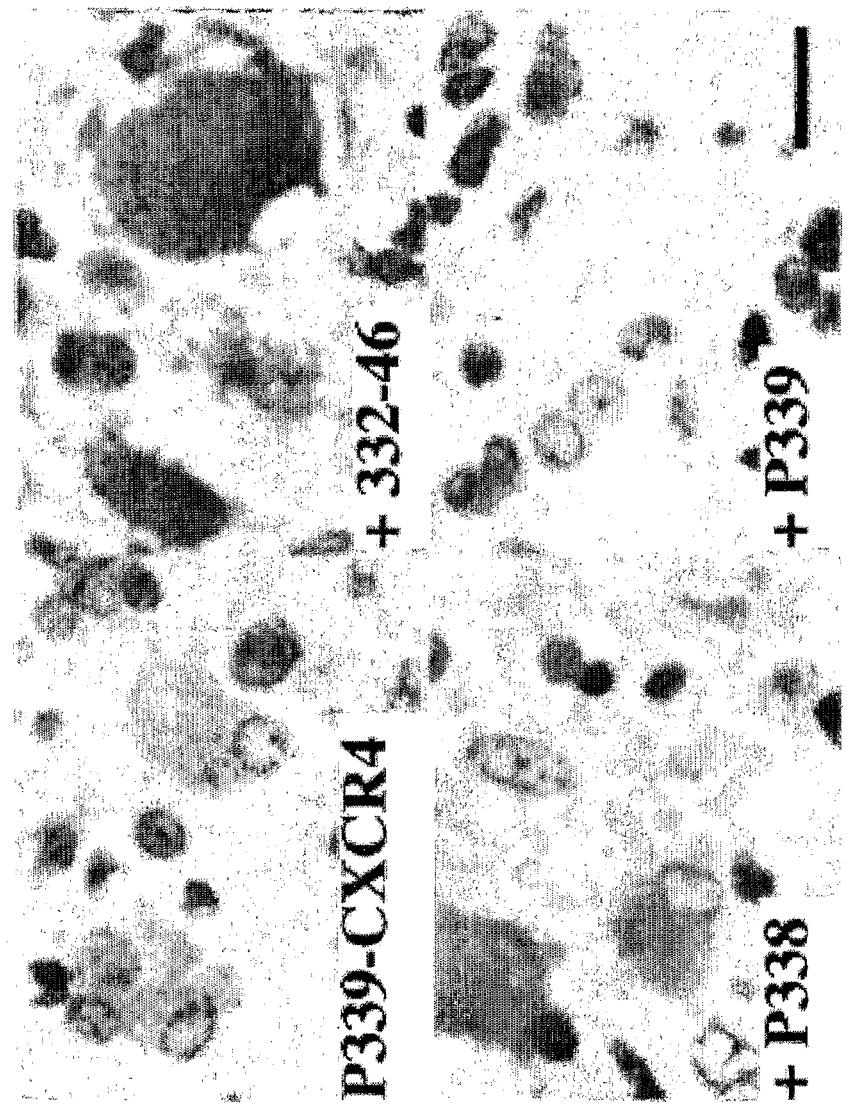
FIG. 2 depicts photographic images illustrating use of the antibodies of the invention to label tissue sections. (A) depicts a photographic image showing gemistocytes in a grade IV astrocytoma (GBM) strongly labeled with P339-CXCR4 antibody (P339-CXCR4). Staining was unaffected by pre-incubation with 100 μM of non-phosphorylated (+332-46) or P338 (+338) peptides. Staining was abolished by incubation with 100 μM of P339 (+P339). Scale bar equal to 20 μM. (B)
Figure 2B:
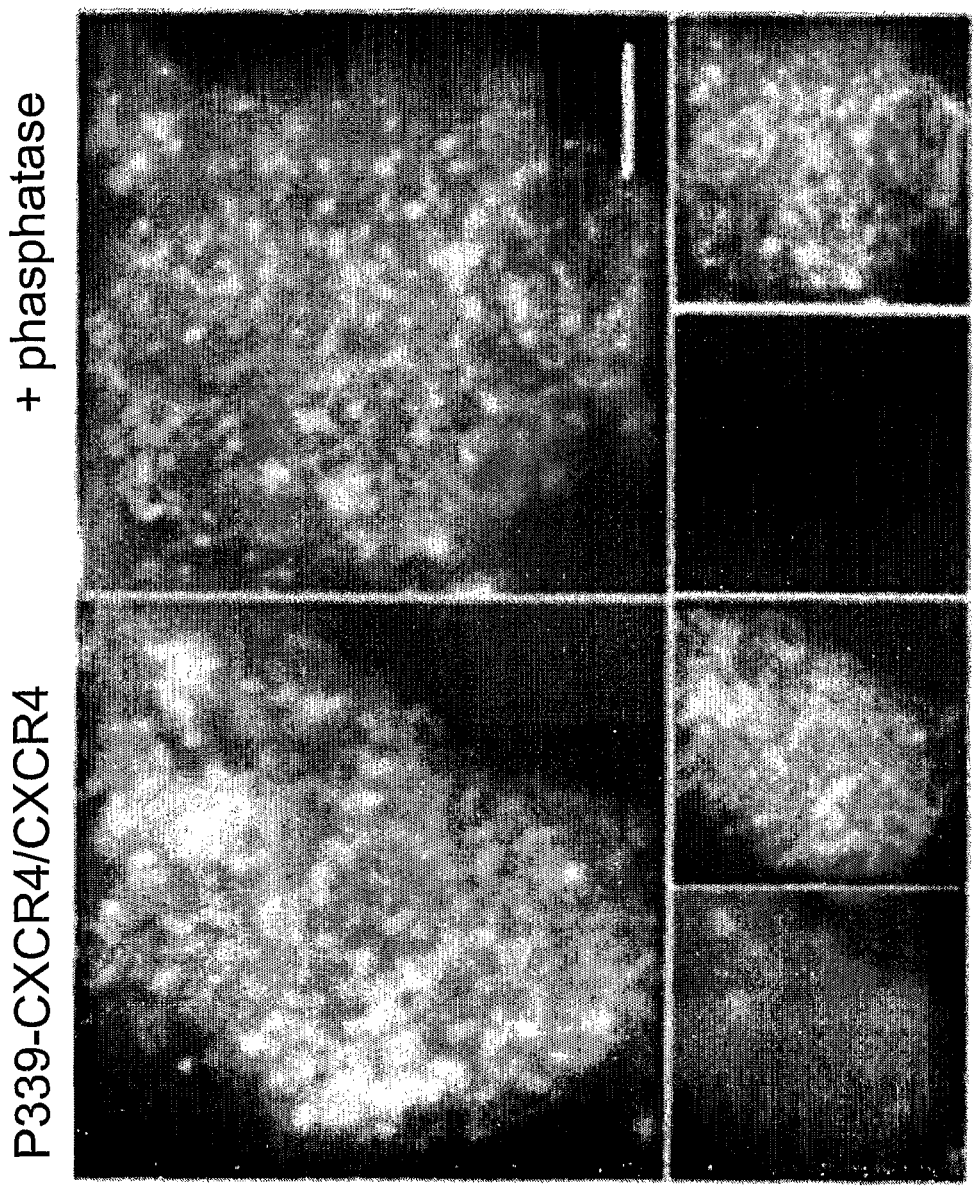

To demonstrate that the antibodies were able to specifically recognize the appropriate phosphorylated forms of CXCR4 in tissue sections, we performed peptide competitions and phosphatase treatment prior to labeling of human astrocytoma specimens with P338-CXCR4 or P339-CXCR4 antibodies. As described below, tumor gemistocytes, which appeared as large cells with eccentric nuclei, were labeled strongly by these antibodies and provided a convenient experimental subject for assays of antibody specificity. Gemistocyte staining with P339-CXCR4 (FIG. 2A, FIG. 5E inset) and P338-CXCR4 (FIG. 5F inset) antibodies displayed a characteristically diffuse cytoplasmic and membranous pattern. P339-CXCR4 staining was not diminished by preincubation with the non-phosphorylated form of the immunizing peptide (332-46) or the P338 peptide, but was abolished by pre-incubation with the P339 peptide (FIG. 2A). Similarly, labeling with P338-CXCR4 antibody was only diminished by pre-incubation with the P338, but not the 332-46 or P339 peptides (data not shown). Incubation of tissue sections with lambda phosphatase abolished P339-CXCR4 antibody labeling without diminishing CXCR4 antibody staining (FIG. 2B). P338-CXCR4 antibody labeling was similarly affected by lambda phosphatase treatment (data not shown). Therefore, these antibodies specifically recognize CXCR4 phosphorylated on S338 or S339 in western blot and immunohistochemical analyses.

Example 2

P339-CXCR4 but not P338-CXCR4 Antibodies Recognize a CXCL12 Induced Form of CXCR4

Figure 3A:
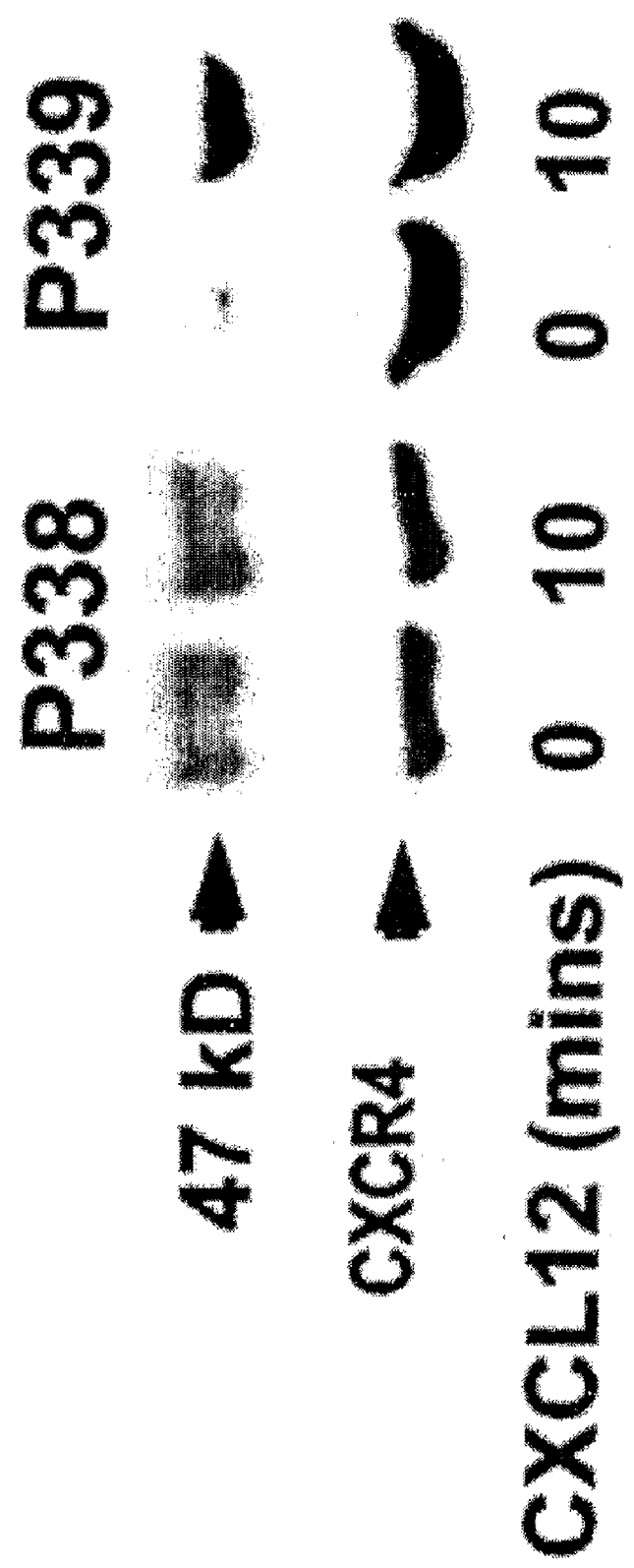
Figure 3B:
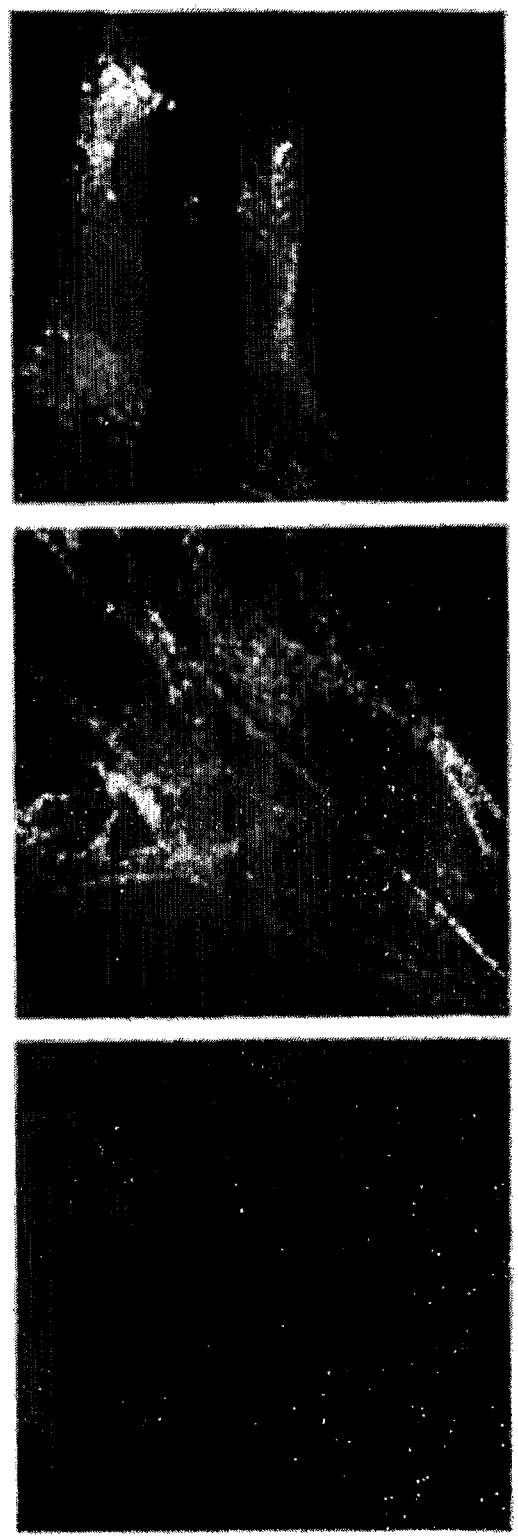

The utility of these antibodies for evaluating the relationship between ligand binding and CXCR4 function is dependent upon their ability to distinguish a ligand activated form of the receptor. Serum starvation increased CXCL12 responsiveness (data not shown), and for all of these experiments LN428 GBM cells were serum starved for 24 hours prior to CXCL12 treatment. Serum starved LN428 cells were treated with 1 µg/ml CXCL12 for 0 or 10 minutes and the abundance of phospho-CXCR4 was determined by western blot and immuno-localization in fixed cells. P338-CXCR4 western blot analysis revealed that this form of the receptor was abundant in the absence of CXCL12 and levels were unaffected by CXCL12 treatment (FIG. 3A). In contrast, in the absence of CXCL12, there was little P339-CXCR4 immunoreactivity and this was significantly increased by treatment with CXCL12 (FIG. 3A). The magnitude of the increase was dependent upon the baseline level and ranged from 2 to greater than 10 fold (data not shown). A similar CXCL12-induced increase in P339-CXCR4 (FIG. 3B), but not P338-CXCR4 (data not shown) immunoreactivity was seen by immunofluorescent analysis of paraformaldehyde fixed cells. After 10 minutes of exposure to CXCL12, P339-CXCR4 can be seen localized to the surface of LN428 cells (FIG. 3B). CXCL12 was then washed away and cells were incubated in its absence for an additional 20 minutes. Surface labeling declined as a function of time and P339-CXCR4 was seen accumulating intracellularly. These studies suggest that the P339-CXCR4, but not the P338-CXCR4 antibody recognizes a CXCL12 induced change in CXCR4 and that this change is functionally relevant to receptor trafficking.

Figure 3C:
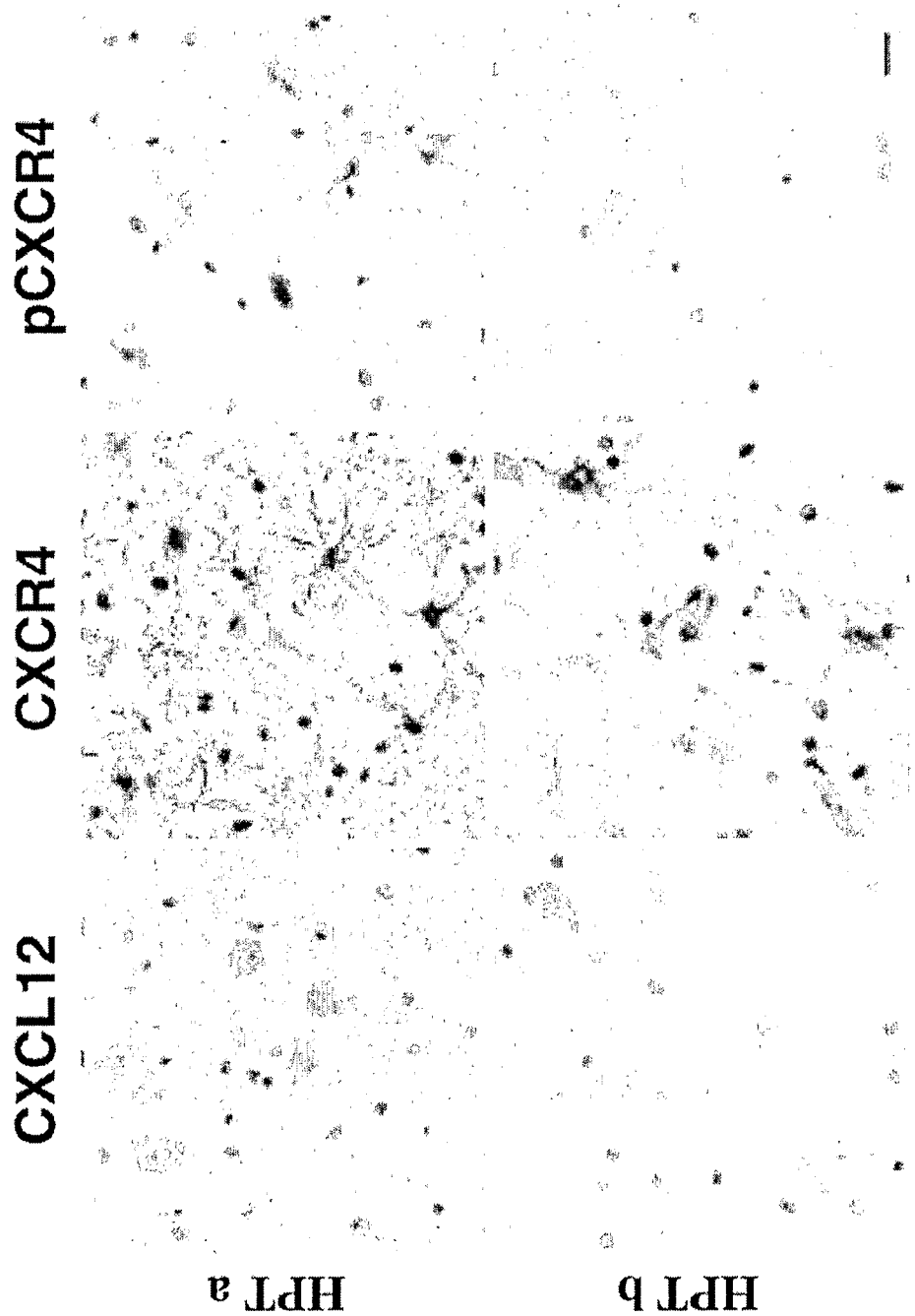
Figure 3D:
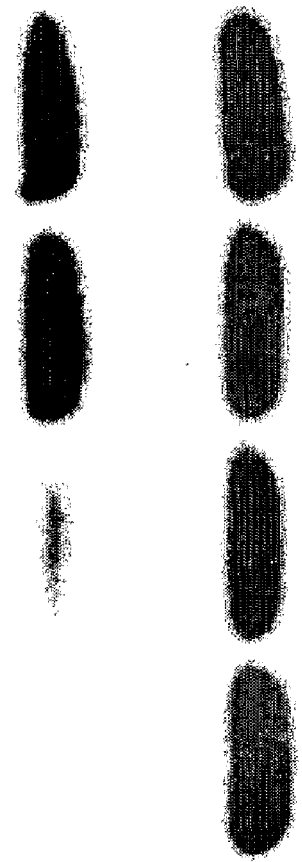

To determine what relationship P339-CXCR4 immunoreactivity had to CXCL12 expression, we examined human brain specimens for CXCL12, CXCR4, and P339-CXCR4 immunolabeling. The hypothalamus of human infants (<1 year old) contained areas with high levels of neuronal CXCL12 expression (FIG. 3C, HPTa) and other areas with little to no CXCL12 expression (FIG. 3C, HPTb). Both areas exhibited neuronal and astrocytic CXCR4 expression, but P339-CXCR4 staining was limited to neurons in the region of the hypothalamus that also expressed CXCL12. These data indicate that in normal human brain, P339-CXCR4, but not total CXCR4, immuno reactivity is highly correlated with CXCL12 expression.

Example 3

S339 but not S338 can be Phosphorylated in Response to Multiple Stimuli

Previous studies have indicated that CXCL12-induced CXCR4 phosphorylation of serine 338 and/or 339 is a GRK2 mediated process (18). Whether this is the only kinase that can phosphorylate these residues is unclear. The observation that protein kinase C (PKC) stimulated CXCR4 internalization also depends upon phosphorylation of this region of the molecule raises the question of whether these sites might also be PKC phosphorylation sites (17, 19, 27, 28). In addition, CXCR4 is likely to be co-expressed in astrocytomas along with receptor tyrosine kinases (RTK) such as the EGF receptor (29, 30). Whether CXCR4 can be phosphorylated downstream of RTK activation, in a manner similar to what is observed for insulin receptor regulation of p adrenergic receptor phosphorylation is unknown (31). To evaluate what stimuli promote S338 and S339 phosphorylation cells were treated with CXCL12, EGF or the activator of protein kinase C, PMA. All three agents stimulated P339 (FIG. 3D), but not P338 phosphorylation (data not shown). We observed greater P339-CXCR4 immunoreactivity in response to PMA or EGF than in response to CXCL12.

Specificity of P339-CXCR4 staining in tissue sections. Phosphorylation of S339 was regulated by CXCL12 and EGF and associated with changes in subcellular localization of CXCR4. Therefore, S339 seems to be an important regulatory site for CXCR4 function and we sought to define the specificity of P339-CXCR4 staining in tumor sections. To show that P339-CXCR4 was able to specifically recognize the appropriate phosphorylated form of CXCR4 in tissue sections, we did peptide competitions and phosphatase treatment before labeling of human astrocytoma specimens.

Example 4

Human Astrocytomas of all Grades Exhibit Phospho-CXCR4 Labeling

In previous studies we found that GBM and medulloblastoma expressed CXCR4 and that the endothelium of tumor-associated blood vessels expressed CXCL12 (3). The importance of this potential paracrine relationship was highlighted by the significant anti-tumor effect exerted by the specific CXCR4 antagonist AMD 3100 against intracranial xenografts of GBM and medulloblastoma. As this drug is reported to antagonize CXCL12 binding, we concluded that the paracrine relationship between CXCR4 and CXCL12 was critical for ligand activation of CXCR4 and subsequent survival signaling (13-16). We examined eight grade I, five grade II, eight grade III and eight grade IV astrocytomas to determine whether this paracrine relationship was evident regardless of histologic grade, and whether the activation of CXCR4 as determined by pCXCR4 staining was dependent upon proximity to CXCL12. All grades of astrocytoma expressed CXCL12 and CXCR4 (FIG. 4). Similar patterns of staining were observed in all grades of astrocytoma and are highlighted in representative images from a grade 2 and a grade 4 tumor (FIG. 5). In agreement with our prior studies, CXCL12 expression was localized to the endothelium of tumor-associated blood vessels in all grades of astrocytoma (FIGS.

5A&B), including the endothelial cells of glomeruloid tufts in grade 4 tumors (FIG. 5B). In several examples, CXCL12 was also localized to scattered cells possessing microglial morphology (FIG. 5A, inset). In addition to vascular endothelium and infiltrating microglia, an occasional tumor cell expressed CXCL12 (data not shown).

CXCR4 was primarily localized to tumor cells in all grades of astrocytoma (FIGS. 5 C & D). Additionally, the endothelium of tumor-associated blood vessels was frequently labeled by anti-CXCR4 antibodies (FIGS. 5C & D, arrowheads). The activation state of expressed CXCR4 was evident in the diffuse pCXCR4 immunoreactivity present in all grades of astrocytomas. Phospho-CXCR4 staining was punctuate in a cytoplasmic and membranous distribution, similar to what we have described for total CXCR4 (FIGS. 5, E & F insets). All twenty-nine tumor specimens were evaluated for P339-CXCR4 immunoreactivity but due to limited tissue availability, only eighteen could be evaluated with the P338-CXCR4 directed antibody. All tumors exhibited P339-CXCR4 staining. One specimen with no evident CXCR4 expression exhibited a small degree of P339-CXCR4 immunoreactivity of unclear significance. However, the pan-CXCR4 antibody is directed against the amino terminus of the molecule whereas P339-CXCR4 is directed against the carboxy tail. Thus, this tumor may possess a mutation in the amino terminus of CXCR4 that interferes with the pan-CXCR4 antibody binding but not that of P339-CXCR4.

Tumors (three grade I, three grade II, eight grade III, eight grade IV) were evaluated for P338-CXCR4 expression. Lower grade tumors, grades I and II, exhibited little P338-CXCR4 staining. In contrast, high-grade tumors, grades III and IV, exhibited substantial staining. The distribution of P338- and P339-CXCR4 in these tumors was diffuse throughout the tumors and closely correlated with total CXCR4 staining.

The pattern of tumor cell staining in high-grade tumors was similar with P338 and P339-CXCR4 antibodies. However, tumor associated vascular endothelium was clearly labeled with the P339-CXCR4 antibody and not by the P338-CXCR4 antibody (compare FIG. 5E to 5F, arrowheads). An additional feature of CXCR4 and CXCL12 expression that became apparent through this analysis was the high degree of CXCL12 staining in the endothelium of glomeruloid tufts in GBM (FIG. 5B, arrowhead). This was accompanied by P339-CXCR4 staining suggesting a possible autocrine relationship for endothelial cell CXCR4 activation. This may reflect the involvement of CXCR4 in the migration and proliferation of vascular endothelial cells during tumor angiogenesis (12, 32). In addition there was a consistently high degree of pCXCR4 content in gemistocytes (FIGS. 5E & F, insets). The significance of this finding remains to be evaluated, though it is intriguing that high numbers of gemistocytes in low-grade lesions has been associated with more rapid progression and a poorer prognosis. This observation could be consistent with a role for CXCR4 in glioma progression (33-35).

Tumor staining scores reveal several interesting patterns of CXCL12, CXCR4, and P339-CXCR4 expression (FIG. 6 and FIG. 21). Greater than 50% of all tumor cells, regardless of grade, expressed CXCR4 (mean score for all grades of astrocytoma is 2.59±0.25) but <50% of all endothelial cells express CXCL12 (meanscore 1.74±0.12). Grades 2 to 4 tumors that exist as a spectrum of disease called diffusely infiltrating astrocytomas (49) exhibited similar overall staining for CXCR4 and pCXCR4 regardless of grade. Grade 1 tumors are pilocytic astrocytomas that typically exhibit a more circumscribed growth pattern and whose pathogenesis differs from the diffuse astrocytomas, grades 2 through 4 (50). CXCR4 expression (FIG. 6) was greatest in grade 1 tumors (3.29±0.29) and exhibited a statistically significant difference compared with grades 2 to 4 disease (2.25±0.16, P<0.005). However, the importance of activated CXCR4 to increasingly aggressive tumor behavior was reflected in the increased proportion of CXCR4 that was present in the activated state in diffuse astrocytomas. One hundred percent of expressed CXCR4 was present in the phosphorylated state (pCXCR4/CXCR4 ratio) in grades 2 through 4 tumors compared with only 76% in grade 1 tumors (FIG. 6). Tumor staining scores, summarized in FIG. 21, reveal several interesting patterns. Greater than 50% of all tumor cells expressed CXCR4 (mean score is 2.4) but less than 50% of all endothelial cells express CXCL12 (mean score 1.6). There was a tendency towards decreased CXCL12 expression in higher-grade tumors (grade II mean 2.0, grade IV mean 1.5) producing a trend towards decreased CXCL12/P339-CXCR4 expression (0.91 in grade II and 0.7 in grade IV) and raising the possibility of ligand independent receptor activation as a feature of increasing malignancy.

To evaluate the role of CXCR4 in malignant brain tumor growth we sought to correlate CXCR4 phosphorylation and function. CXCR4 is a seven transmembrane spanning G protein coupled receptor (GPCR) with no intrinsic kinase activity. Multiple serines and threonines as well as tyrosines can be phosphorylated in response to both ligand binding or activity in parallel signaling pathways (18). Many of these sites can impact on receptor trafficking and signaling making the definition of an activated, phosphorylated form of the receptor complex and the development of a phospho-specific antibody directed at an activated state of a GPCR difficult. We were most interested in a CXCL12 activated form of CXCR4 as we suspected this would be critical to CXCR4's role in cancer and the target for CXCR4 antagonists such as AMD3100 (14, 15). Previous work on CXCR4 phosphorylation, internalization and signaling has identified the carboxy tail as a critical domain for CXCL12 induced internalization (17, 19, 20, 28, 36). Within the carboxy terminus there are at least two motifs necessary for CXCL12 induced phosphorylation and internalization. These are the dileucine motif L328 and L329 and the serines at positions 338 and 339 (18). We generated antibodies directed against peptides corresponding to amino acids 332-346 of human CXCR4 phosphorylated at either position 338 or 339. These antibodies clearly recognize a phosphorylated form of CXCR4 as evidenced by the loss of immunoreactivity upon phosphatase treatment. P339-CXCR4 antibody recognizes a CXCL12 induced change in CXCR4 on western blot analysis as well as CXCL12 induced changes in the subcellular localization of CXCR4, indicating that this is an activated form of the receptor. The significance of P338-CXCR4 antibody staining is not clear. There was no regulation of this phosphorylation site by CXCL12 in in vitro studies. The lack of P338-CXCR4 staining in vascular endothelium and the minimal staining in low grade lesions indicates, however, that this phosphorylation can be regulated, is not a prerequisite for P339 phosphorylation, and may be a feature of increasing malignancy.

In all grades of astrocytomas CXCR4 was present and activated. These findings suggest that CXCR4 plays a role in tumor biology regardless of the degree of malignancy and broaden the scope of potential CXCR4 functions in cancer. At present, the focus of most cancer-related CXCR4 research is on the relationship between CXCR4 and features of malignancy, such as tumor cell motility and metastatic behavior (2), or, more recently, angiogenesis (51). Rempel et al. (45) described CXCL12 and CXCR4 expression in GBM and suggested that the expression was related to necrosis and angiogenesis. The regulation of CXCL12 and CXCR4 expression by hypoxia (46) or vascular endothelial growth factor (47, 48) is consistent with this hypothesis. However, we observed a more diffuse pattern of CXCR4 staining in GBM and medulloblastoma samples (3) and now report CXCR4 expression in lower-grade astro-cytomas as well.

Invasiveness is not a feature of grade 1 astrocytomas and necrosis is not a feature of astrocytomas grades 1 to 3 (52). Although angiogenesis may be necessary for all tumor growth, microvascular proliferation is not encountered in astrocytomas below grade 4 (24). Therefore, the expression of CXCL12 and CXCR4 cannot be strictly related to invasion, hypoxia, necrosis, or angiogenesis, and the functions of CXCR4 cannot be confined to mediating malignant behavior alone. Rather, the diffuse expression of CXCR4, together with the effects of AMD3100 on intracranial xenograft growth (3), suggests that CXCR4 regulates tumor cell growth regardless of grade. This does not necessarily mean that CXCR4 has equivalent function in all grades of astrocytoma or other cancers. The EGF and platelet-derived growth factor (PDGF) receptors are similarly present in both low- and high grade astrocytomas but increased tumor grade is associated with increased expression of either receptor (37, 53-55). The level of receptor expression may affect the strength of receptor signals and determine the pattern of receptor-mediated effects.

We found that the fraction of CXCR4 that was present in a phosphorylated state was increased in the diffuse astrocytomas compared with the grade 1 tumors. In normal human brains, as well as in all tumor cases, the phosphorylation of CXCR4 on serine 339 was only observed in association with CXCL12. This supports the hypothesis that ligand activation of CXCR4 is the predominant mechanism for regulating its activity. In vitro studies suggest that EGF receptor activation can also induce CXCR4 phosphorylation. EGF receptor activation is a prominent feature in glioblastomas (grade IV) and thus would be expected to frequently occur in proximity to CXCR4 (29, 30). The ability of EGF to stimulate CXCR4 phosphorylation and potentially modulate its signaling therefore raises the possibility that the role of CXCR4 in astrocytomas, or other EGF receptor-expressing cancers, may also be linked to EGF receptor function. In support of potential CXCL12 independent activation of CXCR4, increasing tumor grade correlated with a decreased ratio of CXCL12 to P339-CXCR4. It remains to be determined whether other receptor tyrosine kinases that are frequently activated in astrocytomas such as PDGF receptor (37-40) or IGF-1 receptor (41) can also promote CXCR4 phosphorylation.

Multiple kinases are known to phosphorylate GPCRs including GRKs, PKC and Akt (42). We demonstrated that CXCL12 and EGF treatment as well as PKC activation could induce CXCR4 phosphorylation. PKC phosphorylation of CXCR4 can regulate internalization, however in previously published studies, it appeared to involve a mechanism distinct from CXCL12 induced endocytosis (17-19). Data presented here suggest that S339 may serve as an integration point for multiple intracellular pathways in the regulation of CXCR4 signaling and internalization. It is interesting to consider that the regulation of CXCR4 internalization and signaling through the activation of other receptors could alter its functions in malignancy. CXCR4 activation of the heterotrimeric G protein Gi is stimulated by ligand and inhibited by β-arrestin binding (20, 21). β-arrestin bound to CXCR4 can serve as a scaffold for the binding of RAF and MEK and therefore this does not terminate the activation of the MAP kinase pathway (43, 44). Serine 339 phosphorylation is a regulatory step in arrestin binding. Therefore if the activity of other receptors affects S339 phosphorylation and β-arrestin binding this could alter the balance of heterotrimeric G protein dependent and independent signals downstream of CXCR4 activation.

These data extend previous findings in which we described CXCR4 and CXCL12 expression in a neural tumor, medulloblastoma, as well as in GBM (3). These data suggest that stromal factors, such as CXCL12 may play critically important roles in tumor formation and growth, and CXCR4 antagonist therapy may be broadly applicable to patients with brain tumors.

The following materials and methods were used in examples 5-10.

Chemicals, reagents, and antibodies. All chemicals were obtained from Sigma (St Louis, Mo.) unless otherwise indicated. All tissue culture reagents and media were obtained from Invitrogen (Carlsbad, Calif.) unless otherwise indicated. Antibodies were obtained from Cell Signaling (Beverly, Mass.) except antibodies directed against the following antigens: CXCR4— monoclonal antibody was from R&D (Minneapolis, Minn.), CXCR4 polyclonal antibody from Leinco (St Louis, Mo.), CXCL12 from Peprotech (Rocky Hills, N.J.), β-actin from Sigma, CD45 and CD68 from DakoCytomation (Carpenteria, Calif.), GRK2 from Abcam (Cambridge, Mass.), and IgG isotype controls from Jackson ImmunoResearch (West Grove, Pa.). A novel phospho-CXCR4 specific antibody (pCXCR4) was prepared and purified in our laboratory as previously described (60).

Human Tissue samples. Paraffin-embedded optic pathway glioma specimens from patients with Neurofibromatosis Type 1 (three) and brain autopsy specimens (three from children less than 1 year of age, two from an 11 and a 12 year old) were retrieved from the archives of the Department of Pathology at the Washington University School of Medicine in accordance with an Institutional Review Board approved protocol for the use of human pathology specimens.

Tissue sections and immunohistochemistry. Tissue preparation and staining was performed as previously described (60). Sections (5 µm) were deparaffinized in xylene and rehydrated in a series of alcohols of decreasing concentration. Endogenous peroxidase was blocked with 3% $H_2O_2$ in TBST (10 mM Tris pH 8.0, 0.15M NaCl, 0.05% TWEEN) and non-specific avidin/biotin binding sites were blocked with Vector Blocking kit (Vector Laboratories Burlingame, Calif.). Sections were additionally blocked with 10% serum from the animal source of the appropriate corresponding secondary antibody diluted in incubation media (0.1 M Tris (pH 7.5), 0.15 M NaCl, 2% non-fat dry milk and 0.1% Triton-X 100) and incubated in primary antibody overnight at 4° C. Primary antibody concentrations were as follows: CXCR4 in human tissue, mouse monoclonal antibody (1 µg/ml) and in mouse tissue, rabbit polyclonal antibody (1:200), CXCL12 (1:66), β-Actin (1:2000), CD 45 (1:100), CD68 (1:100) and pCXCR4 (1:66). Immunoreactive complexes were detected using the corresponding secondary biotin-conjugated antibodies augmented by streptavidin-horseradish peroxide and visualized by DAB supplied by DakoCytomation. Slides were then counterstained with hematoxylin, dehydrated through a series of alcohols and xylene, and coverslipped in 50:50 xylene/Permount. Control sections were incubated with isotype-matched IgG.

Culture and treatment of primary astrocytes. Primary cultures of astrocytes were prepared from post-natal day two $Nf1^{flox/flox}$ mice as previously described (134) and in accordance with established Animal Studies Protocols at Washington University School of Medicine. Cultures were infected with adenovirus containing either Cre recombinase (Nf1−/−) or LacZ (Nf1+/+). Primary cultures of astrocytes were grown under standard adherent conditions in serum free media (DMEM/F12 or Neurobasal (Gibco-BRL)) in the presence or absence of 0.1 µg/ml CXCL12 (Peprotech) and 10 µM Forskolin for 24 hours, as indicated. Cell number was determined after 24 hours by trypan blue exclusion and the growth effects of CXCL12 were derived as follows: ((cell number in the presence of CXCL12—cell number cell in the absence of CXCL12)/cell number in the absence of CXCL12)×100.)

Western Blot Analysis. Whole-cell extracts were obtained by lysing cells with lysis buffer (20 mM Tris pH 7.4, 137 mM NaCl, 10% Glycerol and 1% Triton-X-100) supplemented with phosphatase inhibitor cocktail set II (Calbiochem, La Jolla, Calif.), PMSF (1 mM), leupeptin, (0.005 mg/ml) and aprotinin (0.005 mg/ml). The proteins were resolved with 10% Bis-Tris gels (Invitrogen) and transferred onto the nitrocellulose membrane Hybond ECL (Amersham, Piscataway, N.J.) according to standard protocols. Membranes were incubated with polyclonal antibodies CXCR4 (1:500), pErk½ (1:1200), pan Erk½ (1:150), pAkt (1:500), pan Akt (1:1000), pGRK2 (1:250), and pCXCR4 (1:200) overnight at 4° C. This was followed by incubation with horseradish peroxidase-conjugated secondary antibody (1:15,000; Bio-Rad). Peroxide activity was detected using the enhanced chemiluminescence Supersignal West Dura system (Pierce, Rockford, Ill.) Mouse anti-actin antibody was used as a loading control. Quantitation of western blots was performed by densitometry using Image J software from the NIH.

cAMP measurements. cAMP was measured by ELISA (Cayman Chemical Company, Ann Arbor, Mich. or Assay Designs, Ann Arbor, Mich.). Briefly, astrocyte cultures were lysed in 0.1 N HCl. After the removal of cellular debris, soluble cellular extract was dried down and resuspended in EIA buffer. Experimental samples and cAMP standard curve were acetylated to increase the sensitivity of the assay and incubated with cAMP ACHe tracer and cAMP EIA antiserum overnight at 4° C. according to the manufacturer's instructions. After extensive washing, bound antibody was measured by spectrophotometric analysis. Concentrations of cAMP were derived from comparison with standard curve according to manufacturer's instructions.

Cell Cycle Analysis. Ethanol fixed cells were washed in PBS and resuspended in PI staining solution containing 0.1% Triton-X-100, 0.2 mg/ml RNase A, and 20 ug/ml Propidium Iodide in PBS. The cells were incubated for 15 minutes at 37° C., in the dark. Flow Cytometry was performed on a FACS-Calibur system (Becton Dickinson, San Jose, Calif.) Data were analyzed using CellQuest software (Becton Dickinson, San Jose, Calif.). Aggregates and debris were excluded from the analysis.

Example 5

CXCR4 is Present in a Ligand-Induced Phosphorylated Form in NF1-Associated OPG.

Neurofibromatosis type 1 (NF1) is an autosomal dominant tumor predisposition syndrome that affects approximately 1:3000 people worldwide (110). Individuals with NF1 are susceptible to a variety of neoplasms, but they are especially prone to the development of benign and malignant tumors of the peripheral and central nervous systems (111). Approximately 15% of patients with NF1 develop low-grade astrocytomas with strong anatomic and temporal associations in the pattern of their formation (112). Gliomas in NF1 most frequently occur between the retina and the optic chiasm, in a pattern referred to as "optic pathway" glioma (OPG). Remarkably, OPG typically grow in young children and rarely progress after ten years of age, regardless of treatment. These observations raise the possibility that the growth of OPG in NF1 is developmentally regulated, and suggests that control signals from the surrounding brain may exist that dictate when tumors are mostly likely to develop and grow. The molecular basis for this unique pattern of OPG growth in patients with NF1 has not been identified.

NF1-associated gliomas arise from a transformed glial fibrillary acidic protein (GFAP) positive cell (astroglial cell) in which there is homozygous NF1 inactivation and loss of neurofibromin expression (113-115). Individuals with NF1 are born with one non-functional NF1 allele, and loss of the second (non-mutated) NF1 allele presumably occurs randomly to lead to tumor formation. However, the natural history of NF1-associated OPG indicates that a non-random process also influences where and when tumors form. Two recently described genetically engineered models (GEM) of NF1-associated OPG indicate that glioma formation in NF1 requires additional factor(s) that derive from the Nf1+/− brain. (116, 117) Complete loss of neurofibromin expression alone in GFAP expressing cells ($Nf1^{flox/flox}$; GFAP-Cre) is insufficient for glioma formation (118), whereas targeted loss of neurofibromin in GFAP-expressing cells, in the context of an Nf1+/− brain ($Nf1^{flox/mut}$; GFAP-Cre; Nf1+/−$^{GFAP}$CKO), similar to what occurs in patients with NF1, results in glioma formation. These tumors form along the optic nerve in young mice in which tumor cell proliferation is maximal between 3 weeks and 2 months and greatly reduced after 4 months of age (116, 119). Similarly, constitutive activation of K-RAS in GFAP astroglial cells results in hyperproliferation of astrocytes, but no glioma development (117). In contrast, activation of K-RAS in GFAP positive cells, in the context of an Nf1+/− brain (Nf1+/−; K-RAS$^{GFAP}$) results in the formation of optic pathway gliomas. These observations strongly suggest that either astroglial cell Nf1 inactivation or K-RAS activation mimicking neurofibromin loss is not sufficient for OPG formation, but must instead work cooperatively with developmentally-regulated, growth-promoting signal(s) that originate from the surrounding Nf1+/− optic pathway.

Neurofibromin is a large protein that contains a domain with significant homology to proteins that function as GTPase activating proteins (GAPs) for the RAS proto-oncogene (120-126). These proteins are negative regulators of RAS function. Consistent with this function, loss of neurofibromin is associated with hyper-activation of RAS (117, 127-131). In addition to RAS inhibition, neurofibromin is a positive regulator of cAMP generation (132), and its loss is also associated with decreased production of cAMP in both mammalian neurons and astrocytes (133-134).

The chemokine CXCL12 and its receptor CXCR4 represent compelling candidate cofactors for NF1-associated OPG formation. CXCL12 and CXCR4 are important patterning agents during normal brain development (135). In addition, paracrine activation of CXCR4 is necessary for malignant neural and astrocytic tumor xenograft growth in vivo (3), and CXCR4 is a $G\alpha_i$ coupled receptor, whose activation results in both increased RAS activation and decreased levels of intracellular cAMP (136). In the present study, we examine the hypothesis that optic pathway-derived CXCL12 activation of CXCR4 acts cooperatively with neurofibromin loss in astroglial cells to predispose children with NF1 to astrocytoma formation along the optic pathway.

To evaluate the potential role of CXCL12 and CXCR4 in NF1-associated gliomagenesis, we analyzed OPG specimens from three patients with NF1 for expression of CXCL12 and CXCR4. In all cases, we recognized three cellular sources of CXCL12 within these tumors. Similar to what we had observed for sporadic low and high-grade astrocytomas as well as for medulloblastomas (3, 60), CXCL12 was abundantly expressed in the endothelium of tumor-associated blood vessels (FIG. 7A (e)). In addition, CXCL12 staining was evident in neuronal cellular processes expressing neurofilament 160, and represented entrapped axons, a common feature in OPGs (compare FIGS. 7B and 7C). In addition, CXCL12 was detected in cells that were identified as parenchymal microglia by their expression of CD68 (compare FIGS. 7D and 7E). Similar to our previous findings in astrocytomas and medulloblastoma, CXCR4 was abundantly expressed in tumor cells in a ligand-induced phosphorylated form (FIG. 7F) (60). These results demonstrate that proximity of these multiple sources of CXCL12 to tumor cell CXCR4 comprises a functional paracrine relationship for CXCR4 activation. Intratumoral CXCL12 was also evident in OPG specimens derived from two GEM of OPG, Nf1+/$-^{GFAP}$CKO and Nf1+/-; KRAS$^{GFAP}$ mice (FIGS. 7G and 7H).

Example 6

CXCL12 Expression in the Brain Correlates with the Temporal Pattern of OPG Growth The expression of CXCL12 and CXCR4 in NF1-associated OPG suggests that CXCL12 might play a role in OPG growth analogous to its role in promoting malignant brain tumor growth. To determine if CXCL12 might also contribute to the pattern of glioma formation in NF1, CXCL12 expression was examined in the brains of human infants and adolescents (FIG. 8). In children less than 1 year of age, CXCL12 expression was localized in vascular endothelium and ependymal cells throughout the brain and the pia mater overlying the external granule cell layer of the cerebellum. In contrast, expression of CXCL12 in cells with distinctive neuronal morphology was more circumscribed and was most evident in the suprachiasmatic portion of the hypothalamus and in scattered neurons throughout the cortex. In previous studies, these areas had also been identified as rich sources for CXCL12 (reviewed in (137)). Interestingly, neuronal CXCL12 expression was significantly less in all brain areas in the 11 and 12 year old human brain with the exception of the cortex.

Since Nf1-/- astroglial cell proliferation is maximal at 3 weeks of age and declines by 3-4 months of age in mouse OPG models (116, 119), we examined CXCL12 expression in the brains of 3 week and 3 month old mice. As observed in the human brains, endothelial and ependymal staining was noted throughout the mouse brain at 3 weeks of age with neuronal staining in the cortex, hypothalamus and pons, which was markedly reduced by 3 months of age (data not shown). Moreover, this developmental pattern of CXCL12 was confirmed by quantitative RT-PCR in several brain regions (data not shown). These data indicate that levels of CXCL12 mRNA and protein expression correlate with the temporal aspects of NF1-associated glioma growth.

Example 7

Neurofibromin Loss Confers a CXCL12-Mediated Growth Advantage in Astrocytes

To determine the biological significance of CXCR4 activation to NF1 glioma biology, we next sought to evaluate the regulation of CXCL12 growth effects by neurofibromin in astrocytes. While the true cell of origin of astrocytomas remains unknown, we utilized primary cultures of cortical astrocytes as a model of a normal counterpart to astrocytoma cells. Astrocytes were derived from Nf1$^{flox/flox}$ mice and rendered Nf1+/+ or Nf1-/- by infection with adenovirus encoding LacZ or Cre recombinase, respectively. In all experiments, infection with Ad5-Cre resulted in >95% reduction in neurofibromin expression as determined by Western blot (data not shown). Although Nf1+/+ and Nf1-/- astrocytes express comparable levels of CXCR4 (FIG. 9A), markedly different growth responses to CXCL12 were observed. As previously reported, Nf1-/- astrocytes were found to grow more rapidly than Nf1+/+ astrocytes (data not shown). In addition, Nf1-/- astrocytes responded to low doses of CXCL12 (0.1 ug/ml or ≈10 nM) with an increase in cell number of nearly 14+/-2%, while Nf1+/+ astrocytes, treated under identical conditions, consistently showed a 10+/-5% decrease in cell number, when compared to untreated controls (FIG. 9B).

The basis for the in vitro growth effects of CXCL12 was further evaluated by cell cycle analysis of asynchronously growing cultures of Nf1+/+ and Nf1-/- astrocytes in the presence and absence of CXCL12. In agreement with measurements of cell number, 15% more Nf1-/- astrocytes were in the S+G$_2$M fraction of the cell cycle compared to Nf1+/+ astrocytes (P<0.005, data not shown). This decrease in Nf1+/+ cell number in response to CXCL12 was the result of both a 6% decrease in proliferation (S+G$_2$-M) and a 38+/-8% increase in apoptosis (sub-G$_0$). The increase in Nf1-/- cell number was the result of a 27+/-12% decline in apoptosis alone (FIG. 9C).

Example 8

CXCR4-Mediated Survival Requires Intracellular Events in Addition to the Activation of Erk½

Astrocyte growth has been linked to the activation of Erk½ (138) and PI3 kinase activation (139), and Nf1-deficient astrocytes exhibit high levels of RAS pathway activation (117). Consistent with these observations, treatment with the MEK inhibitor PD98059 or the PI3-kinase inhibitor wortmannin prevented growth of both Nf1+/+ and Nf1-/- astrocytes (data not shown). To determine whether differences in the activation of Erk½ or PI3 kinase were responsible for the difference in CXCL12 effects on Nf1+/+ versus Nf1-/- astrocyte growth, we evaluated time-dependent changes in Erk½ and Akt activation (phosphorylation) after treatment with CXCL12. Consistent with the known functions of neurofibromin, there was increased phosphorylation of Erk½ at baseline in Nf1-/- relative to Nf1+/+astrocytes (FIG. 10A). However, here was no effect of Nf1 loss on the magnitude of CXCL12-induced phosphorylation of Erk½ or Akt.

The absence of significant differences in the activation of Erk½ and Akt in response to CXCL12 treatment suggested that additional intracellular events must account for the differences in growth responses of Nf1+/+ and Nf1-/- astrocytes to CXCL12. We evaluated the time dependent changes in intracellular cAMP in Nf1+/+ and Nf1-/- astrocytes after exposure to 0.1 µg/ml CXCL12. In both types of astrocytes, cAMP levels rapidly declined in response to CXCL12. However, in Nf1+/+ astrocytes, intracellular levels of cAMP rapidly recovered to baseline and oscillated between baseline and 40% of baseline over the 45-minute experimental period (FIG. 10B). In contrast, levels of cAMP in Nf1-/- astrocytes remained suppressed for a longer period of time and rose only once during the 45-minute period, peaking at approximately 85% of baseline. The integrated areas under each curve were significantly different (Nf1+/+ astrocytes=2.70; Nf1-/- astrocytes=1.96), indicating a reduction in intracellular cAMP in Nf1−/− astrocytes to approximately 73% of that observed in Nf1+/+ astrocytes. These results are similar to the magnitude of reduced intracellular cAMP generation previously reported in Nf1−/− astrocytes in response to PACAP treatment (134).

Example 9

Growth Response to CXCL12 is Dependent Upon the Suppression of cAMP

The above data indicate that Nf1−/− astrocyte growth in response to CXCL12 requires MEK and PI3 kinase activation and is associated with CXCL12-induced changes in intracellular cAMP levels. We hypothesized that if cooperative signaling between Nf1 loss and CXCR4 activation promotes tumor formation through the suppression of cAMP, then agents that alter intracellular cAMP should modulate CXCL12 responses. We treated astrocytes with the adenylyl cyclase (AC) activator forskolin in the presence and absence of CXCL12. As described above, baseline cAMP levels in Nf1+/+ and Nf1−/− astrocytes are comparable (approximately 3 pmol/mg of total protein). In these experiments, forskolin elevated intracellular cAMP levels in both Nf1+/+ and Nf1−/− astrocytes with peak values of 17.8+/−0.4 and 19.4+/−4.5 pmol/mg of protein, respectively, after 24 hours of treatment. The effect of forskolin was not abrogated by cotreatment with CXCL12. Under these conditions, cAMP levels were 17.9+/−2.5 and 10.4+/−5.8 pmol/mg of total protein in Nf1+/+ and Nf1−/− astrocytes, respectively. Moreover, we found that forskolin decreased Nf1+/+ astrocyte number and blocked the CXCL12 growth-promoting effects in Nf1−/− cells (FIG. 11A). The effect of forskolin on CXCL12-mediated Nf1−/− apoptosis was evidenced by changes in the percentage of Nf1−/− astrocytes in the sub-$G_0$ fraction of the cell cycle (FIG. 11B). Thus while astrocyte growth is dependent upon MEK and PI3 kinase activity, CXCL12-induced Nf1−/− astrocyte growth requires the suppression of intracellular cAMP levels.

Example 10

Enhanced CXCL12-Induced cAMP Suppression is Associated with Decreased CXCR4 Phosphorylation Among the primary mechanisms for controlling GPCR effects on cAMP production is receptor desensitization (140). This process is initiated when ligand occupied GPCR (e.g., CXCR4) is phosphorylated by G protein receptor kinase (GRK). Phosphorylation of CXCR4 promotes the binding of arresting, thereby blocking the activation of heterotrimeric G proteins and the downstream modulation of adenylyl cyclase activity (141). We evaluated time-dependent changes in CXCL12-induced CXCR4 phosphorylation and found that CXCR4 phosphorylation was decreased in Nf1−/− astrocytes compared to Nf1+/+ astrocytes (FIG. 12A). While CXCL12 induced a 2.6+/−0.06 fold increase in pCXCR4 at 5 minutes in wild-type astrocytes, there was a 0.56+/−0.14 fold decrease in pCXCR4 in Nf1−/− astrocytes.

Decreased GRK dependent phosphorylation could arise from changes in GRK expression or increased inhibition of GRK activity (142). GRK2 has been demonstrated to phosphorylate CXCR4 (143) and can itself be inhibited by ERK-mediated phosphorylation on serine 670 (144). As ERK activity is increased as a result of neurofibromin loss, we evaluated whether there was an increase in phospho-GRK2 in Nf1−/− compared to Nf1+/+ astrocytes. We found that decreased pCXCR4 in Nf1−/− astrocytes was associated with a 3.0 fold increase in phosphorylation of GRK2 on serine 670 relative to wild-type astrocytes (FIG. 12B). This finding is consistent with ERK-dependent inhibition of GRK2, suggesting that loss of neurofibromin results in decreased CXCR4 desensitization and enhanced CXCL12-induced cAMP suppression, culminating in increased Nf1−/− astrocyte growth.

The natural history of NF1-associated OPG in both humans and genetically-engineered mouse models of NF1 indicate that tumor formation and growth are dependent upon factor(s) derived from the surrounding brain microenvironment. Tumor formation in humans affected with NF1 displays both anatomic and temporal specificity, with the majority of tumors forming along the optic pathway in young children (112, 145, 146). This is in contrast to the pattern of spontaneously-arising pilocytic astrocytomas in which the cerebellum is the most commonly affected region of the brain, an area that is rarely involved in NF1-associated glioma. These observations suggest that region-specific signals can influence the pattern of brain tumor growth. A requirement for such region-specific signals in gliomagenesis is supported by studies of mouse models of NF1-associated OPG, in which astroglial Nf1 loss is insufficient for glioma formation unless coupled with an Nf1+/− brain microenvironment (116). In addition, in both humans and mice, NF1-associated gliomas form early in life and commonly stop growing by adolescence. Together, these observations suggest that neurofibromin loss is necessary, but not sufficient for tumor formation, and that tumor growth is dependent upon environmental signals whose expression is developmentally regulated during childhood.

We reasoned that CXCL12 was a promising candidate for a brain-derived factor whose actions could partner with neurofibromin loss to promote OPG formation and growth. This hypothesis was based on CXCL12 and CXCR4's patterning functions during normal CNS development (137) and their importance in supporting malignant brain tumor growth (3). Furthermore, CXCR4 is a $G\alpha_i$-coupled G-protein coupled receptor whose normal functions to activate RAS and suppress cAMP would be enhanced by the known consequences of neurofibromin loss (136).

To determine whether CXCL12 could explain the temporal and spatial pattern of NF1-associated brain tumor formation, we examined CXCL12 expression in unaffected brains and OPG specimens from young and older humans and mice. In mouse and human brains, axons within the optic nerve and neurons of the suprachiasmatic hypothalamus expressed CXCL12. Moreover, CXCL12 expression in these locations was developmentally regulated. While there was significant CXCL12 expression in the optic nerve and hypothalamus of young children, there was little expression in these regions in specimens at pubescence. Similarly, immunohistochemical and quantitative PCR for CXCL12 expression in mouse brain indicated that age dependent decreases in expression occurred in both wild-type and Nf1+/− mouse brains. These findings support the hypothesis that CXCL12 influences glioma growth along the optic pathway in NF1, and that the decrease in neuronal CXCL12 expression, especially within entrapped axons, may be responsible for the age-dependent decline in tumor growth observed in patients with NF1.

These observations do not immediately support a role for CXCL12 in the preferential formation of these tumors along the optic tract. The expression of CXCL12 in other brain regions such as the cortex is contrary, but does not rule out, a role for CXCL12 alone in dictating where these tumors form. In future studies, we will determine whether there are differences in the bio-availability of CXCL12 in different brain regions and between wild-type and Nf1+/− mice. In addition, we will ascertain whether Nf1+/− microglia function in a fashion that is analogous to that proposed for Nf1+/− mast cells in dermal neurofibroma (147, 148), and display enhanced recruitment to different sites of glioma formation, and produce higher levels of growth factors like CXCL12.

Previous studies have focused on the consequence of neurofibromin loss on the proliferation of Nf1−/− astrocytes (149, 150). While increased astrocyte proliferation resulting from RAS pathway activation clearly contributes to the growth advantage observed in Nf1−/− astrocytes, the impact of CXCL12 on Nf1−/− astrocyte growth is largely a reflection of decreased astrocyte apoptosis. The combination of increased astrocyte survival and increased astrocyte proliferation resulting from neurofibromin loss provides a synergistic signal that could lead to transformation and OPG formation.

The growth effects of CXCL12 were uniquely dependent upon the suppression of cAMP, which was enhanced in Nf1−/− relative to Nf1+/+ astrocytes, and was blocked by forskolin. CXCR4 is a $G\alpha_i$ coupled GPCR that suppresses intracellular cAMP through the inhibition of adenylyl cyclase (AC). The ability of CXCR4 to inhibit AC can be counter-regulated by the actions of Regulators of G Protein Signaling (151) and receptor desensitization (152). Desensitization involves the phosphorylation of the ligand-occupied receptor and subsequent binding of arrestins which block heterotrimeric G protein activation and signaling, resulting in inhibition of CXCR4-mediated downregulation of AC activity. We found that neurofibromin loss enhanced the suppression of cAMP downstream of CXCR4 activation by inhibiting CXCR4 desensitization. We further identified ERK-dependent inhibition of GRK2 as the molecular basis for the Nf1−/− astrocyte loss of CXCR4 desensitization. ERK is a physiologic regulator of GRK2 activity, producing inhibition of kinase activity through phosphorylation (144). Loss of neurofibromin results in hyperactivation of the RAS-MAPK pathway and increased activation of ERK, resulting in increased inhibition of GRK2. Changes in GRK activity have been described in a variety of diseases including thyroid cancer (153). To our knowledge, this is the first demonstration of inhibition of GRK activity as a direct result of mutation in a tumor suppressor gene.

In contrast to the behavior of most tumors, OPGs in NF1 typically stop growing spontaneously. Most patients experience remission from their OPGs as they approach puberty, suggesting that tumor growth is regulated by a factor(s) whose activity declines as a function of age. The in vivo expression data and in vitro growth data presented here are consistent with the hypothesis that CXCL12 stimulates glioma growth along the optic pathway in a developmentally-regulated fashion. Collectively, these studies provide the first mechanistic explanation for the unique pattern of NF1-associated OPG growth, and suggest that glioma growth is ligand-dependent and involves cAMP-mediated growth control pathways. These findings raises the exciting possibility that similar mechanisms may underlie the formation and growth of other pediatric brain tumors with distinct patterns of formation, such as medulloblastoma, and suggests that these pathways may represent additional targets for therapeutic interventions.

The following materials and methods were used for examples 12-15.

All animals were used in accordance with an established Animal Studies Protocol approved by The Washington University School of Medicine Animal Studies Committee.

Tumor cell lines. Firefly luciferase-expressing U87 glioblastoma multiforme cells and Daoy medulloblastoma cells were a gift of Dr. Andrew Kung, Dana Farber Cancer Institute, Harvard Medical School, Boston, Mass. Additional U87 and Daoy cells were obtained from American Type Tissue Culture (Manassas, Va.). EGFP-luciferase expressing U87 and Daoy cells were generated via lentiviral infection with FUGW-FL as described (4, 56). Briefly, replication-deficient virus was produced by co-transfection of 293T cells with three viral-encoding plasmids using Fugene 6 (Roche, Basel Switzerland) according to the manufacturer's instructions. The plasmids were: 1) a packaging vector containing transgenes for EGFP and firefly luciferase, 2) a plasmid containing vesicular stomatitis virus coat protein for pseudo-typing, and 3) the Δpackaging vector. Viral particles were collected from 293T cell supernatants and applied to tumor cell cultures. EGFP expressing cells were sorted and collected by high speed fluorescence-activated cell sorting.

Brain tumor cell cultures. Cells were cultured in αMEM (Invitrogen, Carlsbad, Calif.) supplemented with 10% FCS (Biomedia, Foster City, Calif.) in the presence of penicillin streptomycin at 37° C. with 5% $CO_2$.

Primary astrocyte cultures. Primary astrocytes were cultured from 1 to 3-day-old BALB/C mice as described (57). The cortices were triturated into single cells in minimal essential medium (Invitrogen) containing 10% FCS, and then plated onto 75 $cm^2$ T-flasks (0.5 hemisphere/flask) for 10-14 days. Astrocytes were prepared by vigorous shaking of T-flasks overnight, removal of non-adherent cells, and isolation of the remaining adherent cells, with 0.1% trypsin.

Primary granule neuron cultures. Primary cultures of purified GPCs were prepared from 6 day-old BALB/C mice as described (58). Cerebella were dissected and meninges were removed. After incubation with 0.1% trypsin (Sigma) in HBSS with 125 units/ml Dnase (Sigma), 0.5 mM EDTA for 20 minutes at 37° C., cells were pelleted and washed three times with HBSS. The final cell suspension was passed through a 100 μM nylon mesh cell strainer (Falcon, Franklin Lakes, Mich.). Cells were diluted to 2×106 cells/ml in DMEM/F12 (Gibco BRL, Gaithersburg, Md.) supplemented with N2 (Gibco BRL), 20 mM KCl, and 36 mM glucose.

Growth factor and drug treatment. Following serum-starvation for 24 hours, astrocytes, granule cells, U87 cells and Daoy cells, were treated with 1 μg/ml CXCL12 (PeproTech), 2.5 g/ml AMD3465 (kind gift from Simon Fricker, AnorMED, Langley, BC, Canada) (200 μM Rolipram (Sigma), or 10 μM Forskolin (Sigma) as indicated.

PDE4A expression. U87 and Daoy cells (15,000 cells) were transiently transfected for 48 h with a plasmid encoding a transgene for the tet-off transactivator (tTA) alone (kind gift from Dr. Louis Muglia, Washington University School of Medicine, St. Louis, Mo.), a plasmid containing a transgene for tet-off regulated expression of phosphodiesterase 4A (PDE4A) alone (kind gift from Dr. James Cherry, Boston University, Boston, Mass.), or a combination of both plasmids, using lipofectamine (Invitrogen) according to the manufacturer's instructions. Plasmid DNA (2 μg) was mixed with lipofectamine (5 μl) per 35 $mm^2$ dish. Transfection proceeded for 9 hours prior to exchanging transfection media for αMEM supplemented with 10% FCS.

cAMP measurement in cell culture. cAMP concentration was measured using a Correlated-EIA™. Enzyme Immunoassay Kit (Assay Designs Inc. MI) according to the manufacturer's instructions. Briefly, U87 or Daoy cells were serum-starved for 24 hours, and treated with CXCL12 (1 μg/ml), Rolipram (200 μM), or forskolin (10 μM). Cells were lysed in 0.1M HCL and particulate matter was removed by centrifugation at >600×g for 10 min. The supernatants were dried down and resuspended in assay buffer.

cAMP measurement in tumor tissue. EGFP-expressing tumor tissue was removed under direct fluorescence microscopy and frozen in liquid nitrogen. Frozen tissue was weighed and homogenized with 10 volumes of 10% ice-cold trichloroacetic acid, then centrifuged for 10 min at 4000 rpm to remove precipitate. The supernatant was washed three times with 8 volumes of water-saturated ether. The aqueous phase was dried down and resuspended in cAMP assay buffer.

Determination of cAMP concentration. Competitive immunoassay for cAMP concentration was performed exactly as directed by the manufacturer. Absorbance at 405 nm was measured and cAMP concentrations were determined by calculation based on a standard curve. Protein concentrations were measured by colormetric assay (Bio-Rad, Hercules, Calif.) according to the manufacturer's directions. cAMP values were normalized to protein for each sample individually.

Generation of xenografts. Tumor cell lines were harvested in mid-logarithmic growth phase and resuspended in PBS. Homozygous NCR nude mice (Taconic Farms, Germantown, N.Y.)) were anesthetized with ketamine hydrochloride at 150 mg/kg and xylazine at 12 mg/kg (Phoenix Pharmaceuticals, St. Joseph, Mo.) via intraperitoneal injection. The cranium was exposed and a small hole was made with a size 34 inverted cone burr (Roboz, Gaithersburg, Md.). Mice were fixed in a stereotactic frame (Stoelting, Wood Dale, Ill.) and 50,000 cells in 10 µl of PBS were injected through a 27-gauge needle over 2 min at 2 mm lateral and posterior to the bregma and 3 mm below the dura. The incision was closed with Vetbond (3M St. Paul, Minn.).

In vivo drug treatment. Mice were imaged at least twice after implantation of cells to identify those with equivalent tumor growth rates. Two weeks after tumor cell implantation, cohorts of mice per experiment with approximately equivalent tumor bioluminescence were divided into equal control and treatment groups. Animals in AMD 3465 experiments received subcutaneous osmotic pumps (Alzet, Palo Alto, Calif.), used according to the manufacturer's instructions, loaded with 10 mg/ml AMD3465 in sterile PBS or PBS alone. The infusion rate was 0.25 µl/h (50 µg/day). For the experiments with Rolipram or caffeine, mice in the treatment groups received oral administration of Rolipram (5 µg/g/day) or caffeine (100 µg/g/day). The concentration of drug in the water was determined from daily measurements of water consumption by each animal over the course of seven days. Concentrations were adjusted based on water consumption to provide the prescribed dose.

Bioluminescence Imaging. For bioluminescence imaging of living animals, NCR nude mice bearing intracranial xenografts of firefly luciferase-expressing U87 or Daoy cells were injected intraperitoneally with 150 µg/g D-luciferin (Biosynth, Naperville, Ill) in PBS, anesthetized with 2.5% isoflurane, and imaged with a charge-coupled device (CCD) camera-based bioluminescence imaging system (IVIS 50; Xenogen Corp., Alameda, Calif.; exposure time 1-60 seconds, binning 8, field of view 12, f/stop 1, open filter). Signals were displayed as photons/sec/cm$^2$/sr (59). Regions of interest (ROI) were defined manually at 95% of the maximum pixel output using Living Image and IgorPro Software (Version 2.50) and data were expressed as total photon flux (photons/sec) (59). Generally, the first mouse images were obtained 24 hours following intracranial inoculation of tumor cells. Data were analyzed and plotted as the ratio of bioluminescence on a given treatment day over bioluminescence on the first day.

Immunohistochemistry. Human brain tumor tissue was retrieved from the pathology files at Washington University School of Medicine. Samples were used in accordance with an Institutional Review Board approved protocol for human research. Formalin-fixed, paraffin embedded tissue was processed and analyzed as described (60). CXCR4 was detected with a mouse monoclonal antibody (1 µg/mL, R&D systems, Minneapolis, Minn.) and CXCL12 was localized with a rabbit polyclonal antibody (1:66 dilution, Peprotech, Rocky Hill, N.J.). Phosphorylated CXCR4 was detected using our rabbit polyclonal antibody (1:66 dilution). Immunoreactive complexes were detected using the corresponding secondary biotin-conjugated antibodies augmented by streptavidin horseradish peroxide and visualized by 3,3'-diaminobenzidine supplied by DAKO (Carpinteria, Calif.).

Example 12

Phospho-CXCR4 is Present in Medulloblastoma Specimens

Nearly thirty years ago it was observed that higher grades of human brain tumors were associated with lower total adenylyl cyclase (AC) activity and decreased tumor cell cAMP (61, 62). It is now known that increased cAMP inhibits proliferation under most circumstances (63-66) and can also stimulate apoptosis (67-69). Thus, these earlier observations warrant re-evaluation as we search for therapeutic targets in our efforts to improve the outcome for patients with malignant brain tumors. Decreased AC activity and decreased intracellular cAMP could be the result of decreased AC expression or decreased AC activation. With respect to the latter, the expression of CXCR4 in malignant brain tumors is of particular interest. CXCR4 is a $G\alpha_i$-coupled chemokine receptor and therefore has the capacity to inhibit AC activity and decrease intracellular cAMP (3, 45, 60, 70). We and others have studied the expression and actions of CXCR4 in both neural and astrocytic brain tumors, and found that CXCR4 can stimulate tumor growth and spread (3, 70-73). We found that systemic delivery of AMD 3100, a small molecule antagonist of ligand activation CXCR4, blocked the intracranial growth of both glioblastoma and medulloblastoma xenografts (3). These studies validated CXCR4 as a therapeutic target for the treatment of malignant brain tumors, but they did not identify the critical intracellular events that underlie CXCR4-dependent brain tumor growth, or the intracellular pathways that are targeted by AMD 3100 action.

More recently, we developed a novel phospho-specific antibody that recognizes a ligand-induced form of CXCR4, and demonstrated that increased grade of astrocytoma is associated with increased CXCR4 phosphorylation (60). Activation of CXCR4 would be predicted to inhibit adenylyl cyclase and decrease intracellular levels of cAMP (74). Thus the association between increased tumor grade and ligand-activation of CXCR4 could mechanistically link the earlier observations that cAMP levels are negatively correlated with the degree of malignancy in brain tumors.

Here we report that CXCR4-dependent brain tumor growth is mediated through cAMP suppression and that the anti-tumor effect of the CXCR4 antagonist AMD 3465 can be accounted for by its ability to block CXCL12-induced cAMP suppression. Further, this anti-tumor effect is mimicked in vitro and in vivo by drugs that elevate cAMP. These studies are the first to implicate cAMP suppression as a critical growth-promoting event downstream of CXCR4 activation.

As such, they advance our efforts to improve brain tumor therapy by identifying cAMP elevation as a novel therapeutic strategy.

In human astrocytoma specimens, advanced histologic grade is correlated with increased phosphorylation of CXCR4 (60). To determine whether this might be a general feature of central nervous system malignancies, we performed a similar analysis of CXCR4 phosphorylation in the primitive neural tumor, medulloblastoma. Subtyping of medulloblastoma based on tumor histology has prognostic importance. There are three major histological subtypes of medulloblastoma—desmoplastic, classic, and anaplastic/large cell medulloblastoma. (75). Compared to the classic examples, desmoplastic medulloblastomas are associated with a slightly better clinical course, while anaplastic/large cell medulloblastoma are considerably more aggressive (76). Our analysis included a total of ten pediatric and adult cases comprising the three major histological variants of medulloblastoma (Table 2). In agreement with our previous studies of medulloblastoma and glioblastoma (3, 60), all specimens exhibited positive tumor cell staining for CXCR4 (data not shown) and endothelial cell staining for CXCL12 (FIG. 13A). The proximity of CXCL12 to CXCR4 was associated with the phosphorylation of CXCR4 (pCXCR4) in 5/10 specimens (FIG. 13B, Table 2). Phospho-CXCR4 staining distinguished normal from tumor tissue. For example, in a medulloblastoma that infiltrated into the choroid plexus, the degree of pCXCR4 staining suggested that the level of CXCR4 activation in the tumor far exceeded that of the normal tissue (FIG. 13C). In this limited series, none of the desmoplastic medulloblastomas contained pCXCR4, while 2 of 3 classic and 3 of the 4 anaplastic large cell specimens did (Table 2). This suggests that the level of pCXCR4 may correlate with aggressiveness in medulloblastoma.

TABLE 1

Tumor Characteristics

| Histology | age (years) | sex | CXCR4 | pCXCR4 |
|---|---|---|---|---|
| desmoplastic | 47 | F | 2 | 0 |
| desmoplastic | 51 | M | 3 | 0 |
| desmoplastic | 47 | M | 1 | 0 |
| classic | 2 | F | 2 | 2 |
| classic | 38 | F | 4 | 0 |
| classic | 10 | F | 2 | 3 |
| anaplastic | 2 | F | 1 | 2 |
| anaplastic | 7 | M | 2 | 2 |
| anaplastic | 29 | F | 2 | 3 |
| anaplastic | 10 | M | 1 | 0 |

0-4 refers to the percentage of tumor cells stained with antibody. 1 = 1-25%, 2 = 26-50%, 3 = 51-75% and 4 = 76-100%.

Example 13

CXCL12 Growth Effects are Associated with Sustained Suppression of cAMP

Figure 14A:
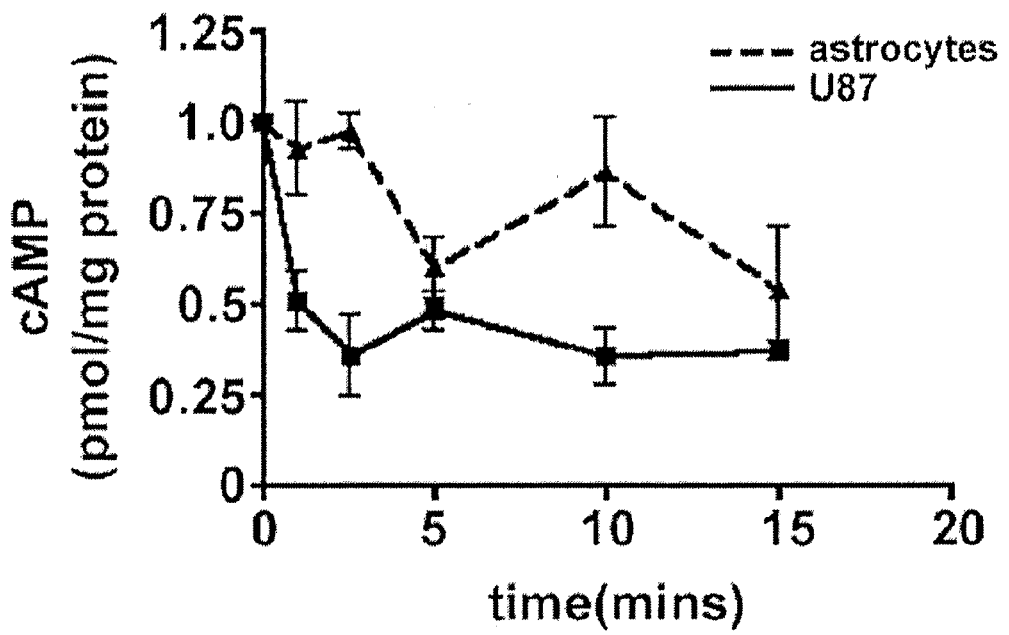
Figure 14B:
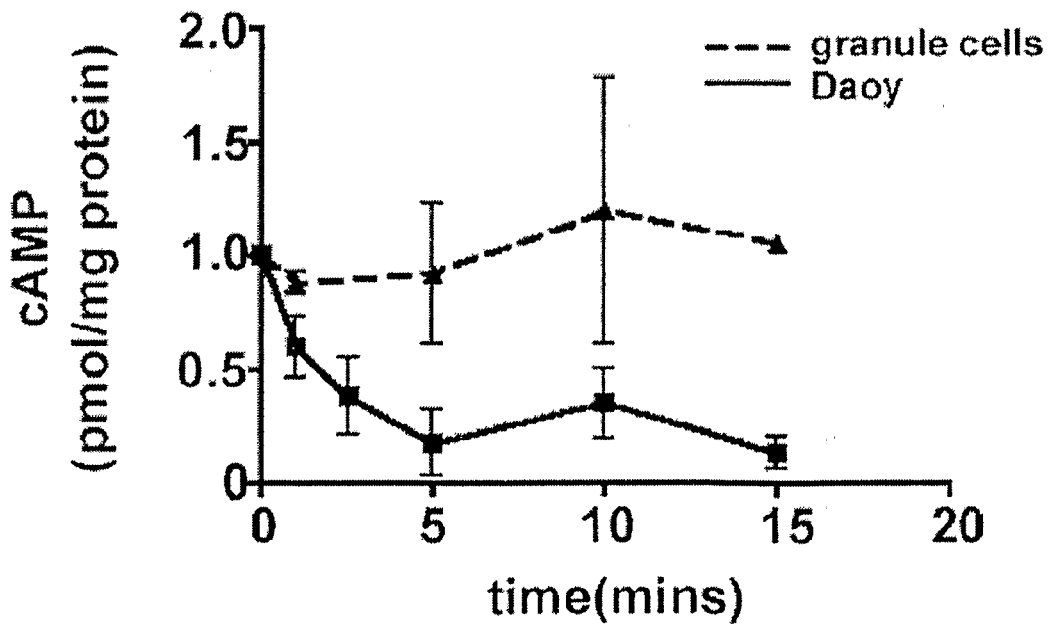

We investigated whether decreased levels of cAMP in brain tumors were related to increased CXCR4 activation, and whether there was enhanced CXCL12-induced cAMP suppression in neoplastic as compared to normal cells. To model tumor cell responses, we utilized U87 glioblastoma and Daoy medulloblastoma cell cultures. While the true cell of origin for glioblastoma and medulloblastoma is still controversial (77), we used primary cultures of cortical astrocytes and cerebellar granule precursor cells (GPCs) as normal counterparts for glioblastoma and medulloblastoma, respectively (78). When we measured time-dependent changes in intracellular cAMP after application of 1 µg/ml of CXCL12, we found that astrocytic cAMP fluctuated between baseline and 40% of baseline (FIG. 14A), while in GPCs there was little to no change in cAMP levels (FIG. 14B). The cAMP response in tumor cells was markedly different. Cyclic AMP levels rapidly declined in both U87 and Daoy cells and remained suppressed throughout the experimental period. Area-under-the-curve measurements indicated that in U87 cells there was a 45% reduction in intracellular cAMP as compared to astrocytes (FIG. 14A), while in Daoy cells cAMP was reduced by 70% as compared to GPCs (FIG. 14B). The differences in cAMP suppression were correlated with differences in CXCL12 growth effects. While CXCL12 (1 µg/ml) increased U87 (FIG. 14C) and Daoy cell (FIG. 14D) number by greater than 200%, it tended to decrease astrocyte cell number (FIG. 14C), and had no effect on GPC cell number (FIG. 14D). The correlation between sustained cAMP suppression and tumor cell growth suggests that suppression of cAMP may be a critical growth-promoting signal downstream of CXCR4 activation.

CXCL12 Growth Effects are Blocked by Elevation of Intracellular cAMP

Figure 15A:
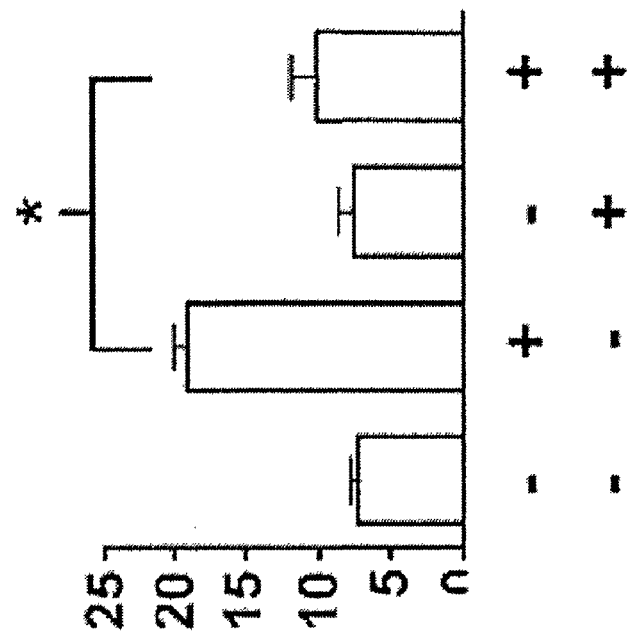
Figure 15A:
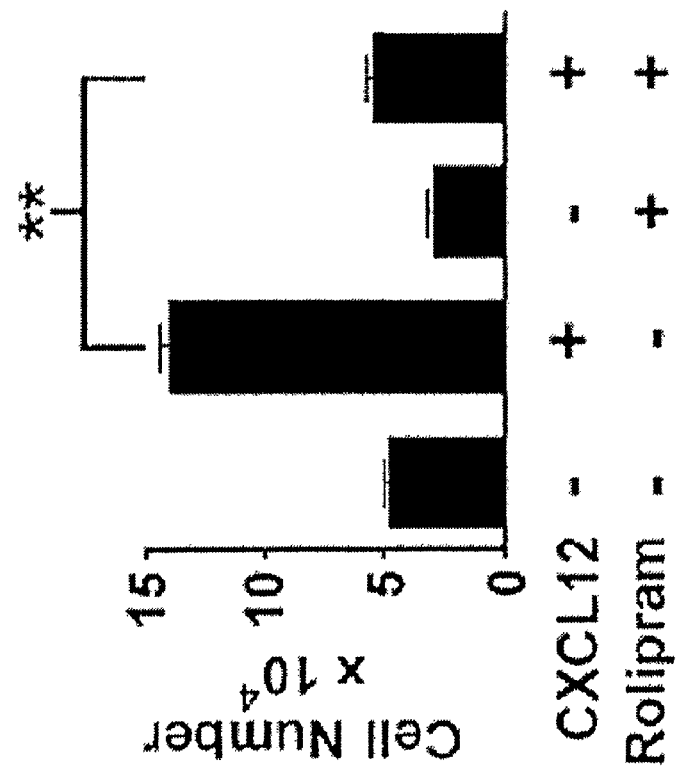
Figure 15B:
Figure 15C:
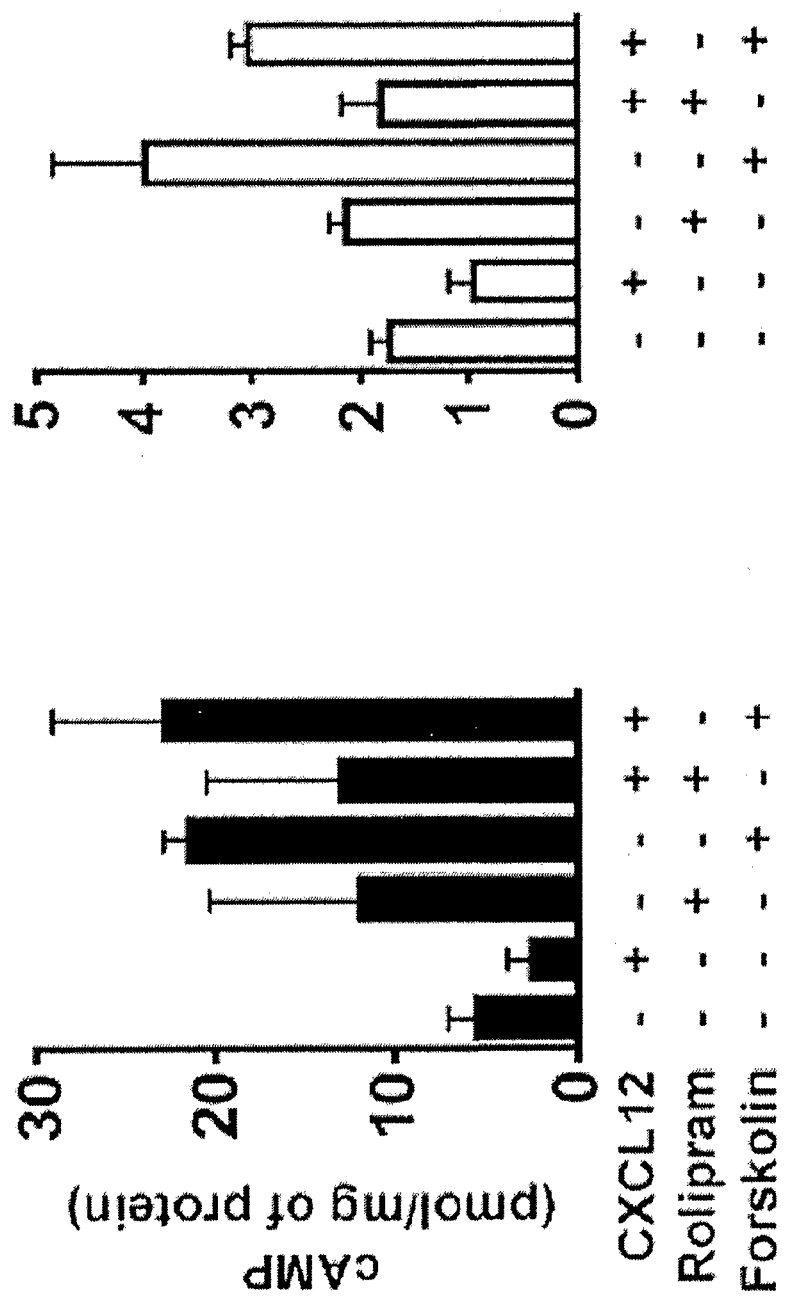

To further evaluate cAMP suppression as the basis for CXCR4-mediated tumor growth, we assessed the ability of drugs that elevate cAMP to block CXCL12 induced growth. Rolipram is a phosphodiesterase type 4 (PDE4) inhibitor that has been extensively evaluated in human clinical trials as an anti-depressant and as an anti-inflammatory agent, including inflammatory states of the central nervous system such as multiple sclerosis (79, 80). CXCL12 was again observed to increase U87 and Daoy cell number by greater than 2-fold (FIG. 15A). Treatment with Rolipram had little to no effect on U87 or Daoy cell number alone, but completely blocked the growth stimulation effects of CXCL12. Similarly the adenylyl cyclase activator forskolin also blocked CXCL12 growth effects in both cell lines (FIG. 15B). Treatment with Rolipram or Forskolin was associated with predictable increases in intracellular cAMP in both cell lines, and these effects were not abrogated by co-treatment with CXCL12 (FIG. 15C).

Example 14

Figure 16A:
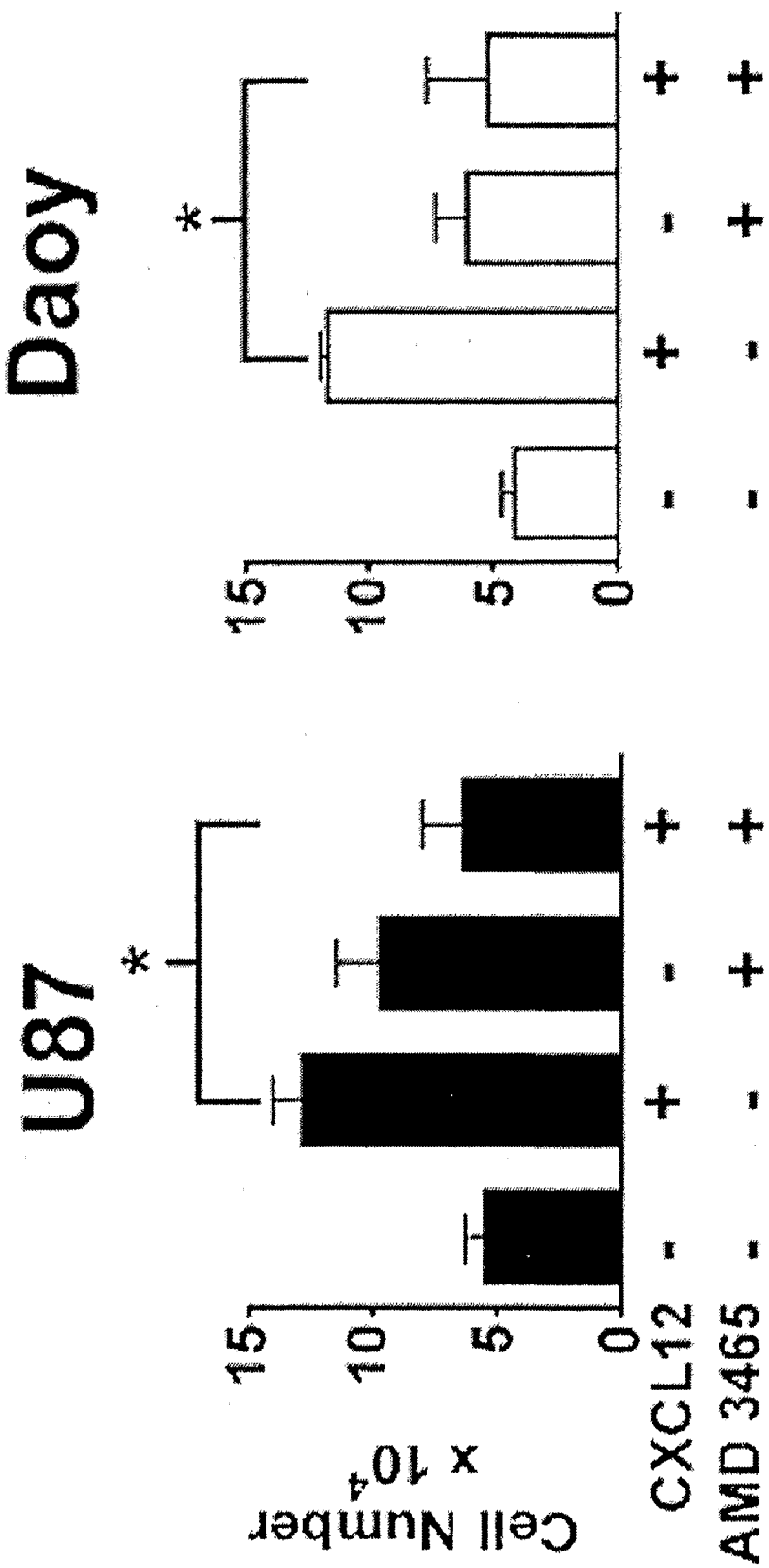
Figure 16B:
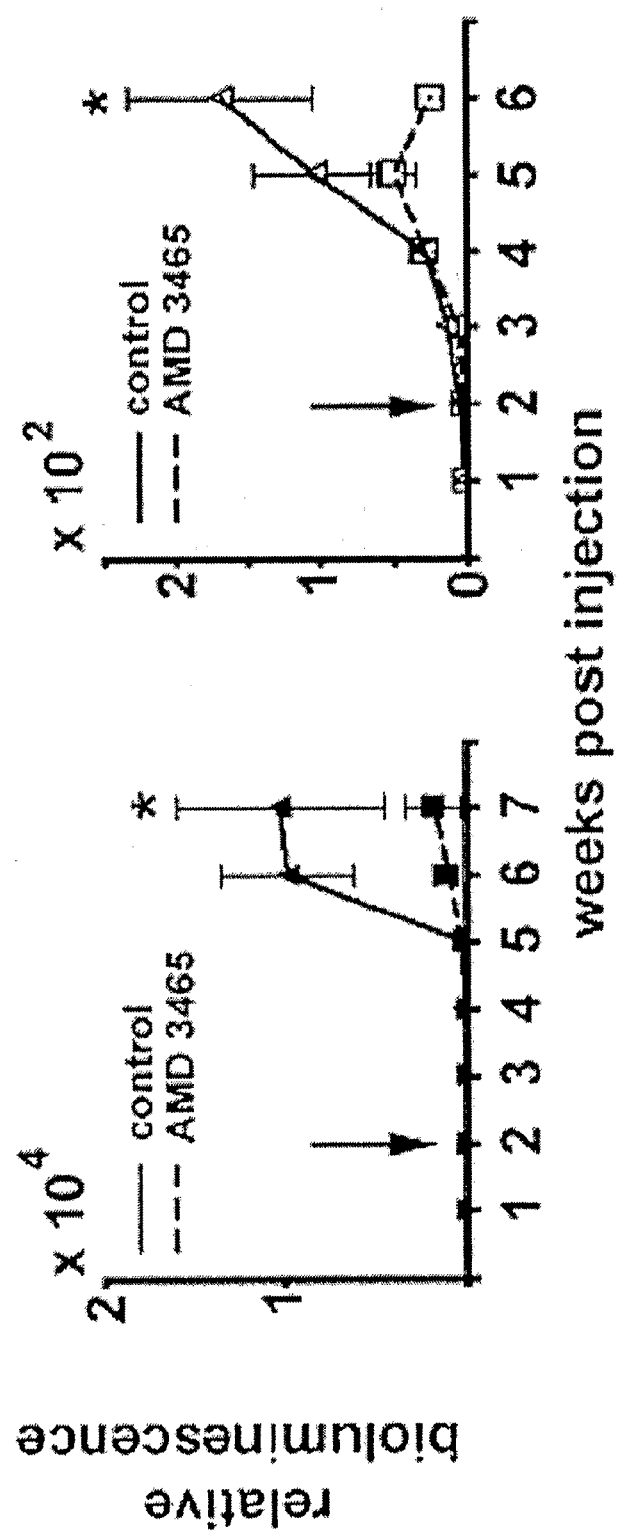

AMD 3465 Blocks In Vivo and In Vitro Tumor Growth and Prevents CXCL12 Induced cAMP Suppression We hypothesized that if suppression of cAMP is the critical growth-promoting signal downstream of CXCR4 activation, then CXCR4 antagonists must block this suppression. Previously we evaluated the in vitro and in vivo anti-tumor activity of the bicyclam antagonist of CXCR4 activation, AMD 3100. This drug, which functions as a competitive antagonist of CXCL12 binding (13, 15, 81) with partial agonist properties (82, 83), exhibited significant anti-tumor activity both in vitro and in vivo. In the present study, we evaluated a newer generation competitive antagonist, AMD 3465. This is a monocyclam with greater affinity for CXCR4 and greater solubility in water (84). CXCL12 again increased U87 and Daoy cell number by greater than 200% (FIG. 16A). AMD 3465 had no significant effect on cell number alone but completely blocked CXCL12 induced growth in both cell lines. Similar to studies with AMD 3100 (3), treatment of intracranial xenograft models of medulloblastoma and glioblastoma with AMD 3465 indicated that ligand activation of CXCR4 is important to tumor growth in vivo. Intracranial xenografts of firefly luciferase expressing U87 or Daoy cells were established as described in Materials and Methods. Tumor bearing animals were treated with either continuous subcutaneous infusion of PBS (control) or AMD 3465 at a dose of 50 μg/day (2.5 mg/kg/day) for 5 weeks. Bioluminescence imaging, which had previously been determined to be an accurate measure of intracranial tumor growth (3), was performed weekly, and the means of three separate experiments with 5 animals/treatment group/experiment were analyzed for mean anti-tumor effect. Similar to what we observed for AMD 3100 treatment, AMD 3465 significantly blocked intracranial xenograft growth (FIG. 16B). U87 GBM xenografts were inhibited by 80% and Daoy xenografts were inhibited by 85%, as compared to controls.

The molecular basis for CXCR4 dependent brain tumor growth is not apparent from the above experiments. Glioblastoma and medulloblastoma typically possess multiple genetic abnormalities that constitutively drive proliferation and survival pathways when assayed in vitro (76, 85). We sought to determine which intracellular pathways downstream of CXCR4 activation were most critical to its tumor growth effects by determining which pathways were both activated by CXCL12 and blocked by cotreatment with CXCL12 and AMD 3465, in manner that correlated with effects on growth. Activation of Erk ½ has been correlated with growth in both astrocytomas (86) and medulloblastomas (87). Therefore we examined Erk ½ activation in Daoy and U87 cells in response to CXCL12 and AMD 3465. We found that there was no clear correlation between Erk½ phosphorylation and response to CXCL12 and AMD 3465 in either cell line (data not shown).

A clear relationship between growth and signaling activity was evident however, in the effects of CXCL12 and AMD 3465 on cAMP suppression. As described above, CXCL12 induced rapid declines in cAMP in both cell lines (FIG. 17). AMD 3465 alone had little to no effect on cAMP levels, and when CXCL12 and AMD 3465 were coadministered, the CXCL12-induced suppression of cAMP was blocked. These data support the hypothesis that the suppression of cAMP is the critical growth-promoting signal downstream of CXCR4 activation and that the anti-tumor effect of AMD 3465 is uniquely dependent upon its ability to block this aspect of CXCR4 signaling.

Figure 18A:
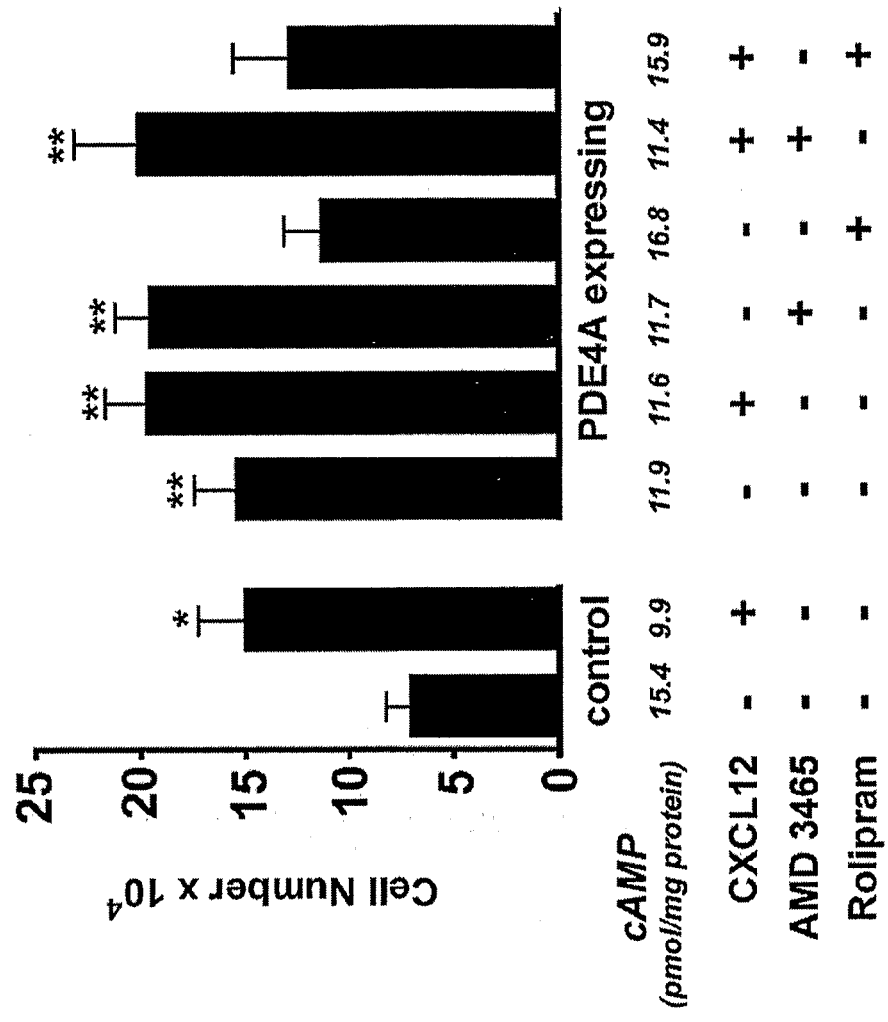
Figure 18B:
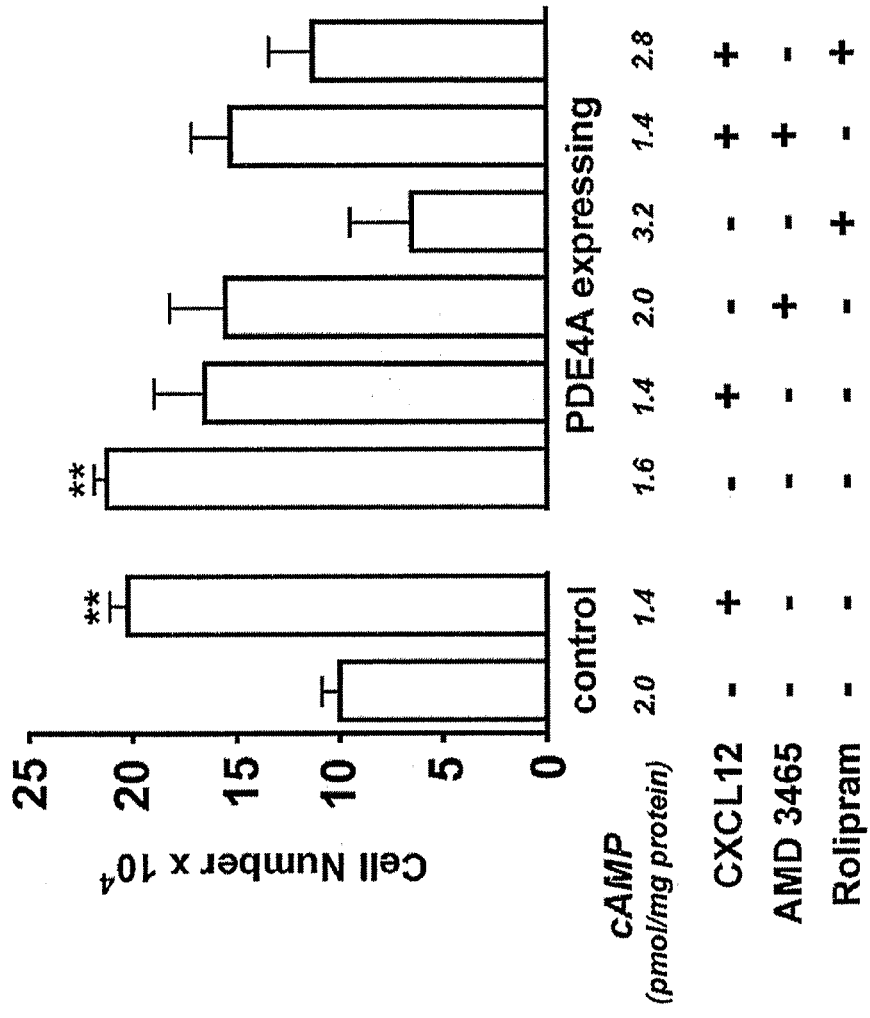

To confirm that cAMP suppression was a critical downstream event in CXCR4-mediated growth, we transfected U87 (FIG. 18A) and Daoy (FIG. 18B) cells with a plasmid encoding PDE4A under the control of a tet-off regulatory element alone, or together with a plasmid encoding the tet transactivator. Thus, in the absence of doxycycline, transactivation results in exogenous PDE4A expression and decreases in intracellular cAMP. If suppression of cAMP is a critical growth-promoting event downstream of CXCR4 activation, then expression of PDE4 should mimic the activity of CXCL12. PDE4A expression driven by the transactivator, resulted in a decline in intracellular cAMP (FIG. 18). This decrease in intracellular cAMP was associated with an increase in cell growth in culture. In both cell lines, increased PDE activity and decreased cAMP was associated with increases in cell number that were comparable to the effect of CXCL12 alone. Under these conditions there was no longer any benefit to CXCL12 treatment as compared to controls and AMD 3465 had no effect on cell number alone or in combination with CXCL12. In contrast, Rolipram continued to exert a growth inhibitory effect. These data confirm that the primary growth promoting activity of CXCL12 is the reduction of intracellular cAMP, and that cAMP suppression is downstream of CXCR4 activation.

Example 15

Figure 19B:
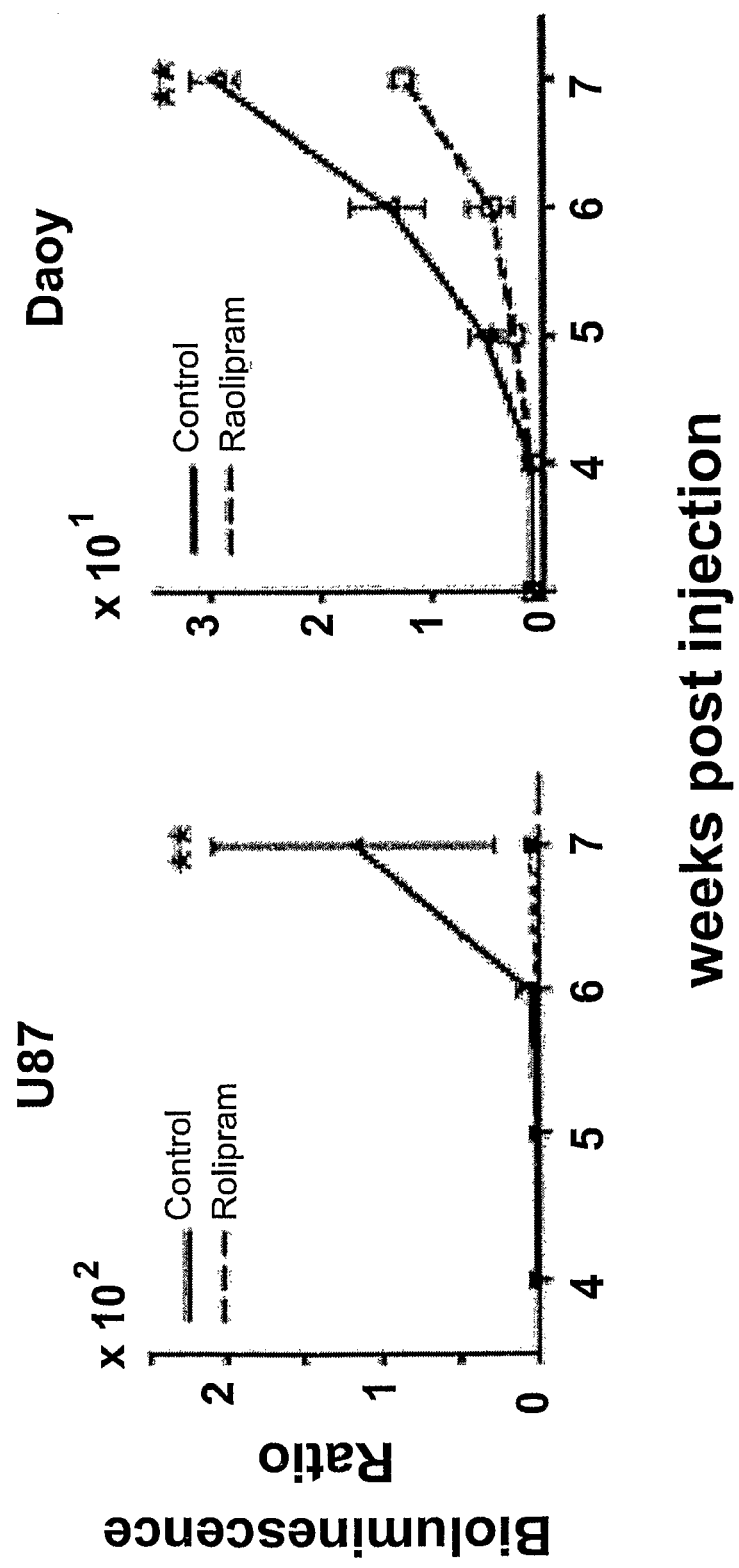
Figure 19C:
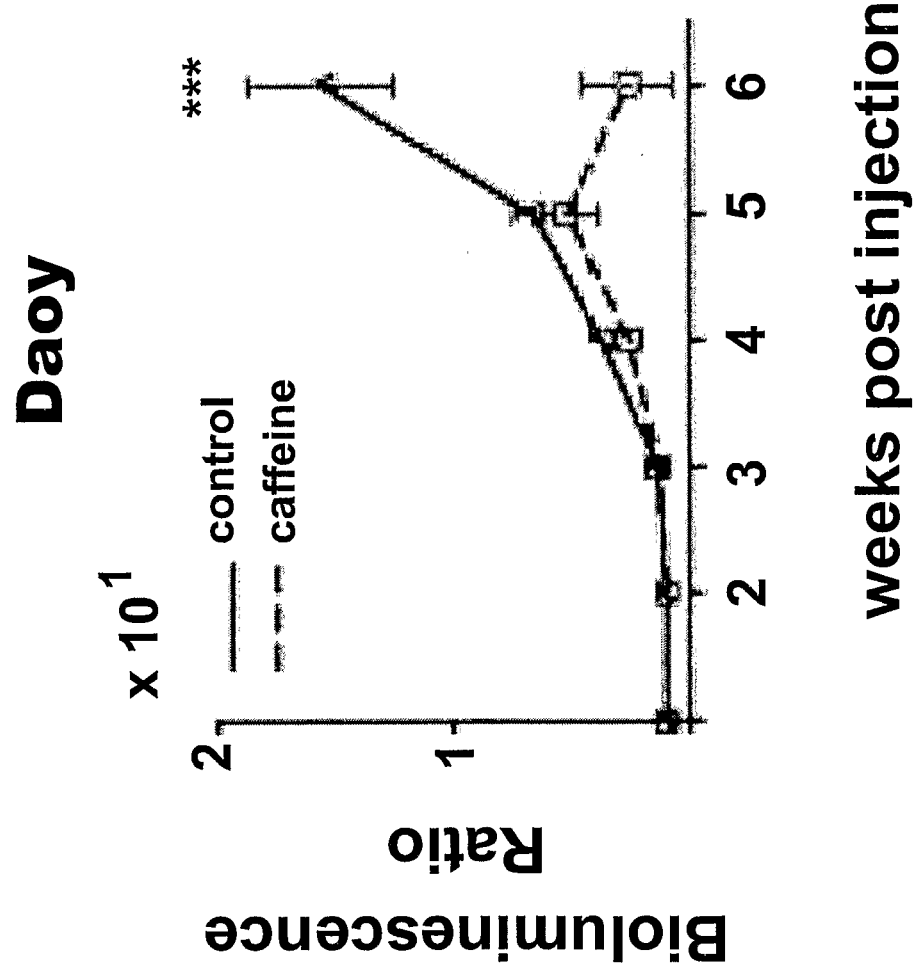

Rolipram Exhibits Significant Anti-Tumor Activity in Intracranial Xenograft Models of Malignant Brain Tumors Given the in vitro activity of Rolipram, we hypothesized that it would exhibit significant anti-tumor activity in vivo. Cohorts of animals with intracranial implants of luciferase-expressing U87 or Daoy xenografts were generated as described in the materials and methods and treated, beginning two weeks after tumor cell injection, with Rolipram (5 μg/g/day) delivered in the drinking water or water alone. Treated animals appeared well throughout the treatment period. Records of individual animal weights indicated that weights were better maintained in the treatment group as compared to the control group (data not shown). Bioluminescence imaging was performed weekly, and the means of three separate experiments with 5 animals/treatment group/experiment were analyzed for mean anti-tumor effect (FIG. 19). Rolipram exhibited significant anti-tumor activity in both tumor models. Rolipram inhibited U87 xenograft growth by 96% (FIG. 19B). This exceeded the growth inhibitory effect of the CXCR4 antagonist AMD 3100 in the same xenograft system (3). The effect of Rolipram on Daoy xenografts was smaller, producing only a 58% inhibition of growth, a value comparable to the activity of AMD 3100 (3). In order to assess whether other phosphodiesterase inhibitors might possess similar anti-tumor activity, we treated intracranial Daoy xenografts with the non-specific phosphodiesterase inhibitor, caffeine (100 μg/g/day). We observed an 85% reduction in tumor growth, an anti-tumor effect that was greater than Rolipram or AMD 3100 (FIG. 19C).

Figure 20B:
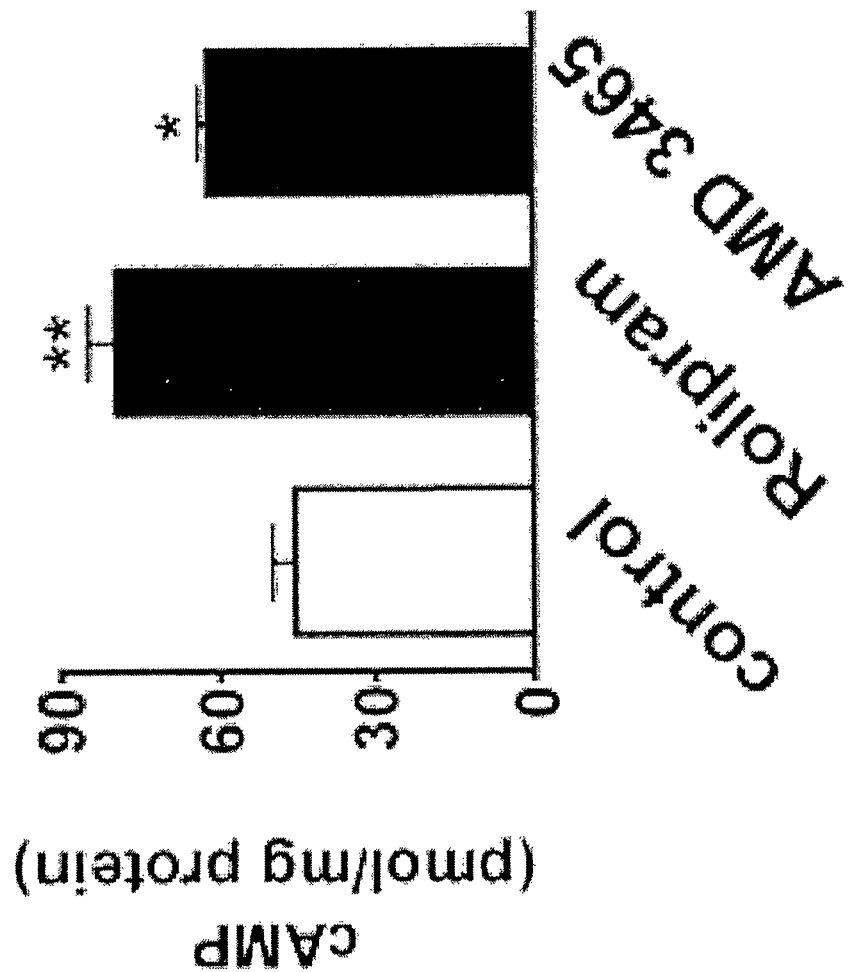

To ascertain whether the in vivo anti-tumor effects of Rolipram and AMD 3465 were correlated with increases in intratumoral cAMP, we repeated the treatment paradigms with Daoy xenografts that had been engineered to express both enhanced green fluorescent protein (EGFP) and firefly luciferase. This was done to enable the reisolation of tumor tissue for extraction of cAMP. Tumor tissue was easily visualized in situ under direct fluorescence microscopy (FIG. 20A). Cyclic AMP was extracted from GFP positive tissue, and cAMP levels were measured by ELISA. The anti-tumor activity of Rolipram and AMD 3465 was associated with a significant increase in the amount of cAMP within tumor tissue (FIG. 20B). Together these data strongly support the hypothesis that cAMP suppression is a key growth-promoting event downstream of CXCR4 activation and that that elevation of tumor cell cAMP has significant anti-brain tumor effect.

The expression of phosphorylated CXCR4 in human brain tumors and the potent anti-xenograft activity of AMD 3100 and AMD 3465 places CXCR4 among the few validated targets for molecular therapy of malignant brain tumors. For CXCR4, EGF receptor (88), PDGF receptor (89) and mTorr (90), abnormal levels of activation are correlated with malignant growth and correction of this activity in the experimental setting can abrogate growth dysregulation (91). Among the issues in translating these findings into clinical practice is the ability to deliver the drug to the tumor in its intracranial location, the ability to antagonize the targeted pathway in situ, as well as the ability to differentially affect tumor cell functions without adversely affecting normal functions of the target molecule. The significant difference we observed between pCXCR4 staining of normal choroid plexus and medulloblastoma suggests that CXCR4 activation may provide a differential target between normal and tumor tissues. The increase in pCXCR4 staining in less to more aggressive medulloblastoma specimens further suggests that differential activation of CXCR4 is a feature of malignancy. These observations are consistent with previous studies from our lab on astrocytic tumors, suggesting that CXCR4 may be an important target in multiple tumor lineages (60).

The appropriate therapeutic approach for antagonizing CXCR4 remains unclear. Single doses of AMD 3100 have proven useful for the mobilization of bone marrow stem cells prior to autologous bone marrow transplant (92, 93). Sustained dosing of AMD 3100 over a 10 day period however, was associated with mild toxicities, and reflective of its effects on bone marrow function, elevations of white blood cell counts were evident throughout an 18 day follow-up period after cessation of AMD 3100 (94). Whether these toxicities and sustained effects on marrow function would preclude the prolonged delivery of AMD 3100, related analogues, or other CXCR4 antagonists to cancer patients, is not known, but the necessity for continued evaluation of this pathway and alternative antagonist approaches is clear.

CXCR4 is a Gi-coupled GPCR and, in these experiments, the suppression of intracellular cAMP appeared to be the critical event in mediating CXCR4-dependent growth effects. This was apparent in the differences between CXCL12-induced cAMP suppression and growth in U87 cells as compared to astrocytes as well as Daoy cells compared to GPCs. The importance of cAMP suppression to growth was also evident in the ability of AC activation with forskolin and PDE4 inhibition with Rolipram to elevate intracellular cAMP and block CXCL12-induced tumor cell growth. The ability of PDE4A overexpression to drive increased growth in a manner that was no longer regulated by CXCL12, and no longer sensitive to AMD 3465, places cAMP suppression downstream of CXCR4 activation in stimulating tumor cell growth. The preserved anti-tumor effect of Rolipram against PDE over-expressing tumor cells further confirms the importance of cAMP to growth regulation, consistent with earlier studies that suggested brain tumor grade was inversely related to AC activity and intracellular levels of cAMP (61, 62).

In our prior studies, the magnitude of the anti-tumor effect of the CXCR4 antagonist AMD 3100 was best correlated with its pro-apoptotic activity (3). Thus, it will be important to identify cAMP-regulated mediators of survival. Targeting cAMP and/or these downstream targets of cAMP might allow for greater specificity in cancer treatment. The role of CXCR4 in maintaining stem cell pools in the bone marrow (93, 95-97) and in regulating lymphocyte trafficking (98, 99) is dependent upon CXCR4-mediated chemotactic effects. This has previously been shown to be a function of CXCR4-mediated activation of Erk½ (100), p38 MAPK (21) and Akt (101, 102). There are no observations to suggest that cAMP suppression is necessary for CXCL12-induced chemotaxis. This might therefore provide a differential target by which the disruption of CXCR4-mediated survival would not interfere with CXCR4-mediated chemotaxis.

The smaller effect of Rolipram on Daoy as compared to U87 xenografts may be due to the presence of cAMP-independent growth-promoting pathways downstream of CXCR4 in Daoy cells, or there being resistance mechanisms to Rolipram in Daoy cells. Cyclic AMP levels are tightly regulated in cells and sustained elevations in cAMP, like those that arise with sustained phosphodiesterase inhibition, can induce regulatory pathways that restore cAMP to lower levels. This commonly involves transcriptional regulation of phosphodiesterase expression. Alternate PDE expression as the basis for the smaller response of Daoy cells to Rolipram was supported by the activity of caffeine, a non-specific PDE inhibitor. Caffeine exhibited a greater anti-tumor effect than Rolipram in Daoy xenografts, supporting the notion that elevated cAMP levels possess important anti-tumor effects and that Daoy cells may have a greater ability to adapt to cAMP elevation as compared to U87 cells.

The significance of identifying cAMP suppression as the mediator of CXCR4 growth effects and Rolipram as an anti-tumor agent lies in the clinical applicability of PDE4 inhibitors. This class of drugs, including, theophylline, AirFlo and Roflumilast, have established applications in the treatment of asthma and chronic obstructive pulmonary disease (105) and as anti-inflammatory agents (80). Rolipram was originally developed as an anti-depressant and anti-dementia medication (79). It crosses an intact blood brain barrier and may therefore have an additional advantage in the treatment of brain tumors. The potential for resistance might be addressed through the use of combined PDE3 and PDE4A inhibitors such as Zardaverine or more global inhibitors such as caffeine. Interestingly caffeine is demonstrated to enhance cytotoxicity in vitro (106), and has been evaluated in several therapeutic regimens (107, 108). Addition of Pentoxiphyllin, an alternative methylxanthine to caffeine, to chemotherapy and radiation therapy for patients with malignant gliomas was evaluated in a clinical trial that was terminated due to excessive toxicity, including decreased consciousness and increased seizure activity (109). Therefore, renewed evaluation of new PDE inhibitors for the treatment of brain and other cancers is warranted.

The importance of targeting CXCR4 in the treatment of brain and other cancers is clear. However, the optimal mode of CXCR4 antagonism is not yet known. These studies suggest that targeting the downstream suppression of cAMP may be efficacious and tractable. The clinical availability of drugs that elevate cAMP and will cross the blood brain barrier makes this an especially attractive treatment approach.

REFERENCES

All references cited in the preceding text of the patent application or in the following reference list, to the extent that they provide exemplary, procedural, or other details supplementary to those set forth herein, are specifically incorporated by reference to the same extent as if each individual publication or patent application was specifically and individually indicated to be incorporated by reference.

1. Balkwill F. The significance of cancer cell expression of the chemokine receptor CXCR4. Semin Cancer Biol 2004; 14(3):171-9.
2. Zlotnik A. Chemokines in neoplastic progression. Semin Cancer Biol 2004; 14(3):181-5.
3. Rubin J B, Kung A L, Klein R S, et al. A small-molecule antagonist of CXCR4 inhibits intracranial growth of primary brain tumors. Proc Natl Acad Sci USA 2003; 100(23):13513-8.
4. Smith M C, Luker K E, Garbow J R, et al. CXCR4 regulates growth of both primary and metastatic breast cancer. Cancer Res 2004; 64(23):8604-12.
5. Lataillade J J, Clay D, Dupuy C, et al. Chemokine SDF-1 enhances circulating CD34(+) cell proliferation in synergy with cytokines: possible role in progenitor survival. Blood 2000; 95(3):756-68.
6. Lataillade J J, Clay D, Bourin P, et al. Stromal cell-derived factor 1 regulates primitive hematopoiesis by suppressing apoptosis and by promoting G(0)/G(1) tran- 7. Rosu-Myles M, Bhatia M. SDF-1 enhances the expansion and maintenance of highly purified human hematopoietic progenitors. Hematol J 2003; 4(2):137-45.
8. Klein R S, Rubin J B, Gibson H D, et al. SDF-1 alpha induces chemotaxis and enhances Sonic hedgehog-induced proliferation of cerebellar granule cells. Development 2001; 128(11):1971-81.
9. Lu M, Grove E A, Miller R J. Abnormal development of the hippocampal dentate gyrus in mice lacking the CXCR4 chemokine receptor. Proc Natl Acad Sci USA 2002; 99(10):7090-5.
10. Bagri A, Gurney T, He X, et al. The chemokine SDF1 regulates migration of dentate granule cells. Development 2002; 129(18):4249-60.
11. Chalasani S H, Baribaud F, Coughlan C M, et al. The chemokine stromal cell-derived factor-1 promotes the survival of embryonic retinal ganglion cells. Neurosci 2003; 23(11):4601-12.
12. Kryczek I, Lange A, Mottram P, et al. CXCL12 and vascular endothelial growth factor synergistically induce neoangiogenesis in human ovarian cancers. Cancer Res 2005; 65(2):465-72.
13. De Clercq E. The bicyclam AMD3100 story. Nat Rev Drug Discov 2003; 2(7):581-7.
14. Gerlach L O, Skerij R T, Bridger G J, Schwartz T W. Molecular interactions of cyclam and bicyclam non-peptide antagonists with the CXCR4 chemokine receptor. J Biol Chem 2001; 276(17):14153-60.
15. Hatse S, Princen K, Bridger G, De Clercq E, Schols D. Chemokine receptor inhibition by AMD3100 is strictly confined to CXCR4. FEBS Left 2002; 527(1-3):255-62.
16. Hendrix C W, Flexner C, MacFarland R T, et al. Pharmacokinetics and safety of AMD-3100, a novel antagonist of the CXCR-4 chemokine receptor, in human volunteers. Antimicrob Agents Chemother 2000; 44(6):1667-73.
17. Haribabu B, Richardson R M, Fisher I, et al. Regulation of human chemokine receptors CXCR4. Role of phosphorylation in desensitization and internalization. J Biol Chem 1997; 272(45):28726-31.
18. Orsini M J, Parent J L, Mundell S J, Marchese A, Benovic J L. Trafficking of the HIV coreceptor CXCR4: role of arrestins and identification of residues in the C-terminal tail that mediate receptor internalization. J Biol Chem 2000; 275(33):25876.
19. Signoret N, Oldridge J, Pelchen-Matthews A, et al. Phorbol esters and SDF-1 induce rapid endocytosis and down modulation of the chemokine receptor CXCR4. J Cell Biol 1997; 139(3):651-64.
20. Cheng Z J, Zhao J, Sun Y, et al. beta-arrestin differentially regulates the chemokine receptor CXCR4-mediated signaling and receptor internalization, and this implicates multiple interaction sites between beta-arrestin and CXCR4. J Biol Chem 2000; 275(4):2479-85.
21. Sun Y, Cheng Z, Ma L, Pei G. Beta-arrestin2 is critically involved in CXCR4-mediated chemotaxis, and this is mediated by its enhancement of p38 MAPK activation. J Biol Chem 2002; 277(51):49212-9.
22. Wang J, Guan E, Roderiquez G, Calvert V, Alvarez R, Norcross M A. Role of tyrosine phosphorylation in ligand-independent sequestration of CXCR4 in human primary monocytes-macrophages. J Biol Chem 2001; 276(52):49236-43.
23. Su S B, Gong W, Grimm M, et al. Inhibition of tyrosine kinase activation blocks the down-regulation of CXC chemokine receptor 4 by HIV-1 gp120 in CD4+ T cells. J Immunol 1999; 162(12):7128-32.
24. Cavenee W K, Furnari, F. B., Nagane, M., Huang, H.-J. S., Newcomb, E. W., Bigner, D. D., Weller, M., Berens, M. E., Plate, K. H., Israel, M. A., Noble, M. D., Kleihues, P. Astrocytic Tumours. In: Cavevee PKWK, editor. World Health Organization Classification of Tumours: Tumours of the Central Nervous System. Lyon: IARC Press; 1999. p. 9-54.
25. Segal R A, Bhattacharyya A, Rua L A, et al. Differential utilization of Trk autophosphorylation sites. J Biol Chem 1996; 271(33):20175-81.
26. Zhou Y, Larsen P H, Hao C, Yong V W. CXCR4 is a major chemokine receptor on glioma cells and mediates their survival. J Biol Chem 2002; 277(51):49481-7.
27. Guinamard R, Signoret N, Ishiai M, et al. B cell antigen receptor engagement inhibits stromal cell-derived factor (SDF)-1alpha chemotaxis and promotes protein kinase C (PKC)-induced internalization of CXCR4. J Exp Med 1999; 189(9):1461-6.
28. Roland J, Murphy B J, Ahr B, et al. Role of the intracellular domains of CXCR4 in SDF-1-mediated signaling. Blood 2003; 101 (2):399-406.
29. Fuller G N, Bigner S H. Amplified cellular oncogenes in neoplasms of the human central nervous system. Mutat Res 1992; 276(3):299-306.
30. Libermann T A, Nusbaum H R, Razon N, et al. Amplification, enhanced expression and possible rearrangement of EGF receptor gene in primary human brain tumours of glial origin. Nature 1985; 313(5998):144-7.
31. Doronin S, Shumay E, Wang H Y, Malbon C C. Akt mediates sequestration of the beta(2)-adrenergic receptor in response to insulin. J Biol Chem 2002; 277(17):15124-31.
32. Salmaggi A, Gelati M, Pollo B, et al. CXCL12 in malignant glial tumors: a possible role in angiogenesis and cross-talk between endothelial and tumoral cells. J Neurooncol 2004; 67(3):305-17.
33. Reis R M, Hara A, Kleihues P, Ohgaki H. Genetic evidence of the neoplastic nature of gemistocytes in astrocytomas. Acta Neuropathol (Berl) 2001; 102(5):422-5.
34. Watanabe K, Tachibana O, Yonekawa Y, Kleihues P, Ohgaki H. Role of gemistocytes in astrocytoma progression. Lab Invest 1997; 76(2):277-84.
35. Burger P C, Vogel F S, Green S B, Strike T A. Glioblastoma multiforme and anaplastic astrocytoma. Pathologic criteria and prognostic implications. Cancer 1985; 56(5):1106-11.
36. Venkatesan S, Rose J J, Lodge R, Murphy P M, Foley J F. Distinct mechanisms of agonist-induced endocytosis for human chemokine receptors CCR5 and CXCR4. Mol Biol Cell 2003; 14(8):3305-24.
37. Hermanson M, Funa K, Hartman M, et al. Platelet-derived growth factor and its receptors in human glioma tissue: expression of messenger RNA and protein suggests the presence of autocrine and paracrine loops. Cancer Res 1992; 52(11):3213-9.
38. Maxwell M, Naber S P, Wolfe H J, et al. Coexpression of platelet-derived growth factor (PDGF) and PDGF-receptor genes by primary human astrocytomas may contribute to their development and maintenance. J Clin Invest 1990; 86(1):131-40.
39. Mauro A, Bulfone A, Turco E, Schiffer D. Coexpression of platelet-derived growth factor (PDGF) B chain and PDGF B-type receptor in human gliomas. Childs Nerv Syst 1991; 7(8):432-6.

40. Guha A, Glowacka D, Carroll R, Dashner K, Black P M, Stiles C D. Expression of platelet derived growth factor and platelet derived growth factor receptor mRNA in a glioblastoma from a patient with Li-Fraumeni syndrome. J Neurol Neurosurg Psychiatry 1995; 58(6):711-4.

41. Hirano H, Lopes M B, Laws E R, Jr., et al. Insulin-like growth factor-1 content and pattern of expression correlates with histopathologic grade in diffusely infiltrating astrocytomas. Neuro-oncol 1999; 1(2): 109-19.

42. Vazquez-Prado J, Casas-Gonzalez P, Garcia-Sainz J A. G protein-coupled receptor cross-talk: pivotal roles of protein phosphorylation and protein-protein interactions. Cell Signal 2003; 15(6):549-57.

43. Miller W E, Lefkowitz R J. Expanding roles for beta-arrestins as scaffolds and adapters in GPCR signaling and trafficking. Curr Opin Cell Biol 2001; 13(2):139-45.

44. Daaka Y, Luttrell L M, Ahn S, et al. Essential role for G protein-coupled receptor endocytosis in the activation of mitogen-activated protein kinase. Biol Chem 1998; 273 (2):685-8.

45. Rempel S A, Dudas S, Ge S, Gutierrez J A. Identification and localization of the cytokine SDF1 and its receptor, CXC chemokine receptor 4, to regions of necrosis and angiogenesis in human glioblastoma. Clin Cancer Res 2000; 6(1): 102-11.

46. Staller P, Sulitkova J, Lisztwan J, Moch H, Oakeley E J, Krek W. Chemokine receptor CXCR4 downregulated by von Hippel-Lindau tumour suppressor pVHL. Nature 2003; 425(6955):307-11.

47. Salcedo R, Wasserman K, Young H A, et al. Vascular endothelial growth factor and basic fibroblast growth factor induce expression of CXCR4 on human endothelial cells: In vivo neovascularization induced by stromal-derived factor-1alpha. Am J Pathol 1999; 154(4):1125-35.

48. Bachelder R E, Wendt M A, Mercurio A M. Vascular endothelial growth factor promotes breast carcinoma invasion in an autocrine manner by regulating the chemokine receptor CXCR4. Cancer Res 2002; 62(24): 7203-6.

49. Kleihues P, Ohgaki H. Primary and secondary glioblastomas: from concept to clinical diagnosis. Neuro-oncol 1999; 1:44-51.

50. Burger P C, Scheithauer B W, Paulus W, Szymas J, Giannini C, Kleihues P. Pilocytic astrocytoma. In: Kleihues P, Cavenee W K, editors. WHO classification of tumours. Pathology and genetics of tumours of the nervous system. Lyon (France): IARC Press; 2000. p. 45-51.

51. Guleng B, Tateishi K, Ohta M, et al. Blockade of the stromal cell-derived factor-1/CXCR4 axis attenuates in vivo tumor growth by inhibiting angiogenesis in a vascular endothelial growth factor-independent manner. Cancer Res 2005; 65:5864-71.

52. Cavenee W K, Furnari F B, Nagane M, et al. Astrocytic tumours. In: Kleihues P, Cavenee W K, editors. WHO classification of tumours. Tumours of the central nervous system. Lyon (France): IARC Press; 2000. p. 9-54.

53. Varela M, Ranuncolo S M, Morand A, et al. EGF-R and PDGF-R, but not bcl-2, overexpression predict overall survival in patients with low-grade astrocytomas. J Surg Oncol 2004; 86:34-40.

54. Torp S H, Helseth E, Dalen A, Unsgaard G. Epidermal growth factor receptor expression in human gliomas. Cancer Immunol Immunother 1991; 33:61-4.

55. Guha A, Dashner K, Black P M, Wagner J A, Stiles C D. Expression of PDGF and PDGF receptors in human astrocytoma operation specimens supports the existence of an autocrine loop. Int J Cancer 1995; 60:168-73.

56. Lois, C., Hong, E. J., Pease, S., Brown, E. J., and Baltimore, D. 2002. Germline transmission and tissue-specific expression of transgenes delivered by lentiviral vectors. Science 295:868-872.

57. Dasgupta, B., Dugan, L. L., and Gutmann, D. H. 2003. The neurofibromatosis 1 gene product neurofibromin regulates pituitary adenylate cyclase-activating polypeptide-mediated signaling in astrocytes. J Neurosci 23:8949-8954.

58. Rubin, J. B., Choi, Y., and Segal, R. A. 2002. Cerebellar proteoglycans regulate sonic hedgehog responses during development. Development 129:2223-2232.

59. Gross, S., and Piwnica-Worms, D. 2005. Real-time imaging of ligand-induced IKK activation in intact cells and in living mice. Nat Methods 2:607-614.

60. Woerner, B. M., Warrington, N. M., Kung, A. L., Perry, A., and Rubin, J. B. 2005. Widespread CXCR4 activation in astrocytomas revealed by phospho-CXCR4-specific antibodies. Cancer Res 65:11392-11399.

61. Furman, M. A., and Shulman, K. 1977. Cyclic AMP and adenyl cyclase in brain tumors. J Neurosurg 46:477-483.

62. Racagni, G., Pezzotta, S., Giordana, M. T., Iuliano, E., Mocchetti, I., Spanu, G., Sangiovanni, G., and Paoletti, P. 1983. Cyclic nucleotides in experimental and human brain tumors. J Neurooncol 1:61-67.

63. Magnaldo, I., Pouyssegur, and Paris, S. 1989. Cyclic AMP inhibits mitogen induced DNA synthesis in hamster fibroblasts, regardless of the signaling pathway involved. FEBS Left 245:65-69.

64. Sewing, A., Burger, C., Brusselbach, S., Schalk, C., Lucibello, F. C., and Muller, R. 1993. Human cyclin D1 encodes a labile nuclear protein whose synthesis is directly induced by growth factors and suppressed by cyclic AMP. J Cell Sci 104 (Pt 2):545-555.

65. Balmanno, K., Millar, T., McMahon, M., and Cook, S. J. 2003. DeltaRaf-1:ER* bypasses the cyclic AMP block of extracellular signal-regulated kinase 1 and 2 activation but not CDK2 activation or cell cycle reentry. Mol Cell Biol 23:9303-9317.

66. Kato, J. Y., Matsuoka, M., Polyak, K., Massague, J., and Sherr, C. J. 1994. Cyclic AMP-induced G1 phase arrest mediated by an inhibitor (p27Kip1) of cyclindependent kinase 4 activation. Cell 79:487-496.

67. Reginato, M. J., Mills, K. R., Paulus, J. K., Lynch, D. K., Sgroi, D. C., Debnath, J., Muthuswamy, S. K., and Brugge, J. S. 2003. Integrins and EGFR coordinately regulate the pro-apoptotic protein Bim to prevent anoikis. Nat Cell Biol 5:733-740.

68. Li, H., Kolluri, S. K., Gu, J., Dawson, M. I., Cao, X., Hobbs, P. D., Lin, B., Chen, G., Lu, J., Lin, F., et al. 2000. Cytochrome c release and apoptosis induced by mitochondrial targeting of nuclear orphan receptor TR3. Science 289:1159-1164.

69. Harada, H., Becknell, B., Wilm, M., Mann, M., Huang, L. J., Taylor, S. S., Scott, J. D., and Korsmeyer, S. J. 1999. Phosphorylation and inactivation of BAD by mitochondria-anchored protein kinase A. Mol Cell 3:413-422.

70. Sehgal, A., Keener, C., Boynton, A. L., Warrick, J., and Murphy, G. P. 1998. CXCR-4, a chemokine receptor, is overexpressed in and required for proliferation of glioblastoma tumor cells. J Surg Oncol 69:99-104.

71. Barbero, S., Bonavia, R., Bajetto, A., Porcile, C., Pirani, P., Ravetti, J. L., Zona, G. L., Spaziante, R., Florio, T., and Schettini, G. 2003. Stromal cell-derived factor 1alpha stimulates human glioblastoma cell growth through the activation of both extracellular signal-regulated kinases ½ and Akt. Cancer Res 63:1969-1974.
72. Ehtesham, M., Winston, J. A., Kabos, P., and Thompson, R. C. 2006. CXCR4 expression mediates glioma cell invasiveness. Oncogene.
73. Zhang, J., Sarkar, S., and Yong, V. W. 2005. The chemokine stromal cell derived factor-1 (CXCL12) promotes glioma invasiveness through MT2-matrix metalloproteinase. Carcinogenesis 26:2069-2077.
74. Marinissen, M. J., and Gutkind, J. S. 2001. G-protein-coupled receptors and signaling networks: emerging paradigms. Trends Pharmacol Sci 22:368-376.
75. Packer, R. J., Cogen, P., Vezina, G., and Rorke, L. B. 1999. Medulloblastoma: clinical and biologic aspects. Neuro-oncol 1:232-250.
76. Giangaspero, F., Bigner, S. H., Kleihues, P., Pietsch, T., Trojanowski, J. Q. 2000. Medulloblastoma. In World Health organization Classification of Tumours: Pathology and genetics of tumours of the central nervous system. P. C. Kleihues, W. K., editor. Lyon: IARC Press.
77. Sanai, N., Alvarez-Buylla, A., and Berger, M. S. 2005. Neural stem cells and the origin of gliomas. N Engl J Med 353:811-822.
78. Oliver, T. G., Read, T. A., Kessler, J. D., Mehmeti, A., Wells, J. F., Huynh, T. T., Lin, S. M., and Wechsler-Reya, R. J. 2005. Loss of patched and disruption of granule cell development in a pre-neoplastic stage of medulloblastoma. Development 132:2425-2439.
79. Wachtel, H., and Schneider, H. H. 1986. Rolipram, a novel antidepressant drug, reverses the hypothermia and hypokinesia of monoamine-depleted mice by an action beyond postsynaptic monoamine receptors. Neuropharmacology 25:1119-1126.
80. Dyke, H. J., and Montana, J. G. 2002. Update on the therapeutic potential of PDE4 inhibitors. Expert Opin Investig Drugs 11:1-13.
81. Bridger, G. J., Skerlj, R. T., Padmanabhan, S., Martellucci, S. A., Henson, G. W., Struyf, S., Witvrouw, M., Schols, D., and De Clercq, E. 1999. Synthesis and structure-activity relationships of phenylenebis(methylene)-linked bisazamacrocycles that inhibit HIV-1 and HIV-2 replication by antagonism of the chemokine receptor CXCR4. J Med Chem 42:3971-3981.
82. Zhang, W. B., Navenot, J. M., Haribabu, B., Tamamura, H., Hiramatu, K., Omagari, A., Pei, G., Manfredi, J. P., Fujii, N., Broach, J. R., et al. 2002. A point mutation that confers constitutive activity to CXCR4 reveals that T140 is an inverse agonist and that AMD3100 and ALX40-4C are weak partial agonists. J Biol Chem 277:24515-24521.
83. Trent, J. O., Wang, Z. X., Murray, J. L., Shao, W., Tamamura, H., Fujii, N., and Peiper, S. C. 2003. Lipid bilayer simulations of CXCR4 with inverse agonists and weak partial agonists. J Biol Chem 278:47136-47144.
84. Hatse, S., Princen, K., De Clercq, E., Rosenkilde, M. M., Schwartz, T. W., Hernandez-Abad, P. E., Skerij, R. T., Bridger, G. J., and Schols, D. 2005. AMD3465, a monomacrocyclic CXCR4 antagonist and potent HIV entry inhibitor. Biochem Pharmacol 70:752-761.
85. Kleihues, P., Burger, P. C., Collins, V. P., Newcomb, E. W., Ohgaki, H., Cavenee, W. K. 2000. Glioblastoma. In World Health organization Classification of Tumours: Pathology and genetics of tumours of the central nervous system. P. C. Kleihues, W. K., editor. Lyon: IARC Press.
86. Mawrin, C., Diete, S., Treuheit, T., Kropf, S., Vorwerk, C. K., Boltze, C., Kirches, E., Firsching, R., and Dietzmann, K. 2003. Prognostic relevance of MAPK expression in glioblastoma multiforme. Int J Oncol 23:641-648.
87. MacDonald, T. J., Brown, K. M., LaFleur, B., Peterson, K., Lawlor, C., Chen, Y., Packer, R. J., Cogen, P., and Stephan, D. A. 2001. Expression profiling of medulloblastoma: PDGFRA and the RAS/MAPK pathway as therapeutic targets for metastatic disease. Nat Genet. 29:143-152.
88. Lassman, A. B., Abrey, L. E., and Gilbert, M. R. 2006. Response of glioblastomas to EGFR kinase inhibitors. N Engl J Med 354:525-526; author reply 525-526.
89. Kilic, T., Alberta, J. A., Zdunek, P. R., Acar, M., Iannarelli, P., O'Reilly, T., Buchdunger, E., Black, P. M., and Stiles, C. D. 2000. Intracranial inhibition of platelet-derived growth factor-mediated glioblastoma cell growth by an orally active kinase inhibitor of the 2-phenylaminopyrimidine class. Cancer Res 60:5143-5150.
90. Dasgupta, B., Yi, Y., Chen, D. Y., Weber, J. D., and Gutmann, D. H. 2005. Proteomic analysis reveals hyperactivation of the mammalian target of rapamycin pathway in neurofibromatosis 1-associated human and mouse brain tumors. Cancer Res 65:2755-2760.
91. Kondo, Y., Hollingsworth, E. F., and Kondo, S. 2004. Molecular targeting for malignant gliomas (Review). Int J Oncol 24:1101-1109.
92. Devine, S. M., Flomenberg, N., Vesole, D. H., Liesveld, J., Weisdorf, D., Badel, K., Calandra, G., and DiPersio, J. F. 2004. Rapid mobilization of CD34+ cells following administration of the CXCR4 antagonist AMD3100 to patients with multiple myeloma and non-Hodgkin's lymphoma. J Clin Oncol 22:1095-1102.
93. Broxmeyer, H. E., Orschell, C. M., Clapp, D. W., Hangoc, G., Cooper, S., Plett, P. A., Liles, W. C., Li, X., Graham-Evans, B., Campbell, T. B., et al. 2005. Rapid mobilization of murine and human hematopoietic stem and progenitor cells with AMD3100, a CXCR4 antagonist. J Exp Med 201:1307-1318.
94. Hendrix, C. W., Collier, A. C., Lederman, M. M., Schols, D., Pollard, R. B., Brown, S., Jackson, J. B., Coombs, R. W., Glesby, M. J., Flexner, C. W., et al. 2004. Safety, Pharmacokinetics, and Antiviral Activity of AMD3100, a Selective CXCR4 Receptor Inhibitor, in HIV-1 Infection. J Acquir Immune Defic Syndr 37:1253-1262.
95. Ma, Q., Jones, D., and Springer, T. A. 1999. The chemokine receptor CXCR4 is required for the retention of B lineage and granulocytic precursors within the bone marrow microenvironment. Immunity 10:463-471.
96. Ishii, T., Nishihara, M., Ma, F., Ebihara, Y., Tsuji, K., Asano, S., Nakahata, T., and Maekawa, T. 1999. Expression of stromal cell-derived factor-1/pre-B cell growth-stimulating factor receptor, CXC chemokine receptor 4, on CD34+ human bone marrow cells is a phenotypic alteration for committed lymphoid progenitors. J Immunol 163:3612-3620.
97. Basu, S., and Broxmeyer, H. E. 2005. Transforming growth factor-{beta}1 modulates responses of CD34+ cord blood cells to stromal cell-derived factor-1/CXCL12. Blood 106:485-493.
98. Bleul, C. C., Schultze, J. L., and Springer, T. A. 1998. B lymphocyte chemotaxis regulated in association with microanatomic localization, differentiation state, and B cell receptor engagement. J Exp Med 187:753-762.
99. Vicente-Manzanares, M., Rey, M., Jones, D. R., Sancho, D., Mellado, M., Rodriguez-Frade, J. M., del Pozo, M. A., Yanez-Mo, M., de Ana, A. M., Martinez, A. C., et al. 1999. Involvement of phosphatidylinositol 3-kinase in stromal cell derived factor-1 alpha-induced lymphocyte polarization and chemotaxis. J Immunol 163:4001-4012.
100. Floridi, F., Trettel, F., Di Bartolomeo, S., Ciotti, M. T., and Limatola, C. 2003. Signalling pathways involved in the chemotactic activity of CXCL12 in cultured rat cerebellar neurons and CHP100 neuroepithelioma cells. J Neuroimmunol 135:38-46.
101. Sotsios, Y., Whittaker, G. C., Westwick, J., and Ward, S. G. 1999. The CXC chemokine stromal cell-derived factor activates a Gi-coupled phosphoinositide 3-kinase in T lymphocytes. J Immunol 163:5954-5963.
102. Roland, J., Murphy, B. J., Ahr, B., Robert-Hebmann, V., Delauzun, V., Nye, K. E., Devaux, C., and Biard-Piechaczyk, M. 2003. Role of the intracellular domains of CXCR4 in SDF-1-mediated signaling. Blood 101: 399-406.
103. Weissinger, E. M., Oettrich, K., Evans, C., Genieser, H. G., Schwede, F., Dangers, M., Dammann, E., Kolb, H. J., Mischak, H., Ganser, A., et al. 2004. Activation of protein kinase A (PKA) by 8-Cl-cAMP as a novel approach for antileukaemic therapy. Br J Cancer 91:186-192.
104. Kim, S. N., Ahn, Y. H., Kim, S. G., Park, S. D., Cho-Chung, Y. S., and Hong, S. H. 2001. 8-Cl-cAMP induces cell cycle-specific apoptosis in human cancer cells. Int J Cancer 93:33-41.
105. Cowan, C. 2005. Roflumilast for asthma and chronic obstructive pulmonary disease. Issues Emerg Health Technol: 1-4.
106. Janss, A. J., Levow, C., Bernhard, E. J., Muschel, R. J., McKenna, W. G., Sutton, L., and Phillips, P. C. 1998. Caffeine and staurosporine enhance the cytotoxicity of cisplatin and camptothecin in human brain tumor cell lines. Exp Cell Res 243:29-38.
107. Ahmed, S., Vaitkevicius, V. K., Zalupski, M. M., Du, W., Arlauskas, P., Gordon, C., Kellogg, C., and Shields, A. F. 2000. Cisplatin, cytarabine, caffeine, and continuously infused 5-fluorouracil (PACE) in the treatment of advanced pancreatic carcinoma: a phase II study. Am J Clin Oncol 23:420-424.
108. Tsuchiya, H., Yamamoto, N., Asada, N., Terasaki, T., Kanazawa, Y., Takanaka, T., Nishijima, H., and Tomita, K. 2000. Caffeine-potentiated radiochemotherapy and function-saving surgery for high-grade soft tissue sarcoma. Anticancer Res 20:2137-2143.
109. Stewart, D. J., Dahrouge, S., Agboola, O., and Girard, A. 1997. Cranial radiation and concomitant cisplatin and mitomycin-C plus resistance modulators for malignant gliomas. J Neurooncol 32:161-168.
110. Friedman J M, Gutmann, D. H., MacCollin, M. M., Riccardi, V. M. Neurofibromatosis. 3rd ed: Johns Hopkins Press; 1999.
111. Rubin J B, Gutmann D H. Neurofibromatosis type I—a model for nervous system tumour formation? Nature Cancer Reviews 2005; 5(7):557-64.
112. Listernick R, Louis D N, Packer R J, Gutmann DH. Optic pathway gliomas in children with neurofibromatosis 1: consensus statement from the NF1 Optic Pathway Glioma Task Force. Ann Neurol 1997; 41(2):143-9.
113. Gutmann D H, Donahoe J, Brown T, James C D, Perry A. Loss of neurofibromatosis 1 (NF1) gene expression in NF1-associated pilocytic astrocytomas. Neuropathol Appl Neurobiol 2000; 26(4):361-7.
114. Gutmann D H, James C D, Poyhonen M, et al. Molecular analysis of astrocytomas presenting after age 10 in individuals with NF1. Neurology 2003; 61 (10): 1397-400.
115. Kluwe L, Hagel C, Tatagiba M, et al. Loss of NF1 alleles distinguish sporadic from NF1-associated pilocytic astrocytomas. J Neuropathol Exp Neurol 2001; 60(9):917-20.
116. Bajenaru M L, Hernandez M R, Perry A, et al. Optic nerve glioma in mice requires astrocyte Nf1 gene inactivation and Nf1 brain heterozygosity. Cancer Res 2003; 63(24):8573-7.
117. Dasgupta B, Li W, Perry A, Gutmann D H. Glioma formation in neurofibromatosis 1 reflects preferential activation of K-RAS in astrocytes. Cancer Res 2005; 65(1):236-45.
118. Bajenaru M L, Zhu Y, Hedrick N M, Donahoe J, Parada L F, Gutmann D H. Astrocyte-specific inactivation of the neurofibromatosis 1 gene (NF1) is insufficient for astrocytoma formation. Mol Cell Biol 2002; 22(14): 5100-13.
119. Bajenaru M L, Garbow J R, Perry A, Hernandez M R, Gutmann D H. Natural history of neurofibromatosis 1-associated optic nerve glioma in mice. Ann Neurol 2005; 57(1): 119-27.
120. Ballester R, Marchuk D, Boguski M, et al. The NF1 locus encodes a protein functionally related to mammalian GAP and yeast IRA proteins. Cell 1990; 63(4):851-9.
121. Martin G A, Viskochil D, Bollag G, et al. The GAP-related domain of the neurofibromatosis type 1 gene product interacts with ras p21. Cell 1990; 63(4):843-9.
122. Xu G F, O'Connell P, Viskochil D, et al. The neurofibromatosis type 1 gene encodes a protein related to GAP. Cell 1990; 62(3):599-608.
123. Marchuk D A, Saulino A M, Tavakkol R, et al. cDNA cloning of the type 1 neurofibromatosis gene: complete sequence of the NF1 gene product. Genomics 1991; 11(4):931-40.
124. Gutmann D H, Wood D L, Collins F S. Identification of the neurofibromatosis type 1 gene product. Proc Natl Acad Sci USA 1991; 88(21):9658-62.
125. Andersen L B, Ballester R, Marchuk D A, et al. A conserved alternative splice in the von Recklinghausen neurofibromatosis (NF1) gene produces two neurofibromin isoforms, both of which have GTPase-activating protein activity. Mol Cell Biol 1993; 13(1):487-95.
126. Phillips R A, Hunter J L, Eccleston J F, Webb M R. The mechanism of Ras GTPase activation by neurofibromin. Biochemistry 2003; 42(13):3956-65.
127. DeClue J E, Papageorge A G, Fletcher J A, et al. Abnormal regulation of mammalian p21 ras contributes to malignant tumor growth in von Recklinghausen (type neurofibromatosis. Cell 1992; 69(2):265-73.
128. Burchill S A, Berry P A, Bradbury F M, Lewis I J. Contrasting levels of p21ras activation and expression of neurofibromin in peripheral primitive neuroectodermal tumour and neuroblastoma cells, and their response to retinoic acid. J Neurol Sci 1998; 157(2):129-37.
129. Bollag G, Clapp D W, Shih S, et al. Loss of NF1 results in activation of the Ras signaling pathway and leads to aberrant growth in haematopoietic cells. Nat Genet. 1996; 12(2):144-8.

130. Guha A. Ras activation in astrocytomas and neurofibromas. Can J Neurol Sci 1998; 25(4):267-81.
131. Feldkamp M M, Angelov L, Guha A. Neurofibromatosis type 1 peripheral nerve tumors: aberrant activation of the Ras pathway. Surg Neurol 1999; 51 (2):211-8.
132. The I, Hannigan G E, Cowley G S, et al. Rescue of a *Drosophila* NF1 mutant phenotype by protein kinase A. Science 1997; 276(5313):791-4.
133. Guo H F, The I, Hannan F, Bernards A, Zhong Y. Requirement of *Drosophila* NF1 for activation of adenylyl cyclase by PACAP38-like neuropeptides. Science 1997; 276(5313):795-8.
134. Dasgupta B, Dugan L L, Gutmann D H. The neurofibromatosis 1 gene product neurofibromin regulates pituitary adenylate cyclase-activating polypeptide-mediated signaling in astrocytes. J Neurosci 2003; 23(26):8949-54.
135. Klein R S, Rubin J B, Gibson H D, et al. SDF-1 alpha induces chemotaxis and enhances Sonic hedgehog-induced proliferation of cerebellar granule cells. Development 2001; 128(11):1971-81.
136. Peng H, Huang Y, Rose J, et al. Stromal cell-derived factor 1-mediated CXCR4 signaling in rat and human cortical neural progenitor cells. J Neurosci Res 2004; 76(1):35-50.
137. Klein R S, Rubin J B. Immune and nervous system CXCL12 and CXCR4: parallel roles in patterning and plasticity. Trends Immunol 2004; 25(6):306-14.
138. Takuma K, Baba A, Matsuda T. Astrocyte apoptosis: implications for neuroprotection. Prog Neurobiol 2004; 72(2): 111-27.
139. Gomez Del Pulgar T, De Ceballos M L, Guzman M, Velasco G. Cannabinoids protect astrocytes from ceramide-induced apoptosis through the phosphatidylinositol 3-kinase/protein kinase B pathway. J Biol Chem 2002; 277(39):36527-33.
140. Gainetdinov R R, Premont R T, Bohn L M, Lefkowitz R J, Caron M G. Desensitization of G protein-coupled receptors and neuronal functions. Annu Rev Neurosci 2004; 27:107-44.
141. Ferguson S S, Barak L S, Zhang J, Caron M G. G-protein-coupled receptor regulation: role of G-protein-coupled receptor kinases and arrestins. Can J Physiol Pharmacol 1996; 74(10): 1095-110.
142. Penela P, Ribas C, Mayor F, Jr. Mechanisms of regulation of the expression and function of G protein-coupled receptor kinases. Cell Signal 2003; 15(11):973-81.
143. Orsini M J, Parent J L, Mundell S J, Marchese A, Benovic J L. Trafficking of the HIV coreceptor CXCR4: role of arrestins and identification of residues in the C-terminal tail that mediate receptor internalization. J Biol Chem 2000; 275(33):25876.
144. Pitcher J A, Tesmer J J, Freeman J L, Capel W D, Stone W C, Lefkowitz R J. Feedback inhibition of G protein-coupled receptor kinase 2 (GRK2) activity by extracellular signal-regulated kinases. J Biol Chem 1999; 274(49):34531-4.
145. Lewis R A, Gerson L P, Axelson K A, Riccardi V M, Whitford R P. Von Recklinghausen neurofibromatosis. II. Incidence of optic gliomata. Opthalmology 1984; 91 (8):929-35.
146. Rosser T, Packer R J. Intracranial neoplasms in children with neurofibromatosis J Child Neurol 2002; 17(8): 630-7; discussion 46-51.
147. Burger P C, Scheithauer B W, Paulus W, Szymas J, Giannini C, Kleihues P. Pilocytic aatrocytoma. In: Kleihues P C, W. K., editor. World Health Organization 27
148. Classification of Tumours: Pathology and genetics of tumours of the nervous system. Lyon: IARC Press; 2000. p. 45-51.
149. Riccardi V M. Cutaneous manifestation of neurofibromatosis: cellular interaction, pigmentation, and mast cells. Birth Defects Orig Artic Ser 1981; 17(2):129-45.
150. Yang F C, Ingram D A, Chen S, et al. Neurofibromin-deficient Schwann cells secrete a potent migratory stimulus for Nf1+/−mast cells. J Clin Invest 2003; 112 (12):1851-61.
151. Bajenaru M L, Donahoe J, Corral T, et al. Neurofibromatosis 1 (NF1) heterozygosity results in a cell-autonomous growth advantage for astrocytes. Glia 2001; 33(4): 314-23.
152. Gutmann D H, Loehr A, Zhang Y, Kim J, Henkemeyer M, Cashen A. Haploinsufficiency for the neurofibromatosis 1 (NF1) tumor suppressor results in increased astrocyte proliferation. Oncogene 1999; 18(31):4450-9.
153. Zhu Y, Harada T, Liu L, et al. Inactivation of NF1 in CNS causes increased glial progenitor proliferation and optic glioma formation. Development 2005; 132(24): 5577-88.
154. Ishii M, Kurachi Y. Physiological actions of regulators of G-protein signaling (RGS) proteins. Life Sci 2003; 74(2-3):163-71.
155. Ferguson S S, Zhang J, Barak L S, Caron M G. Molecular mechanisms of G protein-coupled receptor desensitization and resensitization. Life Sci 1998; 62(17-18): 1561-5.
156. Metaye T, Menet E, Guilhot J, Kraimps J L. Expression and activity of g protein coupled receptor kinases in differentiated thyroid carcinoma. J Clin Endocrinol Metab 2002; 87(7):3279-86.

What is claimed is:

1. A purified chemokine receptor antibody that selectively binds to an activated form of the receptor CXCR4, but not to a non activated form of the receptor CXCR4.

2. The purified chemokine receptor antibody of claim 1, wherein the antibody selectively binds to a phosphorylated form of the receptor CXCR4 but not to a non phosphorylated form of the receptor CXCR4.

3. The purified chemokine receptor antibody of claim 1, wherein the antibody selectively binds to a CXCR4 receptor phosphorylated on serine residue 338 but not to a CXCR4 receptor phosphorylated on serine residue 339.

4. The purified chemokine receptor antibody of claim 1, wherein the antibody selectively binds to a CXCR4 receptor phosphorylated on serine residue 339 but not to a CXCR4 receptor phosphorylated on serine residue 338.

5. The purified chemokine receptor antibody of claim 1, wherein the antibody binds selectively to a ligand activated form of the CXCR4 receptor.

6. The purified chemokine receptor antibody of claim 1, wherein the antibody is selected from the group consisting of a polyclonal antibody, a monoclonal antibody, a chimeric antibody, a single chain antibody, a humanized antibody, a Fab fragment, a F(ab')$_2$ fragment, and fragments produced by a Fab expression library.

7. The purified chemokine receptor antibody of claim 1, wherein the receptor is present within a cell selected from the group consisting of a non-malignant cell, a malignant tumor cell, and a pre-malignant tumor cell.

8. The purified chemokine receptor antibody of claim 7, wherein the tumor cell comprises a cancer that is selected from the group consisting of skin, prostate, pancreatic, cervical, ovarian, bladder, brain, lung, colorectal, renal, head and neck, stomach, uterine, lymphoma, including B cell lymphoma, breast, and hematological.

9. The purified chemokine receptor antibody of claim 7, wherein the brain cancer is selected from the group consisting of glioblastoma, glioma, meningioma, astrocytoma, medulloblastoma, neuroectodermal cancer and neuroblastoma.

10. The purified chemokine receptor antibody of claim 1, wherein the antibody is labeled with a detectable marker.

11. A diagnostic test for a disorder associated with increased activation of CXCR4 in a subject, the test comprising:
   a. measuring the level of activated CXCR4 in a biological sample of the subject; and by contacting said biological sample with an antibody that selectively binds to an activated form of CXCR4 but not to the non activated form of CXCR4.
   b. comparing the measured level of activated CXCR4 of (a) with the level of activated CXCR4 in a biological sample from a normal control subject, wherein an increase in the measured level of activated CXCR4 in the subject compared to the control subject indicates the presence of the disorder in the subject.

12. The diagnostic test of claim 11, wherein the biological sample is a non-malignant cell.

13. The diagnostic test of claim 11, wherein the disorder is a tumor cell that is malignant or pre-malignant.

14. The diagnostic test of claim 13, wherein the tumor cell comprises a cancer that is selected from the group consisting of skin, prostate, pancreatic, cervical, ovarian, bladder, brain, lung, colorectal, renal, head and neck, stomach, uterine, lymphoma, including B cell lymphoma, breast, and hematological.

15. The diagnostic test of claim 14, wherein the brain cancer is selected from the group consisting of glioblastoma, glioma, meningioma, astrocytoma, medulloblastoma, neuroectodermal cancer and neuroblastoma.

16. The diagnostic test of claim 11, wherein the subject is a human.

17. The diagnostic test of claim 11, wherein the antibody is selected from the group consisting of a polyclonal antibody, a monoclonal antibody, a chimeric antibody, a single chain antibody, a humanized antibody, a Fab fragment, a F(ab')$_2$ fragment, and fragments produced by a Fab expression library.

18. A method for determining whether a biological sample contains an activated form of CXCR4, the method comprising:
   a. contacting the biological sample with an antibody that selectively binds to an activated form of CXCR4 but not to the non activated form of CXCR4; and
   b. determining whether the antibody binds to the biological sample, wherein the binding of the antibody to the biological sample indicates that the biological sample contains an activated form of CXCR4.

19. The method of claim 18, wherein the antibody selectively binds to a phosphorylated form of CXCR4 but not to a non phosphorylated form of CXCR4.

20. The method of claim 18, wherein CXCR4 is ligand activated.

21. The method of claim 18, wherein the antibody selectively binds to CXCR4 phosphorylated on serine residue 338 but not to CXCR4 phosphorylated on serine residue 339.

22. The method of claim 18, wherein the antibody selectively binds to CXCR4 phosphorylated on serine residue 339 but not to CXCR4 phosphorylated on serine residue 338.

23. The method of claim 18, wherein the antibody is selected from the group consisting of a polyclonal antibody, a monoclonal antibody, a chimeric antibody, a single chain antibody, a humanized antibody, a Fab fragment, a F(ab')$_2$ fragment, and fragments produced by a Fab expression library.

24. The method of claim 18, wherein the receptor is present within a cell selected from the group consisting of a non-malignant cell, a malignant tumor cell, and a pre-malignant tumor cell.

25. The method of claim 24, wherein the tumor cell comprises a cancer that is selected from the group consisting of skin, prostate, pancreatic, cervical, ovarian, bladder, brain, lung, colorectal, renal, head and neck, stomach, uterine, lymphoma, including B cell lymphoma, breast, and hematological.

26. The method of claim 25, wherein the brain cancer is selected from the group consisting of glioblastoma, glioma, meningioma, astrocytoma, medulloblastoma, neuroectodermal cancer and neuroblastoma.

27. The method of claim 18, wherein the chemokine receptor antibody is labeled with a detectable marker selected from the group consisting of a chemiluminescent moiety, an enzymatic moiety, a fluorescent moiety, and a radioactive moiety.

28. A method for screening a compound for effectiveness as an antagonist of CXCR4 activation, the method comprising:
   a. combining the compound with a sample comprising non activated CXCR4 to form a mixture comprising the sample and the compound;
   b. adding a ligand activator of CXCR4 to the mixture under conditions suitable for the ligand to activate CXCR4; and
   by contacting said sample with an antibody that selectively binds to an activated form of CXCR4 but not to the non activated form of CXCR4.
   c. detecting CXCR4 activation in the mixture of (b), wherein CXCR4 activation indicates that the compound does not have CXCR4 antagonist activity.

29. The method of claim 28, wherein the antibody is labeled with a detectable marker selected from the group consisting of a chemiluminescent moiety, an enzymatic moiety, a fluorescent moiety, and a radioactive moiety.

30. The method of claim 28, wherein the antibody is selected from the group consisting of a polyclonal antibody, a monoclonal antibody, a chimeric antibody, a single chain antibody, a humanized antibody, a Fab fragment, a $F(ab')_2$ fragment, and fragments produced by a Fab expression library.

31. The method of claim 28, wherein the ligand activator is CXCL12.

* * * * *

UNITED STATES PATENT AND TRADEMARK OFFICE
CERTIFICATE OF CORRECTION

PATENT NO. : 7,892,767 B2
APPLICATION NO. : 11/994048
DATED : February 22, 2011
INVENTOR(S) : Joshua Rubin et al.

It is certified that error appears in the above-identified patent and that said Letters Patent is hereby corrected as shown below:

Column 51, line 57, cancel the text "; and"

Column 51, line 60, cancel the text "." and insert --; and--

Column 54, lines 1 to 3, cancel the text "by contacting said sample with an antibody that selectively binds to an activated form of CXCR4 but not to the non activated form of CXCR4."

Column 54, line 4, after "of (b)" and before "," insert --by contacting said sample with an antibody that selectively binds to an activated form of CXCR4 but not to the non activated form of CXCR4--

Signed and Sealed this
Fifteenth Day of November, 2011

David J. Kappos
*Director of the United States Patent and Trademark Office*